(12) United States Patent
Nakanishi et al.

(10) Patent No.: US 7,429,670 B2
(45) Date of Patent: Sep. 30, 2008

(54) SYNTHESIS OF DERIVATIVES OF GINKGOLIDE C

(75) Inventors: Koji Nakanishi, New York, NY (US); Stanislav Jaracz, Trinec (CZ); Kristian Stromgaard, Roskilde (DK)

(73) Assignee: The Trustees of Columbia University in the City of New York, New York, NY (US)

( * ) Notice: Subject to any disclaimer, the term of this patent is extended or adjusted under 35 U.S.C. 154(b) by 237 days.

(21) Appl. No.: 10/925,209

(22) Filed: Aug. 24, 2004

(65) Prior Publication Data

US 2005/0119336 A1     Jun. 2, 2005

Related U.S. Application Data

(60) Provisional application No. 60/498,014, filed on Aug. 27, 2003.

(51) Int. Cl.
C07D 305/14 (2006.01)
A01K 43/12 (2006.01)

(52) U.S. Cl. ...................... 549/265; 514/443
(58) Field of Classification Search ................ 549/297, 549/298, 265; 514/461, 468, 338, 443; 546/284.1
See application file for complete search history.

(56) References Cited

U.S. PATENT DOCUMENTS

| | | | |
|---|---|---|---|
| 4,981,688 A | 1/1991 | Ayroles et al. |
| 5,389,370 A | 2/1995 | O'Reilly et al. |
| 5,399,348 A | 3/1995 | Schwabe et al. |
| 5,466,829 A | 11/1995 | Park et al. |
| 5,512,286 A | 4/1996 | Schwabe et al. |
| 5,541,183 A | 7/1996 | Park et al. |
| 5,599,950 A | 2/1997 | Teng |
| 6,030,621 A | 2/2000 | De Long et al. |
| 6,117,431 A | 9/2000 | Ramazanov et al. |
| 6,143,725 A | 11/2000 | Vasella et al. |
| 6,174,531 B1 | 1/2001 | Zhang et al. |
| 6,187,314 B1 | 2/2001 | Xie et al. |
| 6,221,356 B1 | 4/2001 | Junsheng |
| 6,274,621 B1 | 8/2001 | Drieu et al. |

(Continued)

FOREIGN PATENT DOCUMENTS

| | | |
|---|---|---|
| DE | 2117429 | 10/1972 |
| GB | 2288599 A | 11/1995 |
| WO | WO9302204 | 2/1993 |
| WO | WO 99/52911 | 10/1999 |
| WO | WO 02/083158 | 10/2002 |
| WO | WO 03/006040 A1 | 1/2003 |
| WO | WO 03/082185 A1 | 10/2003 |
| WO | WO2005021496 | 3/2005 |
| WO | WO2005046829 | 5/2005 |
| WO | WO2005092324 | 10/2005 |
| WO | WO2006083366 | 8/2006 |
| WO | WO2007002410 | 1/2007 |

OTHER PUBLICATIONS

McKenna, DJ et al, Efficacy, safety, and use of *Ginkgo biloba* in clinical and preclinical applications, PMID 11565403 (2001).*

(Continued)

*Primary Examiner*—D. Margaret Seaman
*Assistant Examiner*—Nizal S Chandrakumar
(74) *Attorney, Agent, or Firm*—John P. White; Cooper & Dunham LLP

(57) ABSTRACT

The subject invention provides ginkgolide C derivatives compounds having the structure:

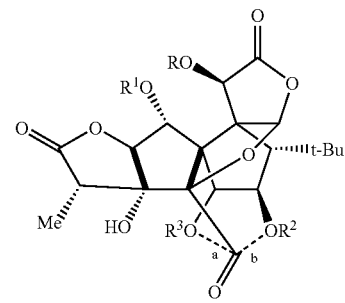

wherein R is H or -A-Ar,
  where A is an alkyl group; and
  Ar is an aryl group, which may contain heteroatoms and may be unsubstituted or substituted by one to five substituents each selected from the group consisting of hydrogen, alkoxy, $-CH_2CO_2R^4$, and $-CH_2CONR^5R^6$;
    where $R^4$ is an alkyl group; and
    $R^5$ and $R^6$ are each, independently, hydrogen or a branched or unbranched alkyl group;
wherein $R^1$ is H or $-COR^7$,
  where $R^7$ is alkyl, aryl or amino;
wherein $R^2$ is present or absent, and when present is H, $-COR^8$ or $-CO-Z-R^8$;
  where $R^8$ is alkyl, aryl or amino; and
  Z is oxygen;
wherein $R^3$ is present or absent, and when present is $-COR^9$;
  where $R^9$ is alkyl or aryl;
wherein only one of $R^2$ or $R^3$ is present in the compound;
wherein only two of R, $R^1$, $R^2$ and $R^3$ are H; and
wherein each of a and b designates a single covalent bond which is present or absent,
  where bond a is present when $R^3$ is absent and bond b is present when $R^2$ is absent;
or an optically pure enantiomer of the compound. Additionally, the subject invention provides methods of inhibiting the activity of a glycine receptor using these compounds.

29 Claims, 3 Drawing Sheets

U.S. PATENT DOCUMENTS

| | | | |
|---|---|---|---|
| 6,328,999 | B1 | 12/2001 | Schwabe et al. |
| 6,590,109 | B2 | 7/2003 | Lichtblau et al. |
| 6,693,091 | B2 | 2/2004 | Stromgaard et al. |
| 6,844,451 | B2 | 1/2005 | Lichtblau et al. |
| 7,145,021 | B2 | 12/2006 | Stromgaard et al. |
| 2003/0194370 | A1 | 10/2003 | Lichtlbau et al. |
| 2003/0225052 | A1* | 12/2003 | Stromgaard et al. ......... 514/183 |
| 2005/0136136 | A1 | 6/2005 | Lichtblau et al. |

OTHER PUBLICATIONS

Ahlemeyer, B et al, Pharmacological studies supporting the therapeutic use of *Ginkgo biloba* extract for Alzheimer's disease, PMID: 13130383 (2003).*
Jaracz et al. Journal of Organic Chemistry, 2002 67, 4623-4626; Published on the Web May 29, 2002.*
Vogensen et al..Journal of Medicinal Chemistry, 2003, 46, 601-608, published 02/13/200, p. 604.*
Tanaka, K. et al. (2005) "Unique Reactivity of α-Alkoxy Ginkgolide Lactones to Nucleophilic Reagents: Preparation of New Lactol Derivatives", Bull. Chem. Soc. Jpn., 78:1843-1850.
Tanaka, K. et al. (2005) "Preparation of Ginkgolide and F-seco-ginkgolide Lactols: the Unique Reactivity of α-hydroxy Lactones toward $NaBH_4$", Tetrahedron Letters, 46:531-534.
Vogensen, S.B. et al. (2003) "Preparation of 7-Substituted Ginkgolide Derivatives: Potent Platelet Activating Factor (PAF) Receptor Antagonists", J. Med. Chem., 46:601-608.
International Search Report issued on Mar. 22, 2007 in connection with PCT/US05/42647.
Written Opinion of the International Searching Authority issued on Mar. 22, 2007 in connection with PCT/US05/42647.
U.S. Appl. No. 11/634,429, filed Dec. 5, 2006 (Kristian Stromgaard et al.).
Ahlemeyer, B. et al. (2003) PMID: 13130383.
Lang, Q. et al. (2001) *Talanta* 54:673-680.
McKenna, D.J. et al., (2001) Efficacy, Safety and Use of *Gingko biloba* in Clinical and Preclinical Applications, Abstract; *Altern. Ther. Health. Med.*, 7(5):70.
Supplementary European Search Report issued Sep. 30, 2005 in connection with Application No. 02748132.4.
International Search Report issed Jun. 8, 2005 in connection with Application No. PCT/US04/037412.
International Search Report issued Jan. 3, 2007 in connection with Application No. PCT/US06/24492.
Written Opinion of the International Searching Authority issued by the International Searching Authority (ISA/US) on Jun. 8, 2005 in connection with Application No. PCT/US04/037412.
U.S. Appl. No. 10/401,931, filed Mar. 28, 2003.
Jaracz et al. "Ginkgolides: Selective Acetylations, Translactonization, and Biological Evaluation", J. Org. Chem 67(13):4623-4626 (2002).
International Search Report issued Mar. 17, 2005 in connection with PCT/US04/27671.
PCT/US02/22101 International Search Report, issued Sep. 12, 2002.
PCT/US02/22101 International Preliminary Examination Report, issued Apr. 21, 2003.
PCT/US03/12651 International Search Report, issued Sep. 2, 2003.
Corey, E.J. & Su, W.G. (1987) J. Am. Chem. Soc. 109, 7534-7536.
Corey, E.J., Kang, M.C., Desai, M.C., Ghosh, A.K., & Houpis, I.N. (1988) J. Am. Chem. Soc. 110, 649-651.
Corey, E.J. & Ghosh, A.K. (1988) Tetrahedron Lett. 29, 3205-3206.
Cory, E.J. & Gavai, A.V. (1989) Tetrahedron Lett. 30, 6959-6962.
Corey, E.J. Rao, K.S. (1991) Tetrahedron Lett. 32, 4623-4626.
Hu, L., Chen, Z., Cheng, X., & Xie, Y. (1999) Pure Appl. Chem. 71, 1153-1156.
Hu, L., Chen, Z., Xie, Y., Jiang, H., & Zhen, H. (2000) Bioorg. Med. Chem. 8, 1515-1521.
Hu, L., Chen, Z., Xie, Y., Jiang, Y., & Zhen, H. (2000) J. Asian Nat. Prod. Res. 2, 103-110.
Hu, L., Chen, Z., & Xie, Y. (2001) J. Asian Nat. Prod. Res. 3, 219-227.
WO/2007/002410 published Jan. 4, 2007 (PCT International Application No. PCT/US2006/024492).
WO/2006/083366 published Aug. 10, 2006 (PCT International Application No. PCT/US2005/042647).
International Search Report issued Jan. 3, 2007 in PCT International Application No. PCT/US2006/024492 (WO/2007/002410).
International Search Report issued Mar. 22, 2007 in connection with PCT/US2005/042647 (WO 2006/083366).
Written Opinion issued Mar. 22, 2007 in connection with PCT/US2005/042647 (WO 2006/083366).
International Preliminary Examination Report issued on May 30, 2007 in connection with PCT/US2005/042647 (WO 2006/083366).
Tanaka, K. et al. (2005) "Unique Reactivity of α-Alkoxy Ginkgolide Lactones to Nucleophilic Reagents: Preparation of New Lactol Derivatives", Bull. Chem. Soc. Jpn., 78:1843-1850.
Tanaka, K. et al. (2005) "Preparation of Ginkgolide and F-seco-ginkgolide Lactols: the Unique Reactivity of α-hydroxy Lactones toward NaBH4", Tetrahedron Letters, 46:531-534.
Vogensen, S.B. et al. (2003) "Preparation of 7-Substituted Ginkgolide Derivatives: Potent Platelet Activating Factor (PAF) Receptor Antagonists", J. Med. Chem., 46:601-608.
U.S. Appl. No. 09/903,049, filed Jul. 11, 2001.
U.S. Appl. No. 11/791,422, filed Nov. 23, 2005.
Office Action issued Nov. 14, 2007 in connection with U.S. Appl. No. 11/634,429.
Notification Concerning Transmittal of International Preliminary Report on Patentability issued Jan. 10, 2008 in connection with PCT/US2006/024492.

* cited by examiner

Ginkgolides A, B, C, J, and M.

10-Alkyl-iso-GC-1,6-bisacetates

18 (R= CH$_2$COOMe)
19 (R = H)
20 (R = OMe)

Benzoates of ginkgolide C.

SYNTHESIS OF DERIVATIVES OF GINKGOLIDE C

This application claims the benefit of U.S. Provisional Application No. 60/498,014, filed Aug 27, 2003, the contents of which are hereby incorporated by reference.

This invention has been made with government support under National Institutes of Health grant MH068817. Accordingly, the U.S. Government has certain rights in the invention.

Throughout this application various publications are referenced in parenthesis. The disclosures of these publications in their entireties are hereby incorporated by reference into this application in order to more fully describe the state of the art to which this invention pertains.

BACKGROUND OF THE INVENTION

The *Ginkgo biloba* tree is among the oldest living plants and is referred to as a "living fossil". It was introduced into the Western world in the 18th century and admired for its unique beauty, especially the leaves, as exemplified by a 1815 poem by Wilhelm von Goethe referring to its beauty (Goethe, 1819). The Ginkgo tree has a long history of use in traditional Chinese medicine, but it was not until the 1960's that a standardized extract of *G. biloba* leaves, EGb 761, was introduced into the European markets (Defeudis, 1998). Today *G. biloba* extract is one of the most popular botanical medicines worldwide.

Numerous beneficial effects of EGb 761 has been postulated including improving neuroprotection in Alzheimer's disease. Alzheimer's disease is a progressive, inexorable loss of cognitive function associated with an excessive number of senile plaques in the cerebral cortex and subcortical gray matter, which also contains β-amyloid and neurofibrillary tangles consisting of tau protein. The cause of Alzheimer's disease is not known (Merck Manual, 1999).

EGb 761 has also been postulated in improving peripheral vascular function, inhibition of thrombosis and embolism cognitive disorders, anti-inflammatory and antiproliferative activities, as well as antioxidant activities (Defeudis, 2000). EGb 761 is a complex mixture of compounds, the main ingredients being flavonoids and terpene trilactones (ginkgolides and bilobalide) that comprise 24% and 6%, respectively, of the total extract (Ahlemeyer, 1998; Drieu, 1986). It is considered that the flavonoids act as antioxidants, while the terpene trilactones are involved in anti-inflammation and prevention of blood clotting associated with the antagonistic activity at the platelet-activating factor (PAF) receptor (McKenna, 2001). However, the neuroprotective effects of EGb 761 have so far not been associated with specific components of the extract (Peskind, 1998; Simonson, 1998).

The terpene trilactones, the ginkgolides (FIG. 1) and bilobalide, are unique components of EGb 761, the structures of which were elucidated in 1967 (Maruyama, 1967; Maruyama, 1967; Maruyama, 1967; Maruyama, 1967; Woods, 1967; Nakanishi, 1967; Okabe, 1967). The ginkgolides are diterpene trilactones with a cage-like skeleton consisting of six 5-membered rings, i.e., a spiro[4.4] nonane carbocyclic ring, three lactones, and a tetrahydrofuran moiety. Terpene trilactones from *G. biloba* are also among the very few natural products containing a tert-butyl group.

In contrast to many studies on the neuroprotective effects of EGb 761, the ginkgolides have not been extensively studied partly due to limited availability of pure ginkgolides. The finding in 1985 that ginkgolide B (GB, 2) was a potent antagonist of the PAF receptor (PAFR) (Braquet, 1986; Braquet, 1985) led to extensive structure-activity relationship (SAR) studies on this receptor (Rapin, 1998; Braquet, 1987; Braquet, 1991; Hu, 2001; Hu, 2000; Hu, 2000; Corey, 1991; Park, 1993; Park, 1995; Stromgaard, 2002). However, the significance of these effects in relation to the neuroprotective effects of EGb 761 is not clear (Stromgaard, 2003).

The first indication of a direct interaction of ginkgolides with important targets in the brain was discovered when ginkgolides were shown to be potent and highly selective antagonists of the inhibitory glycine receptor (GlyR) (Stromgaard, 2003; Kondratskaya, 2002). The GlyR is a ligand-gated ion channel found primarily in spinal cord and brain stem, but also in higher brain regions such as hippocampus and developing cortex that consists of $\alpha 1$-$\alpha 4$ and $\beta$ subunits (Betz, 2001). Only a few ligands for GlyRs have been available, the classical example being the convulsant strychnine, a competitive antagonist. However, since the neuropharmacology and functional importance of GlyRs in higher brain regions is not well characterized (Chattipakorn, 2002) new potent and selective ligands are needed for further investigations of the GlyR.

The introduction of combinatorial chemistry and application of related techniques such as parallel or split-and-pool synthesis, solid and solution-phase strategies have opened avenues to libraries of various compounds (Marcaurelle, 2002; Arya, 2001; Ganesan, 2002; Abel, 2002; Krchnak, 2002; Schreiber, 2000). These compounds could be entirely artificial or derivatives of natural products with possible enhanced bioactivities. Recently diversity-oriented semi-synthetic methods have been used for the preparation of library of natural product derivatives for biological activity studies (Abel, 2002). In the following we describe a parallel solution-phase synthesis of a ginkgolide combinatorial library. Diversity is achieved by modification of traditional synthetic methods to prepare novel ginkgolide derivatives in a selective fashion. The ginkgolide derivatives have been evaluated as antagonists of the GlyR using a fluorescence-based high-throughput screening assay.

SUMMARY OF THE INVENTION

The subject invention provides compounds having the structure:

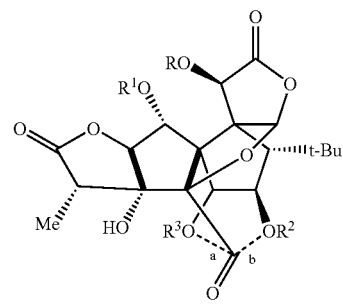

wherein R is H or -A-Ar,
where A is an alkyl group; and
Ar is an aryl group, which may contain heteroatoms and may be unsubstituted or substituted by one to five substituents each selected from the group consisting of hydrogen, alkoxy, —$CH_2CO_2R^4$, and —$CH_2CONR^5R^6$;
where $R^4$ is an alkyl group; and R[5] and R[6] are each, independently, hydrogen or a branched or unbranched alkyl group;

wherein R[1] is H or —COR[7],
where R[7] is alkyl, aryl or amino;

wherein R[2] is present or absent, and when present is H, —COR[8] or —CO-Z-R[8];
where R[8] is alkyl, aryl or amino; and
Z is oxygen;

wherein R[3] is present or absent, and when present is —COR[9];
where R[9] is alkyl or aryl;

wherein only one of R[2] or R[3] is present in the compound;

wherein only two of R, R[1], R[2] and R[3] are H; and wherein each of a and b designates a single covalent bond which is present or absent,
where bond a is present when R[3] is absent and bond b is present when R[2] is absent;

or an optically pure enantiomer of the compound.

The invention also provides a method of inhibiting the activity of a glycine receptor comprising contacting the glycine receptor with the compound having the structure

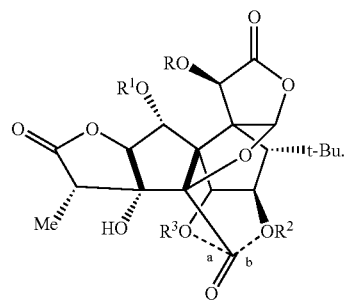

The invention further provides a method of treating Alzheimer's disease in a subject in need of such treatment, comprising administering to the subject a compound having the structure

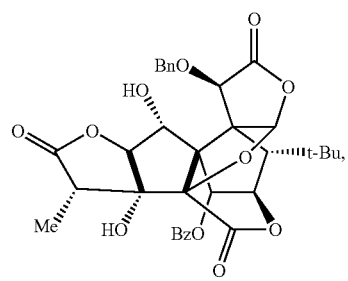

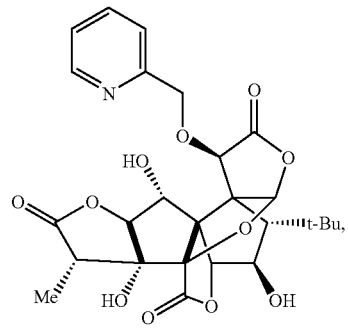

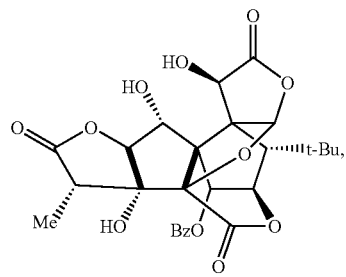

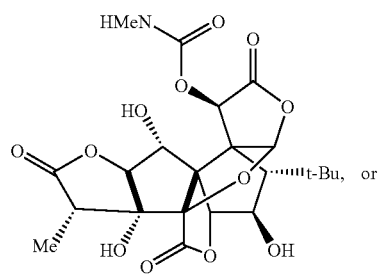

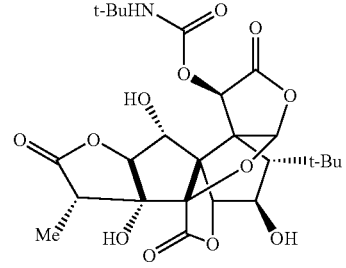

The subject invention also provides a pharmaceutical composition comprising a compound having the structure

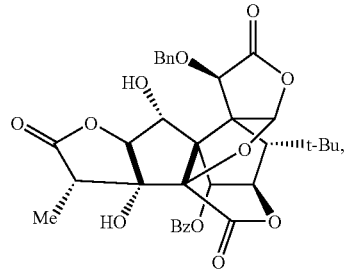

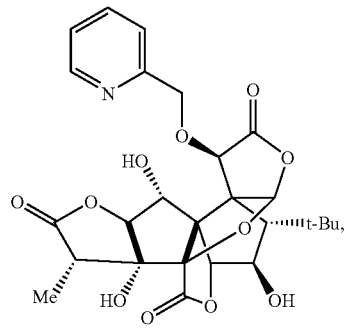

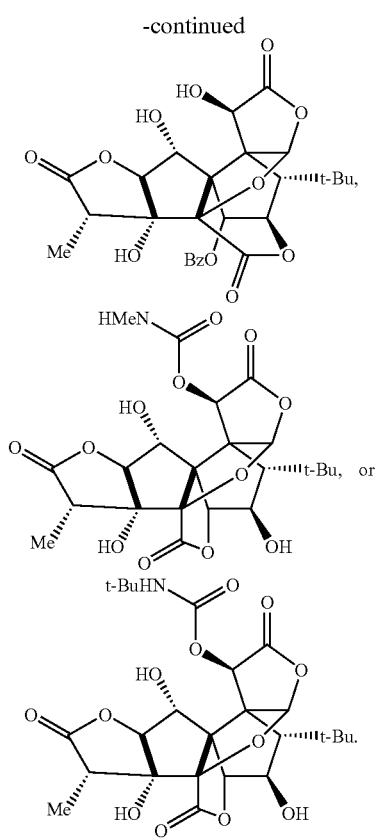

The subject invention also provides a process of preparing the compound having the structure

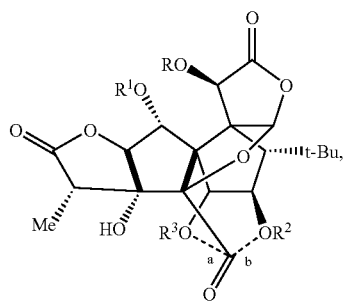

comprising the step of reacting a compound having the structure

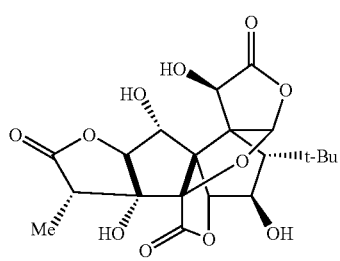

with an electrophile to form the above-indicated compound.

The subject invention still further provides a compound having the structure

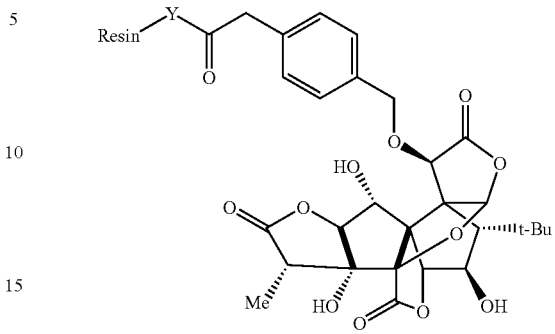

wherein Y is oxygen or —NH—.

DETAILED DESCRIPTION OF THE INVENTION

Figure 1:
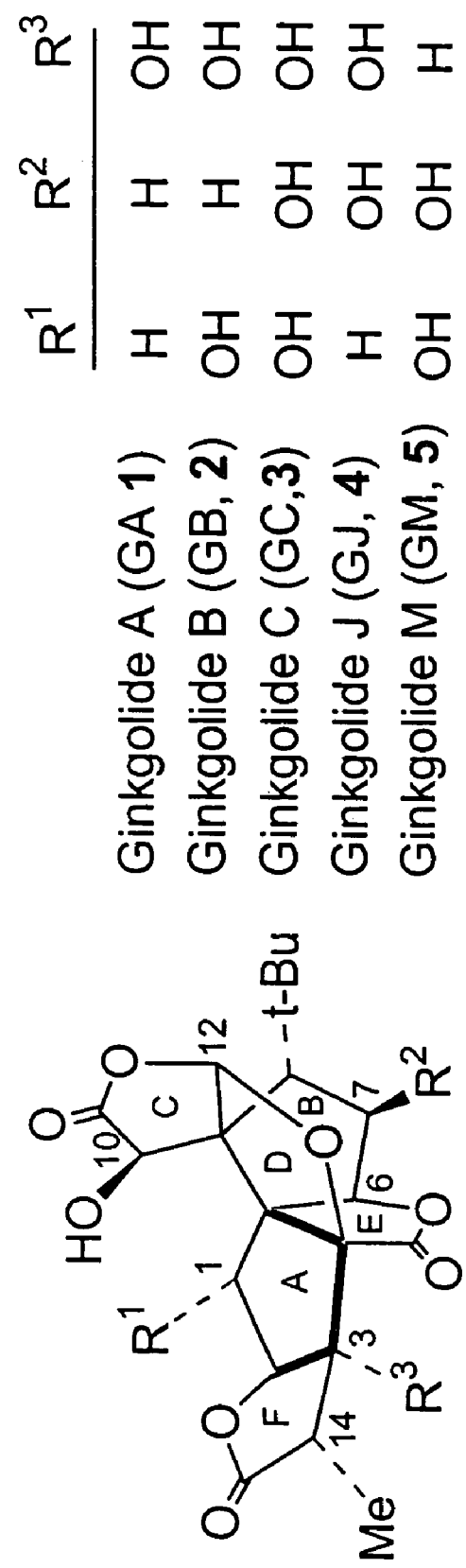
FIG. 1. Ginkgolides A, B, C, J, and M.

The subject invention provides compounds having the structure:

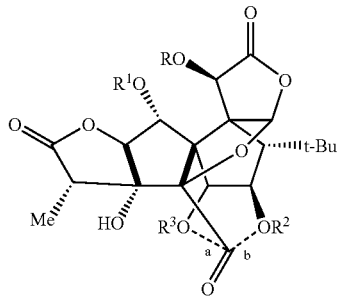

wherein R is H or -A-Ar,
  where A is an alkyl group; and
  Ar is an aryl group, which may contain heteroatoms and may be unsubstituted or substituted by one to five substituents each selected from the group consisting of hydrogen, alkoxy, —$CH_2CO_2R^4$, and —$CH_2CONR^5R^6$;
    where $R^4$ is an alkyl group; and
    $R^5$ and $R^6$ are each, independently, hydrogen or a branched or unbranched alkyl group;
wherein $R^1$ is H or —$COR^7$,
  where $R^7$ is alkyl, aryl or amino;
wherein $R^2$ is present or absent, and when present is H, —$COR^8$ or —CO-Z-$R^8$;
  where $R^8$ is alkyl, aryl or amino; and
  Z is oxygen;
wherein $R^3$ is present or absent, and when present is —$COR^9$;
  where $R^9$ is alkyl or aryl;
wherein only one of $R^2$ or $R^3$ is present in the compound;
wherein only two of R, $R^1$, $R^2$ and $R^3$ are H; and
wherein each of a and b designates a single covalent bond which is present or absent, where bond a is present when $R^3$ is absent and bond b is present when $R^2$ is absent;
or an optically pure enantiomer of the compound.

In one embodiment, the compound has the structure

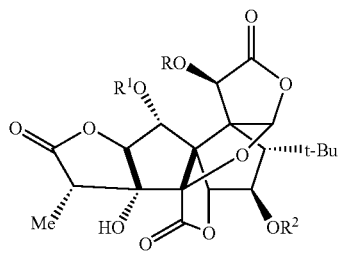

In another embodiment, the compound has the structure

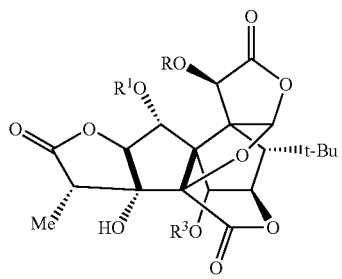

In a further embodiment, the compound has the structure

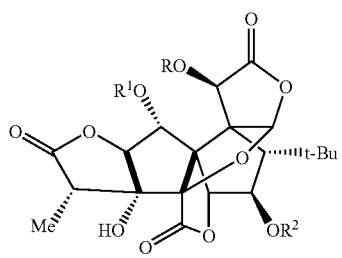

wherein R is H or -A-Ar-;
where A is —$CH_2$—,
Ar is a phenyl group or a picolyl group, either of which may be substituted or unsubstituted by a substituent selected from the group consisting of hydrogen, methoxy, —$CH_2CO_2Me$, and —$CH_2CONH_2$;

In another embodiment, R is H, benzyl, para-methoxybenzyl or picolyl.

In one embodiment, the compound has the structure:

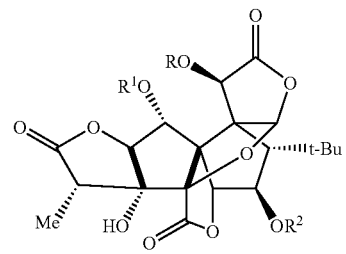

wherein $R^1$ is H or —$COR^7$;
where $R^7$ is methyl, phenyl or —$NR^5R^6$;
where $R^5$ and $R^6$ are each, independently, hydrogen, methyl, or t-butyl, or wherein $R^5$ and $R^6$ together with the nitrogen to which they are attached form a morpholine or piperidine.

In a further embodiment, $R^1$ is H, benzoyl, —COMe, —CONHMe, —CONHtBu, piperidyl, or morpholinyl.

In yet another embodiment, the compound has the structure

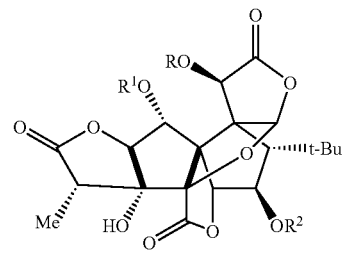

wherein $R^2$ is H, —$COR^8$ or CO-Z-$R^8$;
where $R^8$ is —$NR^5R^6$ or phenyl, which may be unsubstituted or substituted by one to five substituents which are each, independently, halogen or —$NO_2$.
where $R^5$ and $R^6$ are each, independently, hydrogen, methyl, or t-butyl, or wherein $R^5$ and $R^6$ together with the nitrogen to which they are attached together form a morpholine or piperidine.

In yet a further embodiment, $R^2$ is H, benzoyl, —COMe, —$CO_2C_6H_4NO_2$, —CONHMe, —CONHtBu, piperidyl or morpholinyl.

In still another embodiment, the compound has the structure

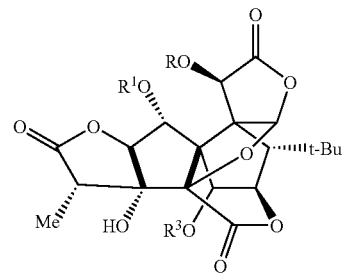

wherein R is H or -A-Ar—;

where A is —CH$_2$—,

Ar is a phenyl group or a picolyl group, either of which may be substituted or unsubstituted by a substituent selected from the group consisting of hydrogen, methoxy, —CH$_2$CO$_2$Me, and —CH$_2$CONH$_2$.

In one embodiment, R is H, benzyl, p-methoxybenzyl or picolyl.

In yet another embodiment, the compound has the structure

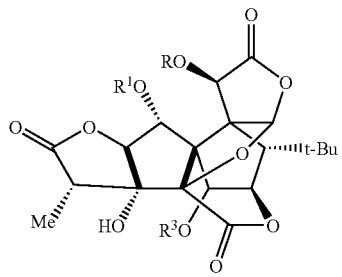

wherein R$^1$ is H or —COR$^7$,
where R$^7$ is methyl, phenyl or —NR$^5$R$^6$;
where R$^5$ and R$^6$ are each, independently, hydrogen, methyl, or t-butyl, or wherein R$^5$ and R$^6$ together with the nitrogen to which they are attached together form a morpholine or piperidine.

In a further embodiment, R$^1$ is H, phenyl, —COMe, —CONHMe, —CONHtBu, —CONC$_5$H$_{10}$ or CONC$_4$H$_8$O.

In a yet further embodiment the compound has the structure

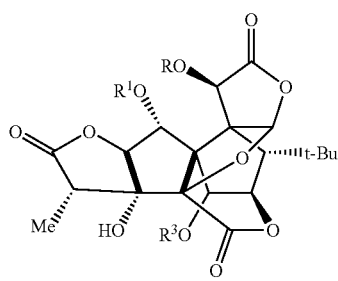

wherein R$^3$ is benzoyl, —COMe or —CO$_2$C$_6$H$_4$NO$_2$.

In another embodiment, the compound has the structure

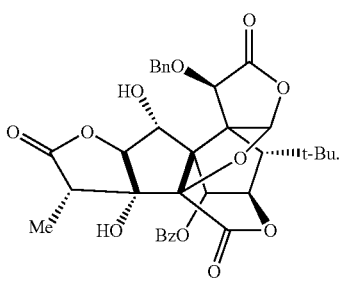

In an even yet further embodiment, the compound has the structure

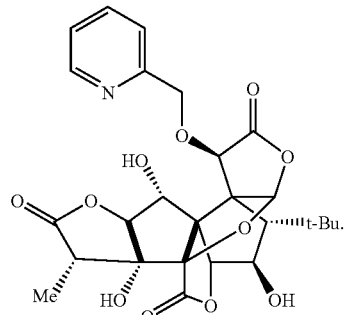

In still yet another embodiment, the compound has the structure

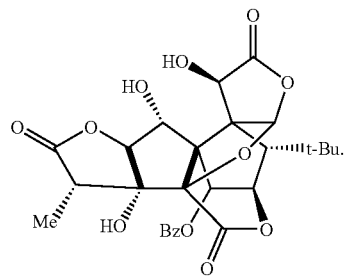

In yet another embodiment, the compound has the structure

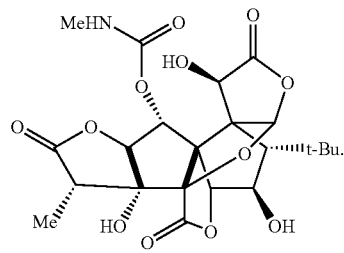

In still another embodiment, the compound has the structure

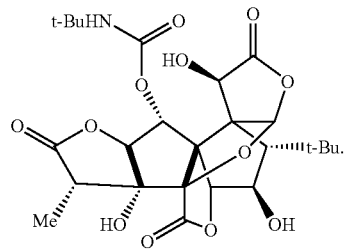

In yet another embodiment, the compound has the structure

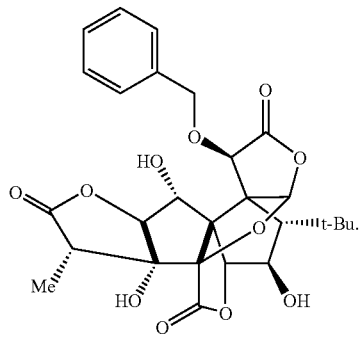

In still another embodiment, the compound has the structure

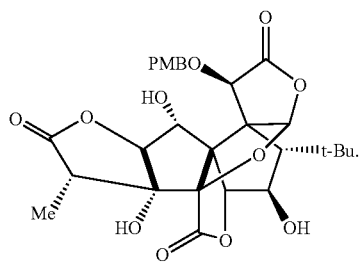

The invention also provides a method of inhibiting the activity of a glycine receptor comprising contacting the glycine receptor with the compound having the structure

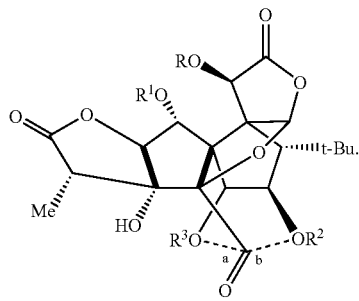

In another embodiment of the method, the compound has the structure

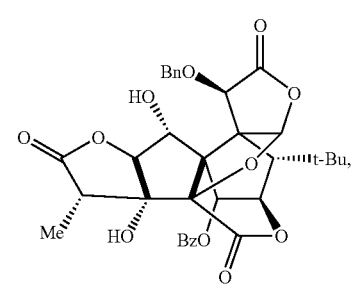

-continued

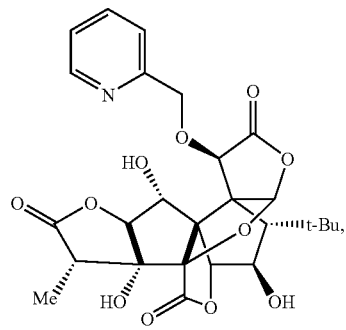

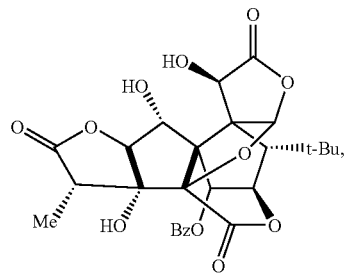

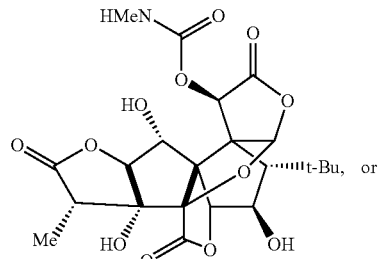

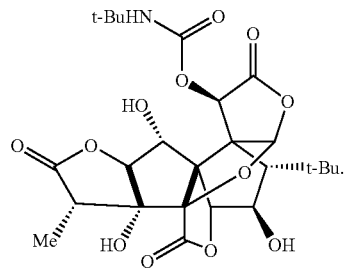

The invention further provides a method of treating Alzheimer's disease in a subject in need of such treatment, comprising administering to the subject a compound having the structure

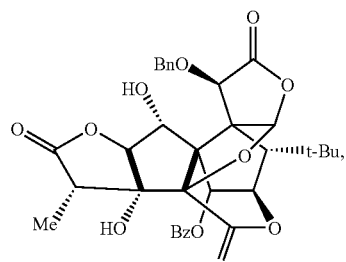

-continued
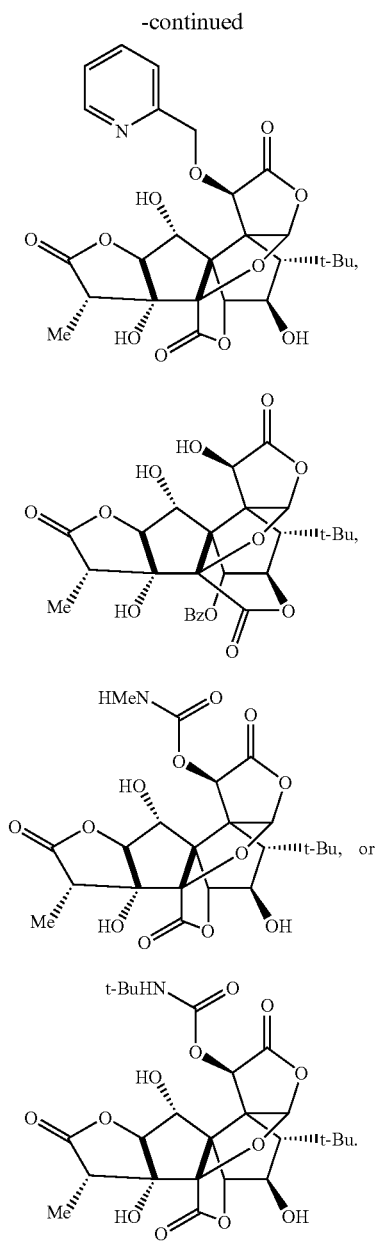
The subject invention also provides a pharmaceutical composition comprising a compound having the structure
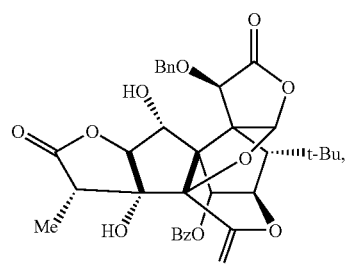
-continued
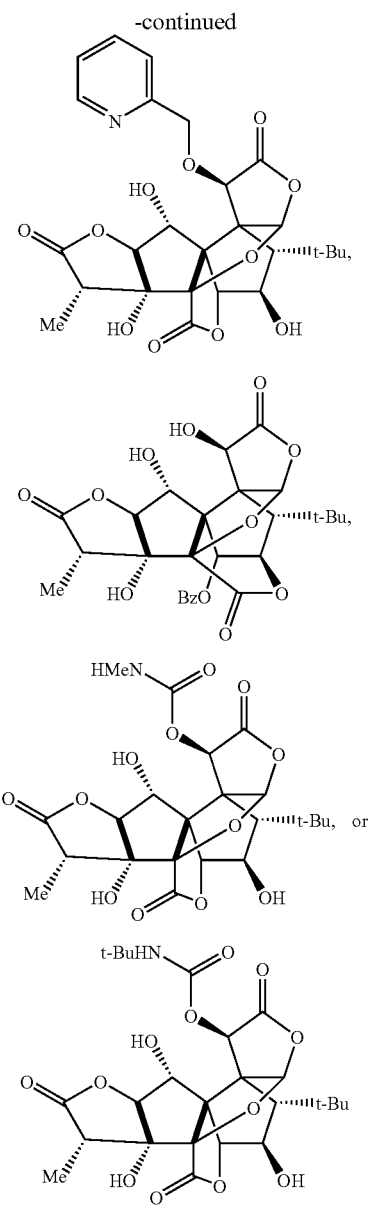
and a pharmaceutical carrier.
The subject invention also provides a process of preparing the compound having the structure
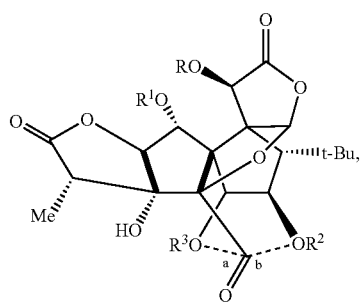

comprising the step of reacting a compound having the structure

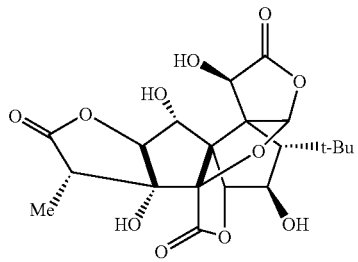

with an electrophile to form the above-indicated compound.

In another embodiment, the process provides the compound having the structure

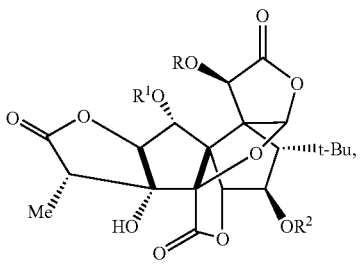

comprising the steps of:
i) reacting a compound having the structure

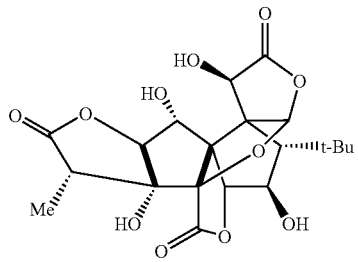

with either 4-methoxybenzyl chloride or benzyl chloride, and a suitable base to form a compound having the structure

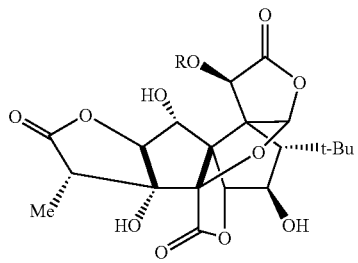

wherein R is benzyl or p-methoxybenzyl; and
ii) reacting the product of step i) with an electrophilic reagents to form the above-indicated compound.

The subject invention even further provides a process of preparing the compound having the structure

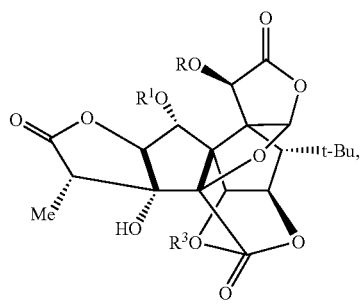

comprising the steps of:
i) reacting a compound having the structure

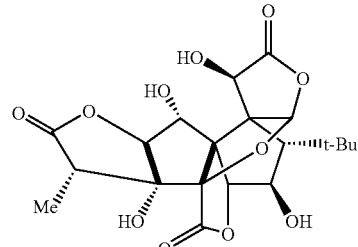

with 4-methoxybenzyl chloride or benzyl chloride, and a suitable base to form a compound having the structure

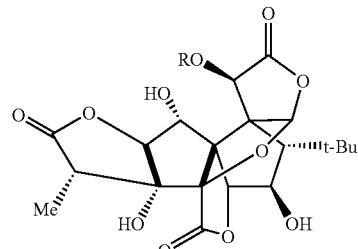

wherein R is benzyl or p-methoxybenzyl; and
ii) reacting the product of step i with the appropriate electrophilic reagents to form the above-indicated compound.

The subject invention still further provides a process of preparing the compound having the structure

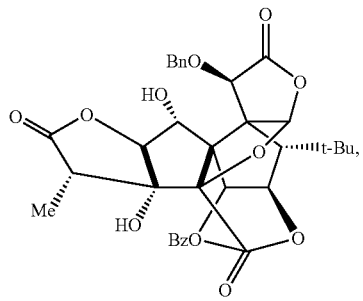

comprising the steps of:
i) reacting a compound having the structure

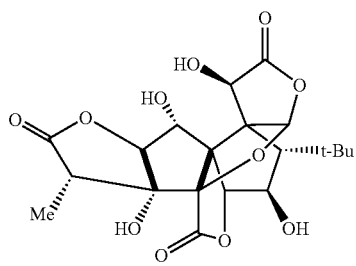

in dimethylformamide with a resin and an appropriate base to form a compound having the structure

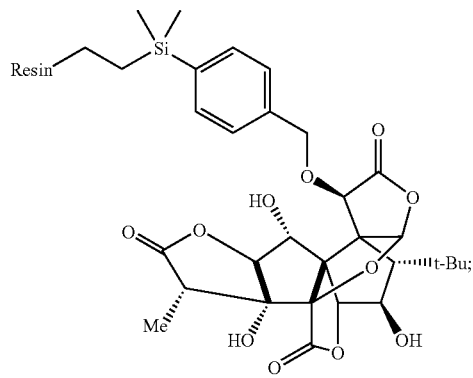

ii) cleaving the product of step i) from the resin by mixing the product of step i) with trifluoracetic acid in a polar solvent to form a compound having the structure

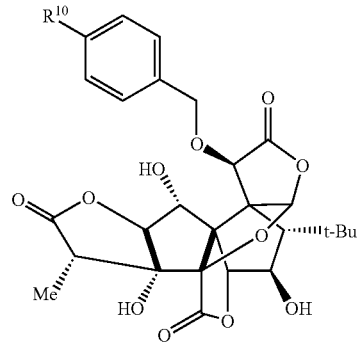

wherein $R^{10}$ is —H, —CH$_2$CO$_2$H or CH$_2$CONH$_2$; and
iii) dissolving the product of step ii) and a suitable amine base in an appropriate solvent and reacting with benzoic anhydride, thereby forming the above-indicated compound.

The subject invention yet even further provides a process of preparing the compound having the structure

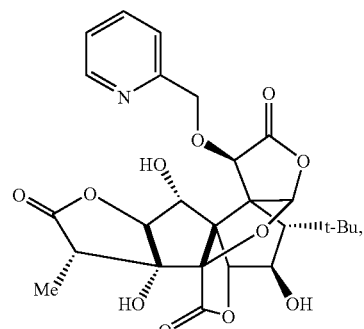

comprising the step of reacting a compound having the structure

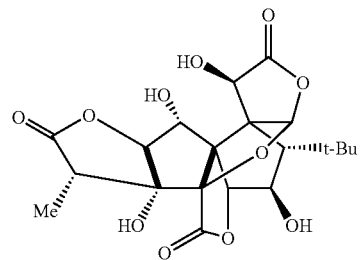

with 2-picolyl chloride in a polar solvent with a suitable base, thereby forming the above-indicated compound.

The subject invention provides a process of preparing the compound having the structure

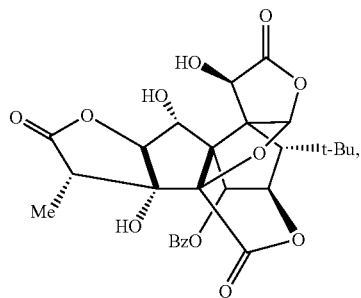

comprising the steps of:
i) reacting a compound having the structure

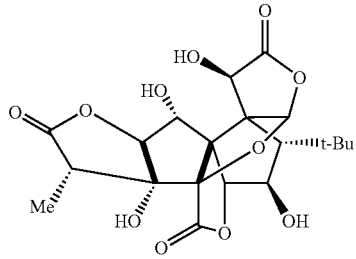

with 4-methoxybenzyl chloride in a polar solvent with a suitable base, providing a compound having the structure

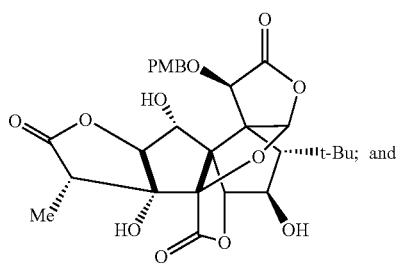

ii) dissolving the product of step i) and a suitable amine base in a polar solvent and reacting with benzoic anhydride, thereby forming the above-indicated compound.

The subject invention still further provides a process of preparing the compound having the structure

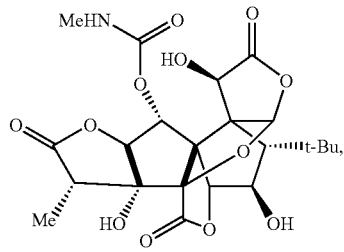

comprising the steps of:
i) reacting a compound having the structure

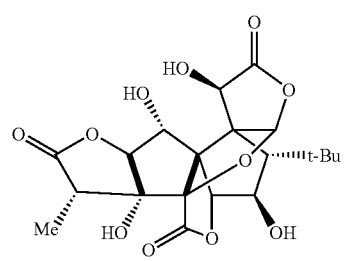

with 4-methoxybenzyl chloride in an appropriate polar solvent with a suitable base, providing a compound having the structure

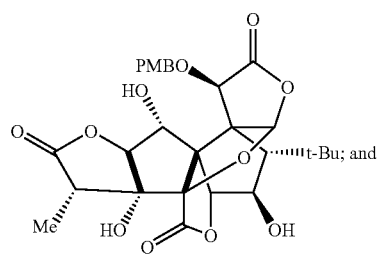

and
ii) dissolving the product of step i) and iPr$_2$EtN base in a suitable solvent and reacting with p-nitrophenyl chloroformate and then with MeNH$_2$, forming a compound having the structure

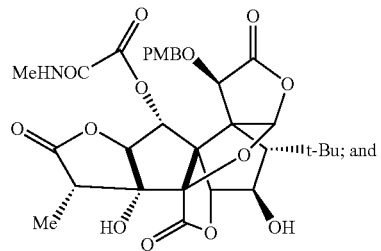

iii) dissolving the product of step ii) in a suitable solvent and reacting with (NH$_4$)$_2$Ce(NO$_3$)$_6$, thereby forming the above-indicated compound.

The subject invention yet further provides a process of preparing the compound having the structure

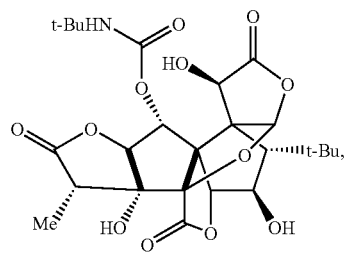

comprising the steps of:
i) reacting a compound having the structure

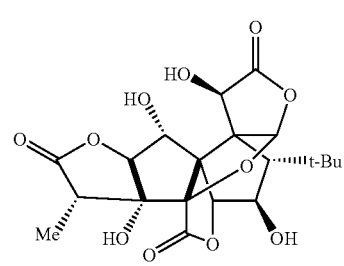

with 4-methoxybenzyl chloride in an a polar solvent with a suitable base, providing a compound having the structure

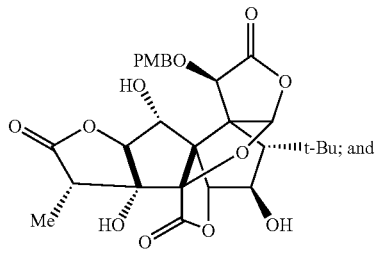

ii) dissolving the product of step i) and iPr$_2$EtN base in a suitable solvent and reacting with p-nitrophenyl chloroformate and then with tBuNH$_2$, thereby forming the product

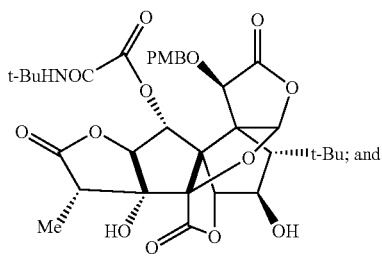

iii) dissolving the product of step ii) in a suitable solvent and reacting with (NH$_4$)$_2$Ce(NO$_3$)$_6$, thereby forming the above-indicated compound.

The subject invention still further provides a compound having the structure

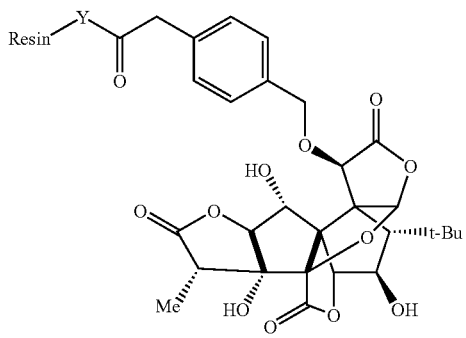

wherein Y is oxygen or —NH—.

Experimental Details

Materials and Methods. All reactions were performed under argon at ambient temperature in dry solvents and yields refer to isolated products, unless otherwise stated. GC (3) originated from early structural studies (Maruyama, 1967; Maruyama, 1967; Maruyama, 1967; Maruyama, 1967; Woods, 1967), and was recrystalized from ethanol/water and dried in dessicator. All other reagents were purchased and used as received. Polystyrene resin, Wang resin and bromopolystyrene resin were obtained from Advanced ChemTech, DES resin and sulfonyl chloride resin were obtained from Aldrich, Tentagel® resin was purchased from Rapp-Polymere Gmbh. Reactions were monitored by analytical TLC with silica gel 60 F$_{254}$ and spots were visualized by heating and UV light (254 nm). Flash chromatography was performed using silica gel (230-400 mesh).

$^1$H-NMR and $^{13}$C-NMR spectra were recorded with Bruker (300, 400 or 500 MHz) spectrometers. The chemical shifts are expressed in ppm (δ)downfield from tetramethylsilane (in CDCl$_3$) or calibrated according to residual solvent peak as an internal standard (DMSO-d$_6$, δ 2.50, MeOD, δ 3.30). Assignment of peaks was achieved using 2D methods (COSY), by comparison with published data where available and comparison with $^1$H-NMR spectra of parent ginkgolides. In certain cases, HSQC was used instead of $^{13}$C-NMR. High-resolution mass spectra (HRMS) were measured on JEOL JMS-HX110/100A HF mass spectrometer under FAB conditions with NBA as the matrix. In general, all ginkgolide derivatives decomposed above 250° C.

| Abbreviations | |
|---|---|
| Ac = | CH$_3$CO |
| Bn = | —CH$_2$C$_6$H$_5$ |
| Bz = | —COC$_6$H$_5$ |

Synthesis

Representative procedure for attachment of GC (3) to polystyrene resin with silyl linker. To a chlorodiethylsilylpolystyrene resin (100 mg, 0.052 mmol) in glass vial with PTFE septa in the stopper was added a solution of GC (3, 45.8 mg, 0.104 mmol, 2 equiv), iPr$_2$EtN (18.2 mL, 0.104 mmol, 2 equiv) and dimethylaminopyridine (DMAP, 1.3 mg, 0.01 mmol, 0.2 equiv) in THF/CH$_2$Cl$_2$ (1:1, 0.52 mL). The reaction mixture was agitated gently on a rotary shaker at ambient temperature for 24 h and then filtered and washed with CH$_2$Cl$_2$ (3×2 mL) and THF (3×2 mL) alternately, then with Et$_2$O (2×2 mL) and dried under high vacuum.

7-pipsyl-GC (6). To a suspension of GC (3, 99.8 mg, 0.227 mmol) and 4-iodobenzenesulfonyl chloride (205.7 mg, 0.680 mmol, 3 equiv) in CH$_2$Cl$_2$ (2.25 mL) was added pyridine (73 mL, 0.906 mmol, 4 equiv) and the reaction mixture was stirred for 26 h. The solvent was removed under reduced pressure, the residue dissolved in EtOAc and washed with 1M aq. HCl, brine and dried with MgSO$_4$. The crude product was purified by flash column chromatography (gradient 40-99% EtOAc/hexanes, 1% AcOH) to obtain 113.8 mg of pure 6 (73% yield) and 24.3 mg of recovered GC (25%). $^1$H-NMR (400 MHz, DMSO-d$_6$) δ 8.18-8.10 (m, 2H$_{AR}$), 7.78-7.70 (m, 2H$_{AR}$), 7.57 (d, J=5.5 Hz, 1H, 10-H), 6.52 (s, 1H, 3-OH), 6.13 (s, 1H, 12-H), 5.30 (d, J=4.2 Hz, 1H, 1-OH), 5.16 (d, J=4.1 Hz, 1H, 6-H), 5.01 (d, J=5.5 Hz, 1H, 10-H), 4.85 (dd, J=12.4, 4.1 Hz, 1H, 7-H), 4.60 (d, J=6.5 Hz, 1H, 2-H), 4.09 (dd, J=6.5, 4.2 Hz, 1H, 1-H), 2.80 (q, J=7.1 Hz, 1H, 14-H), 1.95 (d, J=12.4 Hz, 1H, 8-H), 1.10 (d, J=7.1 Hz, 3H, 16-CH$_3$), 0.98 (s, 9H, tBu); $^{13}$C-NMR (75 MHz, MeOD) δ 8.16, 29.24, 33.20, 43.17, 50.03, 64.78, 68.71, 70.24, 75.03, 76.67, 81.10, 84.50, 93.47, 100.06, 103.62, 111.14, 130.49, 137.04, 140.39, 171.66, 174.40, 178.05. HRMS (FAB) calcd for C$_{26}$H$_{28}$O$_{13}$SI 707.0295, found 707.0265.

Attachment of 6 to a resin (7). To a sample tube was added TentaGel® HL-NH$_2$ (93 mg, 42.6 mmol), 6 (30.1 mg, 42.6 mmol, 1 equiv), Et$_3$N (17 mL, 0.122 mmol, 2.9 equiv), Pd(PPh$_3$)$_4$ (1 mg, 0.9 mmol, 0.02 equiv) and DMF (0.626 mL). The tube was placed into autoclave, which was purged with carbon monoxide three times before applying a pressure of 15 atm. After being left at 80-90° C. for 14 h, the resin was transferred into a plastic syringe with porous PE plug and consecutively washed with DMF (3×3 mL), $CH_2Cl_2$ (2×3 mL), DMF (2×3 mL), acetonitrile (2×3 mL), acetonitrile/$H_2O$ (1:1, 4×3 mL), MeOH (3×3 mL), $CH_2Cl_2$ (3×3 mL), and $Et_2O$ (3×3 mL) and dried under vacuum to obtain 7.

Attachment of 4-(bromomethyl)phenylacetic acid to a Wang resin (8). To a solution of 4-(bromomethyl)phenylacetic acid (185.7 mg, 0.811 mmol, 8 equiv) in THF (1.6 mL) was added DIC (127 mL, 0.811 mmol, 8 equiv) and mixture was agitated for 5 min until white crystals developed. More THF (1.6 mL) was added to redissolve the precipitate and the solution was mixed with Wang resin (169 mg, 0.101 mmol, 1 equiv). The reaction mixture was gently agitated on a rotary shaker for 9 h and then filtered, washed with THF (4×5 mL) and $CH_2Cl_2$ (4×5 mL) alternately, then with $CH_2Cl_2$ (2×5 mL), MeOH (2×5 mL) and dried under vacuum to obtain 8.

Attachment of 4-(bromomethyl)phenylacetic acid to a Rink-amide resin (9). To a solution of 4-(bromomethyl)phenylacetic acid (47.4 mg, 0.207 mmol, 8 equiv) in THF (0.4 mL) was added 2-dimethylaminoisopropyl chloride hydrochloride (DIC, 32.4 mL, 0.207 mmol, 8 equiv) and mixture was agitated for 5 min until white crystals developed. More THF (0.6 mL) was added to re-dissolve the precipitate and the solution was mixed with Rink-amide TentaGel® resin (108 mg, 0.026 mmol, 1 equiv). The reaction mixture was gently agitated on a rotary shaker for 2.5 h and then filtered, washed with THF (4×3 mL) and $CH_2Cl_2$ (4×3 mL) alternately, then with $CH_2Cl_2$ (2×3 mL), $Et_2O$ (2×3 mL) and dried under vacuum to obtain 9.

Synthesis of silicon-linked solid-phase anchored benzyl bromide (14). To a solution of 4-(allyldimethylsilyl)benzyl alcohol (475 mg, 2.30 mmol) in THF (4.6 mL) at 0° C. was slowly added 9-borabicyclo[3.3.1]nonane (9-BBN, 9.2 mL, 0.5M in THF, 4.6 mmol, 2 equiv). The reaction mixture was warmed up slowly to room temperature and then stirred for 10 h. To the mixture was then added bromopolystyrene (1.075 g, 1.5 mmol/g, 1.61 mmol, 0.7 equiv), $K_2CO_3$ (2.3 mL, 3M in $H_2O$, 6.9 mmol, 3 equiv), DMF (6.3 mL) and finally $Pd(PPh_3)_4$ (53.3 mg, 0.046 mmol, 0.02 equiv). The resulting suspension was slowly stirred in closed vial at 70-75° C. for 24 h. $Pd(PPh_3)_4$ (53.3 mg, 0.046 mmol, 0.02 equiv) was added to the reaction mixture, which was again reacted at 70-75° C. for additional 24 h. The resin was filtered and washed with DMF (3×), $H_2O$ (3×), DMF (3×), then with $CH_2Cl_2$ (3×) and MeOH (3×) alternately and with MeOH (1×) and dried under high vacuum to obtain 1.265 g of dry resin. The resin (≦1.61 mmol) was placed into solid-phase reactor and $PPh_3$ (846 mg, 3.22 mmol, 2 equiv), $CBr_4$ (1.070 g, 3.22 mmol, 2 equiv) and $CH_2Cl_2$ (16 mL) were added at 0° C. The mixture was agitated on rotary shaker at room temperature for 6 h and then filtered and washed with $CH_2Cl_2$ (3×), then MeOH (2×) and $CH_2Cl_2$ (2×) alternately and then with MeOH (2×) and dried under vacuum to obtain 1.371 g of resin 14. Loading of the resin was determined by cleavage with $Br_2$ to obtain 4-bromobenzyl bromide (1.17 mmol/g, 85% yield from bromopolystyrene).

General procedure for attachment of GC (3) to solid-phase anchored benzyl bromide (10, 11, 15). To a mixture of a resin (8, 9, or 14) (0.1 mmol), GC (3) (79.2 mg, 0.18 mmol, 1.8 equiv) and finely grounded $K_2CO_3$ (41.5 mg, 0.3 mmol, 3 equiv) in a plastic syringe with porous PE plug was added DMF and the suspension was gently agitated on rotary shaker for 30 h. The resin was filtered and washed with DMF (3×) for GC (3) recovery and the resin was further washed with $H_2O$ (3×), DMF (3×), then $CH_2Cl_2$ (3×) and MeOH (3×) alternately and dried under high vacuum. A test for the presence of alkyl halides (using 4-nitrobezylpyridine) was negative (Kuisle, 1999).

Cleavage from Wang resin (12). To a sample of resin 10 (12 mg) in a vial was added TFA/$CH_2Cl_2$ (1:1, 0.2 mL). After standing for 30 min, resin was filtered and washed with TFA/$CH_2Cl_2$ (2:3, 0.17 mL), TFA/$CH_2Cl_2$ (1:3, 0.22 mL), and TFA/$CH_2Cl_2$ (1:4, 0.2 mL). Combined washing solutions were mixed with filtrate and volatiles were removed under reduced pressure. Residue was dissolved in MeOH (0.1 mL) and treated with $CH_2N_2$ (1 mL, ~0.2M in $Et_2O$) for 10 min. Volatiles were removed under reduced pressure to provide 12 (~90% purity based on $^1$H NMR). $^1$H-NMR (400 MHz, $CDCl_3$) δ 7.40-7.30 (m, $4H_{AR}$), 5.99 (s, 1H, 12-H), 5.48 (d, J=9.3 Hz, 1H, benzyl), 5.13 (d, J=4.4 Hz, 1H, 6-H), 4.93 (s, 1H, 10-H), 4.61 (d, J=9.3 Hz, 1H, benzyl), 4.53 (d, J=7.8 Hz, 1H, 2-H), 4.22 (dd, J=3.3, 7.8 Hz, 1H, 1-H), 4.18-4.08 (m, 1H, 7-H), 3.71 (s, 3H, —$OCH_3$), 3.66 (s, 2H, $CH_2$), 3.05 (q, J=7.0 Hz, 1H, 14-H), 2.82 (d, J=3.4 Hz, 1H, 1-OH), 2.73 (bs, 1H, 3-OH), 2.11 (d, J=11.5 Hz, 1H, 7-OH), 1.69 (d, J=12.4 Hz, 1H, 8-H), 1.30 (d, J=7.0 Hz, 3H, 16-$CH_3$), 1.23 (s, 9H, tBu); HRMS (FAB) calcd for $C_{30}H_{35}O_{13}$ 603.2078, found 603.2081.

Cleavage from Rink-amide resin (13). To a sample of resin 11 (27.6 mg) in a vial was added TFA/$H_2O$ (9:1, 0.4 mL). After standing for 50 min, the resin was filtered and washed with TFA/$H_2O$ (9:1, 2×0.28 mL). The combined washing solutions were mixed with filtrate and volatiles were removed under reduced pressure to provide 13 (95% purity based on $^1$H NMR). $^1$H-NMR (400 MHz, DMSO-$d_6$) δ 7.48 (s, 1H, $NH_AH_B$), 7.35-7.28 (m, $2H_{AR}$), 7.28-7.21 (m, $2H_{AR}$), 6.89 (s, 1H, $NH_AH_B$), 6.48 (s, 1H, 3-OH), 6.19 (s, 1H, 12-H), 5.65 (bs, 1H, 7-OH), 5.34 (d, J=10.9 Hz, 1H, benzyl), 5.22 (s, 1H, 10-H), 4.94 (d, J=4.1 Hz, 1H, 6-H), 4.80 (d, J=4.0 Hz, 1H, 1-OH), 4.63 (d, J=10.9 Hz, 1H, benzyl), 4.59 (d, J=6.5 Hz, 1H, 2-H), 4.13 (dd, J=4.0, 6.4 Hz, 1H, 1-H), 3.97 (dd, J=4.1, 12.5 Hz, 1H, 7-H), 3.37 (s, 2H, $CH_2$), 2.84 (q, J=7.1 Hz, 1H, 14-H), 1.55 (d, J=12.5 Hz, 1H, 8-H), 1.14 (d, J=7.1 Hz, 3H, 16-$CH_3$), 1.09 (s, 9H, tBu); HRMS (FAB) calcd for $C_{29}H_{34}O_{12}N$ 588.2081, found 588.2083.

Cleavage from silicone-linker resin (16). To a sample of resin 15 (12.6 mg) in a vial was added TFA/$CH_2Cl_2$ (1:1, 0.5 mL).

After standing for 24 h, resin was filtered and washed with TFA/$CH_2Cl_2$ (1:1, 2×0.3 mL). Combined washing solutions were mixed with filtrate and volatiles were removed under reduced pressure to provide 16 (85% purity based on $^1$H NMR). Analytical data as previously described (Vogensen, 2003).

10-Benzyloxy-GC (16). Synthesis and analytical data as previously described (Vogensen, 2003).

10-Benzyloxy-isoGC-6-benzoate (17). To a solution of 16 (18.0 mg, 0.034 mmol) in $CH_2Cl_2$ (0.87 mL) and $iPr_2EtN$ (0.145 mL, 0.829 mmol, 24 equiv) was added benzoic anhydride (23 mg, 0.102 mmol, 3 equiv). The mixture was stirred for 11 h and then quenched with phosphate buffer (pH ~2-3, 1 mL) washed with brine and dried with $MgSO_4$. The crude product was purified by flash chromatography (30-50% EtOAc/hexanes) to obtain 17 as a white powder (16.6 mg, 77%). $^1$H-NMR (400 MHz, $CDCl_3$) δ 8.15-8.09 (m, $2H_{AR}$), 7.66-7.56 (m, $1H_{AR}$), 7.52-7.38 (m, $^7H_{AR}$), 5.75 (s, 1H, 12-H), 5.48 (d, J=9.5 Hz, 1H, benzyl), 5.44 (d, J=4.0 Hz, 1H, 6-H), 5.17 (s, 1H, 10-H), 5.06 (d, J=3.9 Hz, 1H, 7-H), 4.91 (d, J=7.7 Hz, 1H, 2-H), 4.83 (d, J=9.5 Hz, 1H, benzyl), 4.28 (dd, J=7.6, 2.3 Hz, 1H, 1-H), 3.83 (s, 1H, 3-OH), 3.22 (q, J=6.9 Hz, 1H, 14-H), 3.22 (d, J=2.7 Hz, 1H, 1-OH), 2.30 (s, 1H, 8-H), 1.35 (d, J=7.07 Hz, 3H, 16-$CH_3$), 1.25 (s, 9H, tBu); $^{13}$C-NMR (100 MHz, $CDCl_3$) δ 6.99, 29.71, 33.74, 41.47, 61.78, 62.86, 67.73, 69.90, 73.11, 74.29, 75.21, 78.81, 84.07, 91.96, 95.53, 110.02, 127.82, 128.80, 129.23, 129.46, 129.90, 130.19, 133.65, 134.18, 165.09, 166.56, 170.70, 176.38; HRMS (FAB) calcd for $C_{34}H_{35}O_{12}$ 635.2129, found 635.2097.

10-Benzyloxy-isoGC-1,6-bisacetate (19). To a solution of 16 (8.5 mg, 0.016 mmol) in $CH_2Cl_2$ (0.15 mL) and $iPr_2EtN$ (28 mL, 0.16 mmol, 10 equiv) was added acetic anhydride (15 mL, 0.16 mmol, 10 equiv). The mixture was stirred for 12 h and then quenched with aq. HCl (1 mL, 1M), extracted with EtOAc (3×) and dried with $MgSO_4$. The crude product was purified by flash chromatography (40-50% EtOAc/hexanes) to obtain 19 as a white powder (8.0 mg, 81%). $^1$H-NMR (300 MHz, $CDCl_3$) δ 7.43-7.38 (m, $5H_{AR}$), 5.66 (d, J=3.7 Hz, 1H, 1-H), 5.63 (S, 1H, 12-H), 5.51 (d, J=4.1 Hz, 1H, 6-H), 5.30 (d, J=10.6 Hz, 1H, benzyl), 5.01 (s, 1H, 10-H), 4.83 (d, J=4.1 Hz, 1H, 7-H), 4.72 (d, J=10.6 Hz, 1H, benzyl), 4.48 (d, J=3.7 Hz, 1H, 2-H), 3.31 (q, J=7.5 Hz, 1H, 14-H), 3.30 (S, 1H, 3-OH), 2.20 (S, 1H, 8-H), 2.12 (S, 3H, $CH_3$-acetyl), 1.31 (d, J=7.5 Hz, 3H, 16-$CH_3$), 1.30 (S, 3H, $CH_3$-acetyl), 1.19 (s, 9H, tBu); $^{13}$C-NMR (75 MHz, $CDCl_3$) δ 9.56, 19.52, 20.59, 29.26, 33.63, 41.21, 61.55, 63.67, 67.20, 70.13, 73.29, 74.25, 74.98, 78.99, 84.47, 92.04, 97.31, 108.60, 128.76 (2 C), 128.93, 135.22, 166.51, 167.87, 168.74, 170.07, 175.87; HRMS (FAB) calcd for $C_{31}H_{35}O_{13}$ 615.2078, found 615.2083.

10-(4-Methoxy-benzyloxy)-isoGC-1,6-bisacetate (20). To a solution of 24 (13.4 mg, 0.024 mmol) in $CH_2Cl_2$ (0.24 mL) and $iPr_2EtN$ (42 mL, 0.24 mmol, 10 equiv) was added acetic anhydride (23 mL, 0.24 mmol, 10 equiv). The mixture was stirred for 12 h and then quenched with aq. HCl (1 mL, 1M), extracted with EtOAc (3×) and dried with $MgSO_4$. The crude product was purified by flash chromatography (40-70% EtOAc/hexanes) to obtain 20 as a white powder (12.1 mg, 79%). $^1$H-NMR (400 MHz, $CDCl_3$) δ 7.31-7.24 (m, $2H_{AR}$), 6.93-6.86 (m, $2H_{AR}$), 5.64 (d, J=3.8 Hz, 1H, 1-H), 5.63 (S, 1H, 12-H), 5.45 (d, J=4.1 Hz, 1H, 6-H), 5.18 (d, J=10.4 Hz, 1H, benzyl), 5.00 (s, 1H, 10-H), 4.82 (d, J=4.1 Hz, 1H, 7-H), 4.69 (d, J=10.4 Hz, 1H, benzyl), 4.50 (d, J=3.8 Hz, 1H, 2-H), 3.81 (s, 3H, —OMe), 3.34 (s, 1H, 3-OH), 3.30 (q, J=7.5 Hz, 1H, 14-H), 2.20 (s, 1H, 8-H), 2.12 (s, 3H, $CH_3$-acetyl), 1.39 (s, 3H, $CH_3$-acetyl), 1.30 (d, J=7.5 Hz, 3H, 16-$CH_3$), 1.17 (s, 9H, tBu); $^{13}$C-NMR (100 MHz, $CDCl_3$) δ 9.40, 19.62, 20.53, 29.27, 33.52, 41.08, 55.17, 61.28, 63.41, 66.87, 69.90, 72.62, 73.84, 74.18, 78.70, 84.15, 91.75, 96.83, 108.29, 113.65, 126.79, 130.36, 159.46, 165.97, 167.33, 168.21, 169.65, 175.34; HSQC correlation data in the Supporting Information; HRMS (FAB) calcd for $C_{32}H_{36}O_{14}$ 644.2105, found 644.2082.

10-Benzyloxy-GC-7-benzoate (21). To a solution of 16 (22.9 mg, 0.043 mmol) in $CH_2Cl_2$ (0.9 mL) and pyridine (0.15 mL, 1.85 mmol, 43 equiv) was added benzoyl chloride (25 mL, 0.216 mmol, 5 equiv). The mixture was stirred for 5 h and then quenched with aq. HCl (1 mL, 1M), washed with brine and dried with $MgSO_4$. The crude product was purified by flash chromatography (30-40% EtOAc/hexanes) to obtain 21 as a white powder (21.6 mg, 79%). $^1$H-NMR (400 MHz, $CDCl_3$) δ 8.12-8.05 (m, $2H_{AR}$), 7.68-7.58 (m, $1H_{AR}$), 7.53-7.40 (m, $^7H_{AR}$), 6.08 (s, 1H, 12-H), 5.50 (dd, J=12.9, 4.3 Hz, 1H, 7-H), 5.48 (d, J=9.4 Hz, 1H, benzyl), 5.41 (d, J=4.3 Hz, 1H, 6-H), 5.02 (s, 1H, 10-H), 4.76 (d, J=9.4 Hz, 1H, benzyl), 4.51 (d, J=7.9 Hz, 1H, 2-H), 4.26 (dd, J=7.9, 3.2 Hz, 1H, 1-H), 3.07 (q, J=7.0 Hz, 1H, 14-H), 2.86 (d, J=3.2 Hz, 1H, 1-OH), 2.9-2.7 (bs, 1H, 3-OH), 2.25 (d, J=12.9 Hz, 1H, 8-H), 1.31 (d, J=7.0 Hz, 3H, 16-$CH_3$), 1.20 (s, 9H, tBu); $^{13}$C-NMR (100 MHz, $CDCl_3$) δ 7.26, 29.36, 32.13, 41.57, 48.60, 64.03, 67.83, 73.93, 74.01, 74.15, 75.39, 76.88, 83.41, 90.53, 98.34, 109.86, 128.60, 128.74, 128.80, 129.57, 129.85, 130.06, 133.95, 134.12, 164.84, 170.50, 170.97, 175.13; HRMS (FAB) calcd for $C_{34}H_{35}O_{12}$ 635.2129, found 635.2156.

10-Benzyloxy-isoGC-1,6-bisbenzoate (22). To a solution of 16 (9.3 mg, 0.015 mmol) in $CH_2Cl_2$ (0.38 mL) and $iPr_2EtN$ (63 mL, 0.36 mmol, 24 equiv) was added benzoic anhydride (19.9 mg, 0.090 mmol, 6 equiv). The mixture was stirred for 20 h and then quenched with aq. HCl (1 mL, 1M), washed with brine and dried with $MgSO_4$. The crude product was purified by flash chromatography (30-50% EtOAc/1% AcOH/hexanes) to obtain 22 as a white powder (7.1 mg, 64%). $^1$H-NMR (400 MHz, $CDCl_3$) δ 8.25-8.18 (m, $2H_{AR}$), 7.66-7.58 (m, $3H_{AR}$), 7.52-7.37 (m, $3H_{AR}$), 7.21-7.13 (m, $2H_{AR}$), 7.11-7.03 (m, $2H_{AR}$), 7.02-6.95 (m, $3H_{AR}$), 6.02 (d, J=5.1 Hz, 1H, 1-H), 5.79 (d, J=4.0 Hz, 1H, 6-H), 5.69 (s, 1H, 12-H), 5.03 (d, J=4.0 Hz, 1H, 7-H), 5.01 (s, 1H, 10-H), 4.88 (d, J=5.1 Hz, 1H, 2-H), 4.86 (s, 2H, benzyl), 3.66 (s, 1H, 3-OH), 3.41 (q, J=7.3 Hz, 1H, 14-H), 2.25 (s, 1H, 8-H), 1.39 (d, J=7.3 Hz, 3H, 16-$CH_3$), 1.08 (s, 9H, tBu); $^{13}$C-NMR (75 MHz, $CDCl_3$) δ 8.60, 29.21, 33.73, 41.42, 61.61, 64.01, 67.11, 71.02, 72.94, 73.78, 74.05, 79.05, 84.72, 92.51, 96.69, 109.00, 127.96, 128.25, 128.29, 128.62, 128.91, 128.98, 129.22, 129.58, 130.21, 133.08, 133.92, 134.37, 163.78, 165.61, 166.74, 170.05, 175.91; HRMS (FAB) calcd for $C_{41}H_{39}O_{13}$ 739.2391, found 739.2381.

10-Benzyloxy-GC-1-benzoate (23). To a solution of 17 (15.6 mg, 0.025 mmol) in DMF (0.40 mL) was added $iPr_2EtN$ (50 mL, 0.29 mmol, 12 equiv) and mixture was stirred for 1.5 h at 100° C. Solvent was removed under reduced pressure, a residue was treated with phosphate buffer (pH 2-3, 1 mL), then extracted with EtOAc (3×) and combined organic layers were dried with $MgSO_4$. The crude product was purified by flash chromatography (30-50% EtOAc/hexanes) to obtain 23 as a white solid (12.2 mg, 78%). $^1$H-NMR (400 MHz, $CDCl_3$) δ 7.64-7.59 (m, $2H_{AR}$), 7.51-7.45 (m, $1H_{AR}$), 7.31-7.25 (m, $2H_{AR}$), 6.98-6.91 (m, $2H_{AR}$), 6.88-6.83 (m, $3H_{AR}$), 6.03 (s, 1H, 12-H), 5.89 (d, J=6.1 Hz, 1H, 1-H), 5.46 (d, J=4.4 Hz, 1H, 6-H), 5.17 (d, J=11.0 Hz, 1H, benzyl), 4.85 (s, 1H, 10-H), 4.70 (d, J=6.1 Hz, 1H, 2-H), 4.56 (d, J=10.9 Hz, 1H, benzyl), 4.42-4.33 (m, 1H, 7-H), 3.28 (q, J=7.2 Hz, 1H, 14-H), 3.4-2.9 (bs, 1H, 3-OH), 2.65-2.3 (bs, 1H, 7-OH), 1.76 (d, J=12.3 Hz, 1H, 8-H), 1.33 (d, J=7.2 Hz, 3H, 16-$CH_3$), 1.15 (s, 9H, tBu); $^{13}$C-NMR (100 MHz, $CDCl_3$) δ 7.94, 29.13, 32.34, 41.20, 50.57, 65.09, 66.47, 73.55, 74.30, 75.25, 75.64, 80.32, 84.27, 92.14, 99.62, 109.34, 128.02, 128.11, 128.24, 128.34, 128.70, 129.56, 133.23, 134.66, 163.47, 170.25, 170.70, 174.91; HRMS (FAB) calcd for $C_{34}H_{35}O_{12}$ 635.2129, found 635.2148.

10-(4-Methoxy-benzyloxy)-GC (24). To a solution of GC (3) (201 mg, 0.456 mmol) in DMF (2.28 mL) was added powdered $K_2CO_3$ (315 mg, 2.28 mmol, 5 equiv) and 4-methoxybenzyl chloride (620 mL, 4.56 mmol, 10 equiv). The mixture was stirred at 60° C. for 3 h and then stirred at room temperature for 5 h. The solution was concentrated under reduced pressure, an aq. phosphate buffer (pH 2-3, 10 mL) was added and the resulting solution was extracted with EtOAc (3×) and dried with $MgSO_4$. The crude product was purified by flash chromatography (40-100% EtOAc/hexanes) to obtain 24 as a white powder (240 mg, 94%). $^1$H-NMR (300 MHz, $CDCl_3$) δ 7.35-7.27 (m, $2H_{AR}$), 6.99-6.89 (m, $2H_{AR}$), 5.98 (s, 1H, 12-H), 5.41 (d, J=9.2 Hz, 1H, benzyl), 5.12 (d, J=4.4 Hz, 1H, 6-H), 4.92 (s, 1H, 10-H), 4.57 (d, J=9.2 Hz, 1H, benzyl), 4.52 (d, J=7.9 Hz, 1H, 2-H), 4.21 (dd, J=3.4, 7.9 Hz, 1H, 1-H), 4.13 (m, 1H, 7-H), 3.83 (s, 3H, —$OCH_3$), 3.05 (q, J=7.1 Hz, 1H, 14-H), 2.88 (d, J=3.4 Hz, 1H, 1-OH), 2.75 (s, 1H, 3-OH), 2.12 (d, J=11.5 Hz, 1H, 7-OH), 1.69 (d, J=12.4 Hz, 1H, 8-H), 1.30 (d, J=7.0 Hz, 3H, 16-$CH_3$), 1.23 (s, 9H, tBu); $^{13}$C-NMR (100 MHz, $CDCl_3$) δ 7.23, 29.08, 32.19, 41.65, 50.38, 55.31, 64.03, 67.08, 73.79, 75.31, 75.59, 79.33, 83.47, 90.70, 98.49, 110.13, 114.73, 126.36, 130.65, 160.56, 170.90, 171.03, 175.83; HRMS (FAB) calcd for $C_{28}H_{32}O_{12}$ 560.1894, found 560.1866.

10-(2-Pyridinyl-methoxy)-GC (25). A mixture of 2-picolylchloride hydrochloride (401.4 mg, 2.45 mmol, 6 equiv) and EtOAc was washed with sat. aq. NaHCO$_3$ (2×), brine and dried with MgSO$_4$. After filtration and removal of EtOAc, free 2-picolyl chloride was added to a solution of GC (3, 179.6 mg, 0.408 mmol, 1 equiv) in DMF (2.04 mL) and powdered K$_2$CO$_3$ (338 mg, 2.45 mmol, 6 equiv) was added. The mixture was briefly heated to about 60° C. and then stirred at room temperature for 15 h. The solution was concentrated under reduced pressure, an aq. phosphate buffer (pH 2-3, 10 mL) was added and resulting solution was extracted with EtOAc (3×) and dried with MgSO$_4$.

The crude product was purified by flash chromatography (50-100% EtOAc/hexanes) to obtain 25 as a white powder (211.2 mg, 97%). $^1$H-NMR (400 MHz, CDCl$_3$) δ 8.54 (d, J=4.9 Hz, 1H$_{AR}$), 8.20 (d, J=4.1 Hz, 1H, 1-OH), 7.79-7.71 (m, 1H$_{AR}$), 7.35-7.28 (m, 1H$_{AR}$), 7.19-7.11 (m, 1H$_{AR}$), 6.00 (s, 1H, 12-H), 5.67 (d, J=13.0 Hz, 1H, benzyl), 5.43 (d, J=4.3 Hz, 1H, 6-H), 4.96 (s, 1H, 10-H), 4.82 (d, J=13.0 Hz, 1H, benzyl), 4.66 (d, J=7.6 Hz, 1H, 2-H), 4.47-4.38 (m, 1H, 1-H), 4.27-4.17 (m, 1H, 7-H), 3.10 (s, 1H, 3-OH), 3.08 (q, J=7.0 Hz, 1H, 14-H), 2.32 (d, J=11.3 Hz, 1H, 7-OH), 1.73 (d, J=12.4 Hz, 1H, 8-H), 1.30 (d, J=7.0 Hz, 3H, 16-CH$_3$), 1.18 (s, 9H, tBu); $^{13}$C-NMR (100 MHz, CDCl$_3$) δ 7.33, 29.12, 32.27, 41.74, 50.55, 64.70, 67.62, 70.67, 73.81, 74.89, 75.36, 80.14, 83.06, 92.61, 98.74, 109.99, 120.37, 123.29, 137.41, 148.74, 154.52, 170.96, 171.45, 175.79; HRMS (FAB) calcd for $C_{26}H_{30}O_{11}N$ 532.1819, found 532.1844.

10-(4-Methoxy-benzyloxy)-GC-7-benzoate (26). To a solution of 24 (11.3 mg, 0.0202 mmol) in CH$_2$Cl$_2$ (0.34 mL) and pyridine (56 mL, 0.69 mmol, 34 equiv) was added benzoyl chloride (11.7 mL, 0.101 mmol, 5 equiv). Mixture was stirred for 7 h and then quenched with aq. HCl (1 mL, 1M), extracted with EtOAc (3×) and dried with MgSO$_4$. The crude product was purified by flash chromatography (30-50% EtOAc/hexanes) to obtain 26 as a white powder (12.3 mg, 92%). $^1$H-NMR (300 MHz, CDCl$_3$) δ 8.13-8.03 (m, 2H$_{AR}$), 7.69-7.58 (m, 1H$_{AR}$), 7.54-7.44 (m, 2H$_{AR}$), 7.44-7.34 (m, 2H$_{AR}$) 7.03-6.94 (m, 2H$_{AR}$), 6.07 (s, 1H, 12-H), 5.48 (dd, J=12.8, 4.3 Hz, 1H, 7-H), 5.40 (d, J=9.3 Hz, 1H, benzyl), 5.40 (d, J=4.3 Hz, 1H, 6-H), 4.99 (s, 1H, 10-H), 4.70 (d, J=9.3 Hz, 1H, benzyl), 4.50 (d, J=7.9 Hz, 1H, 2-H), 4.25 (dd, J=7.9, 3.4 Hz, 1H, 1-H), 3.84 (s, 3H, —OMe), 3.06 (q, J=7.0 Hz, 1H, 14-H), 2.92 (d, J=3.4 Hz, 1H, 1-OH), 2.90 (s, 1H, 3-OH), 2.24 (d, J=12.8 Hz, 1H, 8-H), 1.31 (d., J=7.0 Hz, 3H, 16-CH$_3$), 1.20 (s, 9H, tBu); $^{13}$C-NMR (75 MHz, CDCl$_3$) δ 7.28, 29.34, 32.10, 41.61, 48.57, 55.33, 64.01, 67.81, 73.70, 73.94, 73.97, 75.05, 76.84, 83.41, 90.54, 98.31, 109.87, 114.82, 126.18, 128.59, 128.73, 130.05, 130.57, 133.94, 160.61, 164.84, 170.65, 171.00, 175.28; HRMS (FAB) calcd for $C_{35}H_{36}O_{13}$ 664.2156, found 664.2129.

10-(4-Methoxy-benzyloxy)-isoGC-6-benzoate (27). To a solution of 24 (24.6 mg, 0.0438 mmol) in CH$_2$Cl$_2$ (0.83 mL) and iPr$_2$EtN (46 mL, 0.263 mmol, 6 equiv) was added benzoic anhydride (29.7 mg, 0.131 mmol, 3 equiv). Mixture was stirred for 11 h and then quenched with phosphate buffer (pH ~2-3, 1 mL), extracted with EtOAc and dried with MgSO$_4$. The crude product was purified by flash chromatography (30-50% EtOAc/1% AcOH/hexanes) to obtain 27 as a white powder (16.5 mg, 57%). $^1$H-NMR (400 MHz, CDCl$_3$) δ 8.15-8.08 (m, 2H$_{AR}$), 7.62-7.55 (m, 1H$_{AR}$), 7.48-7.39 (m, 2H$_{AR}$)., 7.38-7.30 (m, 2H$_{AR}$), 6.96-6.88 (m, 2H$_{AR}$), 5.74 (s, 1H, 12-H), 5.42 (d, J=4.0 Hz, 1H, 6-H), 5.40 (d, J=9.4 Hz, 1H, benzyl), 5.16 (s, 1H, 10-H), 5.06 (d, J=4.0 Hz, 1H, 7-H), 4.91 (d, J=7.7 Hz, 1H, 2-H), 4.76 (d, J=9.4 Hz, 1H, benzyl), 4.27 (dd, J=7.7, 2.6 Hz, 1H, 1-H), 3.84 (s, 1H, 3-OH), 3.79 (s, 3H, —OMe), 3.30 (d, J=2.7 Hz, 1H, 1-OH), 3.22 (q, J=7.1 Hz, 1H, 14-H), 2.30 (s, 1H, 8-H), 1.35 (d, J=7.1 Hz, 3H, 16-CH$_3$), 1.25 (s, 9H, tBu); $^{13}$C-NMR (75 MHz, CDCl$_3$) δ 6.99, 29.39, 33.76, 41.49, 55.31, 61.79, 62.91, 67.76, 69.96, 73.12, 73.86, 74.94, 78.86, 84.11, 91.98, 95.51, 110.06, 114.76, 125.78, 127.88, 128.80, 130.23, 130.98, 134.17, 160.71, 165.11, 166.61, 170.84, 176.40; HRMS (FAB) calcd for $C_{35}H_{36}O_{13}$ 664.2156, found 664.2165.

10-(4-Methoxy-benzyloxy)-GC-1-benzoate (28). To a solution of 27 (9.9 mg, 0.015 mmol) in DMF (0.25 mL) was added iPr$_2$EtN (30 mL, 0.17 mmol, 12 equiv) and the mixture was stirred for 3 h at 100° C. Solvent was removed under reduced pressure, a residue was treated with phosphate buffer (pH ~2-3, 1 mL), then extracted with EtOAc (3×) and combined organic layers were dried with MgSO$_4$. The crude product was purified by flash chromatography (30-50% EtOAc/hexanes) to obtain 28 as a white solid (7.9 mg, 80%). $^1$H-NMR (400 MHz, CDCl$_3$) δ 7.64-7.58 (m, 2H$_{AR}$), 7.52-7.45 (m, 1H$_{AR}$), 7.32-7.25 (m, 2H$_{AR}$), 6.91-6.85 (m, 2H$_{AR}$), 6.39-6.33 (m, 2H$_{AR}$), 6.02 (s, 1H, 12-H), 5.84 (d, J=6.2 Hz, 1H, 1-H), 5.44 (d, J=4.4 Hz, 1H, 6-H), 5.10 (d, J=10.5 Hz, 1H, benzyl), 4.83 (s, 1H, 10-H), 4.68 (d, J=6.2 Hz, 1H, 2-H), 4.47 (d, J=10.5 Hz, 1H, benzyl), 4.42-4.33 (m, 1H, 7-H), 3.60 (s, 3H, —OMe), 3.28 (q, J=7.1 Hz, 1H, 14-H), 3.09 (s, 1H, 3-OH), 2.37 (d, J=12.0 Hz, 1H, 7-OH), 1.74 (d, J=12.3 Hz, 1H, 8-H), 1.33 (d, J=7.1 Hz, 3H, 16-CH$_3$), 1.18 (s, 9H, tBu); $^{13}$C-NMR (125 MHz, CDCl$_3$) δ 7.85, 29.17, 32.34, 41.17, 50.65, 54.81, 65.09, 66.39, 73.31, 74.24, 74.99, 75.62, 80.32, 84.25, 92.11, 99.43, 109.33, 113.44, 126.84, 128.18, 128.71, 129.57, 129.88, 133.01, 159.24, 163.43, 170.31, 170.67, 174.72; HRMS (FAB) calcd for $C_{35}H_{36}O_{13}$ 664.2156, found 664.2170.

10-(2-Pyridinyl-methoxy)-GC-7-benzoate (29). To a solution of 25 (13.2 mg, 0.0248 mmol) in CH$_2$Cl$_2$ (0.52 mL) and pyridine (87 mL, 1.08 mmol, 43 equiv) was added benzoyl chloride (14.4 mL, 0.124 mmol, 5 equiv). Mixture was stirred for 7 h and then quenched with phosphate buffer (pH ~2-3, 1 mL), extracted with EtOAc (3×) and dried with MgSO$_4$. The crude product was purified by flash chromatography (40-50% EtOAc/hexanes) to obtain 29 as a white powder (13.4 mg, 85%). $^1$H-NMR (400 MHz, CDCl$_3$) δ 8.58 (d, J=5.0 Hz, 1H, 6-py), 8.42 (bs, 1H, 1-OH), 8.08-8.00 (m, 2H$_{AR}$), 7.79-7.71 (m, 1H, 4-py), 7.65-7.56 (m, 1H$_{AR}$), 7.51-7.42 (m, 2H$_{AR}$), 7.35-7.28 (m, 1H, 5-py), 7.15 (d, J=7.9 Hz, 1H, 3-py), 6.08 (s, 1H, 12-H), 5.75 (d, J=4.4 Hz, 1H, 6-H), 5.68 (d, J=13.1 Hz, 1H, benzyl), 5.48 (dd, J=12.8, 4.4 Hz, 1H, 7-H), 5.03 (s, 1H, 10-H), 4.89 (d, J=13.1 Hz, 1H, benzyl), 4.64 (d, J=7.5 Hz, 1H, 2-H), 4.48 (bd, J=7.5 Hz, 1H, 1-H), 3.09 (q, J=7.0 Hz, 1H, 14-H), 2.88 (bs, 1H, 3-OH), 2.28 (d, J=12.8 Hz, 1H, 8-H), 1.31 (d, J=7.0 Hz, 3H, 16-CH$_3$), 1.18 (s, 9H, tBu); $^{13}$C-NMR (100 MHz, CDCl$_3$) δ 7.34, 29.39, 32.24, 41.76, 48.89, 64.61, 68.43, 70.65, 73.84, 74.35, 74.93, 77.53, 83.04, 92.62, 98.68, 109.94, 120.22, 123.28, 128.67, 128.84, 130.00, 133.78, 137.37, 148.85, 154.47, 164.87, 170.71, 171.53, 175.63; HRMS (FAB) calcd for $C_{33}H_{34}O_{12}N$ 636.2081, found 636.2058.

GC-7-benzoate (30). To a solution of 26 (8.0 mg, 12.0 mmol) in acetonitrile (150 mL) and CHCl$_3$ (49 mL) was added aq. solution of (NH$_4$)$_2$Ce(NO$_3$)$_6$ (14.7 mL, 24 mmol, 2 equiv, 1.63M). The mixture was stirred for 14 h, volatiles were removed under reduced pressure and residue was purified by flash chromatography (30-100% EtOAc/1% AcOH/hexanes) to obtain 30 as a white powder (4.4 mg, 68%). $^1$H-NMR (400 MHz, CD$_3$OD) δ 8.11-8.05 (m, 2H$_{AR}$), 7.70-7.62 (m, 1H$_{AR}$), 7.57-7.49 (m, 2H$_{AR}$), 6.20 (s, 1H, 12-H), 5.54-5.46 (m, 2H, 6-H & 7-H), 5.19 (s, 1H, 10-H), 4.57 (d, J=7.6 Hz, 1H, 2-H), 4.22 (d, J=7.6 Hz, 1H, 1-H), 3.02 (q, J=7.1 Hz, 1H, 14-H), 2.29-2.22 (m, 1H, 8-H), 1.23 (d, J=7.1 Hz, 3H, 16-CH$_3$), 1.18 (s, 9H, tBu); HSQC correlation data in the Supporting Information; HRMS (FAB) calcd for C$_{27}$H$_{28}$O$_{12}$Na 567.1478, found 567.1472.

IsoGC-6-benzoate (31). To a solution of 27 (3.3 mg, 5.0 mmol) in acetonitrile (63 mL) and CHCl$_3$ (20 mL) was added aq. solution of (NH$_4$)$_2$Ce(NO$_3$)$_6$ (6.2 mL, 10 mmol, 2 equiv, 1.63M). The mixture was stirred for 3 h, volatiles were removed under reduced pressure and residue was purified by flash chromatography (30-70% EtOAc/1% AcOH/hexanes) to obtain 31 as a white powder (2.2 mg, 81%). $^1$H-NMR (400 MHz, CDCl$_3$) δ 8.18-8.11 (m, 2H$_{AR}$), 7.63-7.55 (m, 1H$_{AR}$), 7.48-7.40 (m, 2H$_{AR}$), 5.75 (s, 1H, 12-H), 5.64 (d, J=3.9 Hz, 1H, 6-H), 5.30 (s, 1H, 10-H), 5.06 (d, J=3.9 Hz, 1H, 7-H), 5.00 (d, J=7.7 Hz, 1H, 2-H), 4.26 (d, J=7.7 Hz, 1H, 1-H), 3.78 (s, 1H, 3-OH), 3.40 (q, J=7.1 Hz, 1H, 14-H), 2.29 (s, 1H, 8-H), 1.37 (d, J=7.1 Hz, 3H, 16-CH$_3$), 1.26 (s, 9H, tBu); HSQC correlation data in the Supporting Information; HRMS (FAB) calcd for C$_{27}$H$_{29}$O$_{12}$ 545.1659, found 545.1666.

GC-1-benzoate (32). To a solution of 28 (5.3 mg, 8.0 mmol) in acetonitrile (100 mL) and CHCl$_3$ (32 mL) was added aq. solution of (NH$_4$)$_2$Ce(NO$_3$)$_6$ (9.8 mL, 16 mmol, 2 equiv, 1.63M). The mixture was stirred for 1.5 h, aq. solution of (NH$_4$)$_2$Ce(NO$_3$)$_6$ (4.9 mL, 8 mmol, 1 equiv, 1.63M) was added and mixture was further stirred for 12 h. Volatiles were removed under reduced pressure and residue was purified by flash chromatography (40-70% EtOAc/hexanes) to obtain 32 as a white powder (2.6 mg, 60%). $^1$H-NMR (300 MHz, CDCl$_3$) δ 7.98-7.90 (m, 2H$_{AR}$), 7.67-7.58 (m, 1H$_{AR}$), 7.51-7.41 (m, 2H$_{AR}$), 6.05 (s, 1H, 12-H), 5.77 (d, J=6.8 Hz, 1H, 1-H), 5.47 (d, J=4.3 Hz, 1H, 6-H), 5.09 (d, J=1.9 Hz, 1H, 10-H), 4.77 (d, J=6.8 Hz, 1H, 2-H), 4.40-4.28 (m, 1H, 7-H), 3.56 (d, J=1.9 Hz, 1H, 10-OH), 3.22 (q, J=7.1 Hz, 1H, 14-H), 2.86 (s, 1H, 3-OH), 2.25 (d, J=11.7 Hz, 1H, 7-OH), 1.75 (d, J=12.3 Hz, 1H, 8-H), 1.33 (d, J=7.1 Hz, 3H, 16-CH$_3$), 1.19 (s, 9H, tBu); HSQC correlation data in the Supporting Information; HRMS (FAB) calcd for C$_{27}$H$_{29}$O$_{12}$ 545.1659, found 545.1641.

7-(4-Nitro-phenoxycarbonyloxy)-10-Benzyloxy-GC (33). To a solution of 16 (34.7 mg, 0.065 mmol) in CH$_2$Cl$_2$ (0.82 mL) and pyridine (187 mL, 2.31 mmol, 35 equiv) was added solution of p-nitrophenyl chloroformate (39.6 mg, 0.195 mmol, 3 equiv) in CH$_2$Cl$_2$ (0.3 mL). The mixture was stirred for 50 min and then quenched with aq. HCl (2 mL, 1M), extracted with EtOAc (3×) and dried with MgSO$_4$. The crude product was recrystalized from CHCl$_3$ to obtain 33 as a white crystals (27.8 mg, 61%). $^1$H-NMR (300 MHz, CDCl$_3$) δ 8.36-8.27 (m, 2H$_{AR}$), 7.50-7.32 (m, 7H$_{AR}$), 6.07 (s, 1H, 12-H), 5.47 (d, J=9.4 Hz, 1H, benzyl), 5.47 (d, J=4.3 Hz, 1H, 6-H), 5.08 (dd, J=12.8, 4.3 Hz, 1H, 7-H), 4.99 (s, 1H, 10-H), 4.72. (d, J=9.4 Hz, 1H, benzyl), 4.51 (d, J=7.8 Hz, 1H, 2-H), 4.25 (dd, J=7.8, 3.5 Hz, 1H, 1-H), 3.05 (q, J=7.0 Hz, 1H, 14-H), 2.88 (bs, 1H, 3-OH), 2.79 (d, J=3.5 Hz, 1H, 1-OH), 2.18 (d, J=12.8 Hz, 1H, 8-H), 1.32 (d, J=7.0 Hz, 3H, 16-CH$_3$), 1.23 (s, 9H, tBu).

7-Methylcarbamoyloxy-10-benzyloxy-GC (34). To a solution of 33 (6.4 mg, 9.3 mmol) in THF (0.17 mL) was added MeNH$_2$ in THF (14 mL, 28 mmol, 3 equiv, 2M). The mixture was stirred for 25 min and then quenched with sat. aq. NH$_4$Cl, extracted with EtOAc (3×) and dried with MgSO$_4$. The crude product was purified by flash chromatography (40-50% EtOAc/hexanes) to obtain 34 as a white solid (4.8 mg, 88%). $^1$H-NMR (400 MHz, CDCl$_3$) δ 7.50-7.37 (m, 5H$_{AR}$), 6.02 (s, 1H, 12-H), 5.44 (d, J=9.4 Hz, 1H, benzyl), 5.28 (d, J=4.4 Hz, 1H, 6-H), 5.21 (dd, J=12.8, 4.4 Hz, 1H, 7-H), 4.96 (s, 1H, 10-H), 4.84 (bq, J~4.8 Hz, 1H, —NH—), 4.73 (d, J=9.4 Hz, 1H, benzyl), 4.49 (d, J=7.8 Hz, 1H, 2-H), 4.21 (dd, J=7.8, 3.4 Hz, 1H, 1-H), 3.03 (q, J=7.0 Hz, 1H, 14-H), 2.92 (s, 1H, 3-OH), 2.86 (d, J=4.9 Hz, 3H, CH$_3$), 2.80 (d, J=3.4 Hz, 1H, 1-OH), 2.00 (d, J=12.8 Hz, 1H, 8-H), 1.30 (d, J=7.0 Hz, 3H, 16-CH$_3$), 1.16 (s, 9H, tBu); $^{13}$C-NMR (75 MHz, CDCl$_3$) δ 7.25, 27.72, 29.31, 32.12, 41.58, 48.50, 63.90, 67.65, 74.02, 74.10, 74.20, 75.36, 77.30, 83.41, 90.61, 98.37, 109.92, 128.82, 129.53, 129.78, 134.15, 154.68, 170.59, 171.04, 175.17; HRMS (FAB) calcd for C$_{29}$H$_{34}$O$_{12}$N 588.2081, found 588.2069.

7-tert-Butylcarbamoyloxy-10-benzyloxy-GC (35). To a solution of 33 (5.5 mg, 7.9 mmol) in THF (0.16 mL) was added t-BuNH$_2$ (3.4 mL, 32 mmol, 4 equiv). The mixture was stirred for 40 min. and then quenched with aq. HCl (1 mL, 1M), extracted with EtOAc (3×) and dried with MgSO$_4$. The crude product was purified by flash chromatography (30-50% EtOAc/hexanes) to obtain 35 as a white solid (4.4 mg, 88%). The product was further purified by reverse phase HPLC. $^1$H-NMR (500 MHz, CDCl$_3$) δ 7.48-7.38 (m, 5H$_{AR}$), 6.02 (s, 1H, 12-H), 5.43 (d, J=9.5 Hz, 1H, benzyl), 5.28 (d, J=4.2 Hz, 1H, 6-H), 5.18 (dd, J=12.5, 4.2 Hz, 1H, 7-H), 4.96 (s, 1H, 10-H), 4.79 (s, 1H, —NH—), 4.75 (d, J=9.5 Hz, 1H, benzyl), 4.50 (d, J=7.8 Hz, 1H, 2-H), 4.21 (dd, J=7.9, 3.4 Hz, 1H, 1-H), 3.04 (q, J=7.0 Hz, 1H, 14-H), 2.81 (d, J=3.4 Hz, 1H, 1-OH), 2.69 (s, 1H, 3-OH), 1.98 (d, J=12.8 Hz, 1H, 8-H), 1.35 (s, 9H, tBu), 1.30 (d, J=7.0 Hz, 3H, 16-CH$_3$), 1.15 (s, 9H, tBu); $^{13}$C-NMR (125 MHz, CDCl$_3$) δ 7.21, 28.82, 29.33, 32.10, 41.53, 48.65, 50.93, 63.95, 67.65, 73.38, 74.07, 74.10, 75.39, 77.56, 83.43, 90.56, 98.34, 109.97, 128.85, 129.50, 129.73, 134.16, 152.11, 170.62, 171.09, 175.08; HSQC correlation data in the Supporting Information; HRMS (FAB) calcd for C$_{32}$H$_{39}$O$_{12}$NNa 652.2370, found 652.2368.

7-(Morpholine-4-carbonyloxy)-10-benzyloxy-GC (36). To a solution of 33 (5.2 mg, 7.5 mmol) in THF (0.15 mL) was added morpholine (2 mL, 23 mmol, 3 equiv). The mixture was stirred for 25 min and then quenched with aq. HCl (1 mL, 1M), extracted with EtOAc (3×) and dried with MgSO$_4$. The crude product was purified by flash chromatography (0.40-50% EtOAc/hexanes) to obtain 36 as a white solid (6.0 mg, 92%). $^1$H-NMR (400 MHz, CDCl$_3$) δ 7.49-7.38 (m, 5H$_{AR}$), 6.03 (s, 1H, 12-H), 5.44 (d, J=9.4 Hz, 1H, benzyl), 5.32-5.23 (m, 2H, 6-H & 7-H), 4.97 (s, 1H, 10-H), 4.74 (d, J=9.4 Hz, 1H, benzyl), 4.48 (d, J=7.8 Hz, 1H, 2-H), 4.22 (dd, J=7.8, 3.5 Hz, 1H, 1-H), 3.77-3.33 (m, 8H, morph.), 3.04 (q, J=7.0 Hz, 1H, 14-H), 2.93 (s, 1H, 3-OH), 2.80 (d, J=3.5 Hz, 1H, 1-OH), 2.09-2.00 (m, 1H, 8-H), 1.30 (d, J=7.0 Hz, 3H, 16-CH$_3$), 1.17 (s, 9H, tBu); $^{13}$C-NMR (100 MHz, CDCl$_3$) δ 7.27, 29.31, 32.13, 41.57, 44.21 (morph.), 44.48 (morph.), 48.62, 63.94, 66.48 (morph.), 66.59 (morph.), 67.56, 73.97, 74.06, 74.68, 75.30, 77.14, 83.40, 90.58, 98.39, 109.88, 128.80, 129.51, 129.78, 134.10, 152.99, 170.53, 171.02, 175.16; HRMS (FAB) calcd for C$_{32}$H$_{38}$O$_{13}$N 644.2343, found 644.2333.

7-(Piperidine-carbonyloxy)-10-benzyloxy-GC (37). To a solution of 33 (5.0 mg, 7.2 mmol) in THF (0.15 mL) was added piperidine (2.1 mL, 22 mmol, 3 equiv). The mixture was stirred for 30 min and then quenched with aq. HCl (1 mL, 1M), extracted with EtOAc (3×) and dried with MgSO$_4$. The crude product was purified by flash chromatography (30-40% EtOAc/hexanes) to obtain 37 as a white solid (3.8 mg, 81%). $^1$H-NMR (300 MHz, CDCl$_3$) δ 7.50-7.37 (m, 5H$_{AR}$), 6.03 (s, 1H, 12-H), 5.43 (d, J=9.4 Hz, 1H, benzyl), 5.32-5.23 (m, 2H, 6-H & 7-H), 4.97 (s, 1H, 10-H), 4.74 (d, J=9.4 Hz, 1H, benzyl), 4.48 (d, J=7.8 Hz, 1H, 2-H), 4.21 (dd, J=7.8, 3.4 Hz, 1H, 1-H), 3.57-3.33 (m, 4H, piper.), 3.04 (q, J=7.0 Hz, 1H, 14-H), 2.79 (d, J=3.4 Hz, 1H, 1-OH), 2.78 (s, 1H, 3-OH), 2.10-1.99 (m, 1H, 8-H), 1.71-1.40 (m, 6H, piper.), 1.30 (d, J=7.0 Hz, 3H, 16-CH$_3$), 1.17 (s, 9H, tBu); $^{13}$C-NMR (75 MHz, CDCl$_3$) δ 7.25, 24.22 (piper.), 25.55 (piper.), 25.89 (piper.), 29.31, 32.12, 41.56, 45.20 (piper.), 48.66, 63.97, 67.57, 74.01, 74.04, 74.37, 75.33, 77.23, 83.39, 90.58, 98.37, 109.93, 128.80, 129.50, 129.73, 134.13, 152.94, 170.63, 171.12, 175.14; HRMS (FAB) calcd for C$_{33}$H$_{40}$O$_{12}$N 642.2551, found 642.2579.

1-Methylcarbamoyloxy-10-benzyloxy-GC (39). To a solution of 16 (9.3 mg, 17.6 mmol) in CH$_2$Cl$_2$ (110 mL) and iPr$_2$EtN (18.4 mL, 0.105 mmol, 6 equiv), was added a solution of p-nitrophenyl chloroformate (10.6 mg, 52.6 mmol, 3 equiv) in CH$_2$Cl$_2$ (50 mL). The mixture was stirred for 16 min and MeNH$_2$ (2M in THF, 26 mL, 52.6 mmol, 3 equiv) and THF (80 mL) were added. The mixture was then stirred for additional 25 min and then quenched with aq. HCl (1 mL, 1M), extracted with EtOAc (3×) and dried with MgSO$_4$. The crude product was purified by flash chromatography (50-100% EtOAc/hexanes) to obtain 39 as a white solid (6.6 mg, 64%). $^1$H-NMR (300 MHz, 320K, CDCl$_3$) δ 7.42-7.2 (m, 5H$_{AR}$), 5.96 (s, 1H, 12-H), 5.55 (d, J=6.0 Hz, 1H, 1-H), 5.39 (d, J=11.5 Hz, 1H, benzyl), 5.19 (d, J=4.3 Hz, 1H, 6-H), 4.82 (s, 1H, 10-H), 4.64 (bd, J=11.5 Hz, 1H, benzyl), 4.62 (d, J=6.0 Hz, 1H, 2-H), 4.38-4.25 (m, 1H, 7-H), 4.26 (m, 1H, —NH—), 3.20 (q, J=7.2 Hz, 1H, 14-H), 2.92 (s, 1H, 3-OH), 2.29 (bd, J=4.1 Hz, 3H, CH$_3$), 2.16 (d, J=11.5 Hz, 1H, 7-OH), 1.69 (d, J=12.3 Hz, 1H, 8-H), 1.31 (d, J=7.2 Hz, 3H, 16-CH$_3$), 1.15 (s, 9H, tBu); HSQC correlation data in the Supporting Information; HRMS (FAB) calcd for C$_{29}$H$_{34}$O$_{12}$N 588.2081, found 588.2103.

1-tert-Butylcarbamoyloxy-10-benzyloxy-GC (40). To a solution of 16 (3.7 mg, 7.0 mmol) in CH$_2$Cl$_2$ (50 mL) and iPr$_2$EtN (7.3 mL, 42 mmol, 6 equiv), was added solution of p-nitrophenyl chloroformate (4.2 mg, 21 mmol, 3 equiv) in CH$_2$Cl$_2$ (20 mL). The mixture was stirred for 16 min and tBuNH$_2$ (7.4 mL, 70 mmol, 10 equiv) and THF (40 mL) were added. The mixture was then stirred for additional 12 h and then quenched with aq. HCl (1 mL, 1M), extracted with EtOAc (3×) and dried with MgSO$_4$. The crude product was purified by flash chromatography (40-50% EtOAc/hexanes) to obtain 40 as a white solid (2.6 mg, 59%). $^1$H-NMR (300 MHz, CDCl$_3$) δ 7.40-7.22 (m, 5H$_{AR}$), 5.93 (s, 1H, 12-H), 5.55 (d, J=5.1 Hz, 1H, 1-H), 5.32 (d, J=12.3 Hz, 1H, benzyl), 5.22 (d, J=4.3 Hz, 1H, 6-H), 4.81 (bd, J=11.5 Hz, 1H, benzyl), 4.79 (s, 1H, 10-H), 4.67 (d, J=5.1 Hz, 1H, 2-H), 4.53 (bs, 1H, —NH—), 4.36-4.24 (m, 1H, 7-H), 3.21 (q, J=7.3 Hz, 1H, 14-H), 3.17 (bs, 1H, 3-OH), 2.13 (bd, J=12.0 Hz, 1H, 7-OH), 1.65 (d, J=12.3 Hz, 1H, 8-H), 1.32 (d, J=7.3 Hz, 3H, 16-CH$_3$), 1.12 (s, 9H, tBu), 1.03 (s, 9H, tBu); $^{13}$C-NMR (100 MHz, CDCl$_3$) δ 8.57, 28.49, 28.97, 32.16, 40.94, 50.43, 50.75, 65.05, 66.53, 74.61, 74.94, 75.19, 80.10, 84.08, 91.90, 99.96, 108.52, 127.85, 128.12 (2), 135.55, 151.09, 169.47, 170.34, 174.20; HRMS (FAB) calcd for C$_{32}$H$_{40}$O$_{12}$N 630.2551, found 630.2554.

1-(Morpholine-4-carbonyloxy)-10-benzyloxy-GC (41). To a solution of 16 (6.3 mg, 12.0 mmol) in CH$_2$Cl$_2$ (350 mL) and iPr$_2$EtN (12.5 mL, 72 mmol, 6 equiv), was added solution of p-nitrophenyl chloroformate (7.2 mg, 36 mmol, 3 equiv) in CH$_2$Cl$_2$ (50 mL). The mixture was stirred for 30 min and morpholine (6.3 mL, 72 mmol, 6 equiv) was added. The mixture was then stirred for additional 2 h and then quenched with aq. HCl (1 mL, 1M), extracted with EtOAc (3×) and dried with MgSO$_4$. The crude product was purified by flash chromatography (50-100% EtOAc/hexanes) to obtain 41 as a white solid (6.0 mg, 78%). $^1$H-NMR (400 MHz, CDCl$_3$) δ 7.41-7.31 (m, 3H$_{AR}$), 7.29-7.21 (m, 2H$_{AR}$), 5.99 (s, 1H, 12-H), 5.60 (d, J=5.6 Hz, 1H, 1-H), 5.40 (d, J=11.5 Hz, 1H, benzyl), 5.15 (d, J=4.4 Hz, 1H, 6-H), 4.85 (s, 1H, 10-H), 4.71 (d, J=5.6 Hz, 1H, 2-H), 4.62 (d, J=11.5 Hz, 1H, benzyl), 4.38-4.28 (m, 1H, 7-H), 3.60 (s, 1H, 3-OH), 3.5-3.2 (m, 6H, morph.), 3.21 (q, J=7.2 Hz, 1H, 14-H), 2.78-2.67 (m, 1H, morph.), 2.50 (d, J=11.7 Hz, 1H, 7-OH), 2.49-2.38 (m, 1H, morph.), 1.72 (d, J=12.3 Hz, 1H, 8-H), 1.32 (d, J=7.2 Hz, 3H, 16-CH$_3$), 1.18 (S, 9H, tBu); $^{13}$C-NMR (75 MHz, CDCl$_3$) δ 8.30, 29.16, 32.40, 41.19, 43.48, 43.73, 50.40, 65.07, 65.87, 66.15, 66.51, 73.24, 75.65, 75.85, 80.21, 84.12, 92.16, 99.90, 109.11, 127.44, 128.42, 128.65, 136.20, 152.15, 169.99, 170.60, 175.04; HRMS (FAB) calcd for C$_{32}$H$_{38}$O$_{13}$N 644.2343, found 644.2355.

1-(Piperidine-carbonyloxy)-10-benzyloxy-GC (42). To a solution of 16 (11.3 mg, 21.3 mmol) in CH$_2$Cl$_2$ (710 mL) and iPr$_2$EtN (22.4 mL, 128 mmol, 6 equiv), was added solution of p-nitrophenyl chloroformate (13 mg, 64 mmol, 3 equiv) in CH$_2$Cl$_2$ (80 mL). The mixture was stirred for 30 min and piperidine (12.6 mL, 128 mmol, 6 equiv) was added. The mixture was then stirred for additional 2 h and then quenched with aq. HCl (1 mL, 1M), extracted with EtOAc (3×) and dried with MgSO$_4$. The crude product was purified by flash chromatography (35-70% EtOAc/hexanes) to obtain 42 as a white solid (6.8 mg, 50%). $^1$H-NMR (400 MHz, CDCl$_3$) δ 7.39-7.28 (m, 3H$_{AR}$), 7.28-7.21 (m, 2H$_{AR}$), 5.97 (S, 1H, 12-H), 5.57 (d, J=5.3 Hz, 1H, 1-H), 5.38 (d, J=11.5 Hz, 1H, benzyl), 5.14 (d, J=4.4 Hz, 1H, 6-H), 4.84 (s, 1H, 10-H), 4.72 (d, J=5.3 Hz, 1H, 2-H), 4.65 (d, J=11.5 Hz, 1H, benzyl), 4.37-4.28 (m, 1H, 7-H), 3.57 (s, 1H, 3-OH), 3.50-3.38 (m, 1H, piper.), 3.35-3.23 (m, 1H, piper.), 3.22 (q, J=7.3 Hz, 1H, 14-H), 2.60-2.49 (m, 1H, piper.), 2.47-2.37 (m, 1H, piper.), 2.36 (d, J=12.0 Hz, 1H, 7-OH), 1.70 (d, J=12.3 Hz, 1H, 8-H), 1.61-1.50 (m, 1H, piper.), 1.45-1.25 (m, 5H, piper.), 1.32 (d, J=7.3 Hz, 3H, 16-CH$_3$), 1.16 (S, 9H, tBu); $^{13}$C_NMR (100 MHz, CDCl$_3$) δ 8.53, 23.89, 24.96, 25.52, 29.17, 32.38, 41.15, 44.49, 44.64, 50.47, 65.17, 66.80, 73.12, 75.44, 75.64, 76.07, 80.39, 84.26, 92.23, 100.23, 108.98, 127.75, 128.17, 128.54, 136.16, 152.22, 170.02, 170.80, 175.00; HRMS (FAB) calcd for C$_{33}$H$_{40}$O$_{12}$N 642.2551, found 642.2521.

7-(4-Nitro-phenoxycarbonyloxy)-10-(4-methoxy-benzyloxy)-GC (43). To a solution of 24 (47.6 mg, 0.085 mmol) in CH$_2$Cl$_2$ (0.53 mL) and pyridine (121 mL, 1.50 mmol, 18 equiv) at 0° C. was added solution of p-nitrophenyl chloroformate (34.2 mg, 0.170 mmol, 2 equiv) in CH$_2$Cl$_2$ (0.2 mL). The mixture was allowed to warm up slowly to room temperature while stirring. After 2.5 h the reaction was quenched with aq. HCl (2 mL, 1M), extracted with EtOAc (3×) and dried with MgSO$_4$. The crude product was purified by flash chromatography (30-50% EtOAc/hexanes) to obtain 43 as a white powder (42.6 mg, 69%) and unreacted starting material 24 (9.5 mg, 20%). $^1$H-NMR (400 MHz, CDCl$_3$) δ 8.35-8.27 (m, 2H$_{AR}$), 7.46-7.38 (m, 2H$_{AR}$), 7.35-7.28 (m, 2H$_{AR}$), 6.95-6.88 (m, 2H$_{AR}$), 6.06 (s, 1H, 12-H), 5.45 (d, J=4.3 Hz, 1H, 6-H), 5.38 (d, J=9.3 Hz, 1H, benzyl), 5.05 (dd, J=12.8, 4.3 Hz, 1H, 7-H), 4.98 (s, 1H, 10-H), 4.66 (d, J=9.3 Hz, 1H, benzyl), 4.51 (d, J=7.8 Hz, 1H, 2-H)., 4.25 (dd, J=7.8, 3.5 Hz, 1H, 1-H), 3.80 (s, 3H, —OMe), 3.06 (q, J=7.0 Hz, 1H, 14-H), 3.04 (s, 1H, 3-OH), 2.87 (d, J=3.5 Hz, 1H, 1-OH), 2.17 (d, J=12.8 Hz, 1H, 8-H), 1.30 (d, J=7.0 Hz, 3H, 16-CH$_3$), 1.22 (s, 9H, tBu); $^{13}$C-NMR (100 MHz, CDCl$_3$) δ 7.46, 29.42, 32.24, 41.70, 48.48, 55.38, 63.85, 67.77, 73.72, 73.90, 74.93, 75.69, 78.17, 83.43, 90.48, 98.23, 109.65, 114.71, 121.48, 125.28, 125.94, 130.36, 145.52, 150.82, 154.72, 160.41, 170.07, 170.11, 174.90.

7-Methylcarbamoyloxy-10-(4-methoxy-benzyloxy)-GC (44). To a solution of 43 (14.2 mg, 19.5 mmol) in THF (0.20 mL) was added MeNH$_2$ in THF (29 mL, 59 mmol, 3 equiv, 2M). The mixture was stirred for 20 min and then quenched with aq. HCl (1 mL, 1M), extracted with EtOAc (3×) and dried with MgSO$_4$. The crude product was purified by flash chromatography (40-70% EtOAc/hexanes) to obtain 44 as a white solid (8.9 mg, 74%). $^1$H-NMR (500 MHz, CDCl$_3$) δ 7.36 (d, J=8.5 Hz, 2H$_{AR}$), 6.95 (d, J=8.5 Hz, 2H$_{AR}$), 6.01 (s, 1H, 12-H), 5.35 (d, J=9.3 Hz, 1H, benzyl), 5.26 (d, J=4.3 Hz, 1H, 6-H), 5.19 (dd, J=12.8, 4.4 Hz, 1H, 7-H), 4.94 (s, 1H, 10-H), 4.83 (bq, J~4.8 Hz, 1H, —NH—), 4.67 (d, J=9.3 Hz, 1H, benzyl), 4.49 (d, J=7.8 Hz, 1H, 2-H), 4.20 (dd, J=7.8, 3.3 Hz, 1H, 1-H), 3.82 (s, 3H, —OMe), 3.03 (q, J=7.0 Hz, 1H, 14-H), 2.90 (s, 1H, 3-OH), 2.89-2.80 (m, 4H, CH$_3$ & 1-OH), 1.99 (d, J=12.8 Hz, 1H, 8-H), 1.29 (d, J=7.0 Hz, 3H, 16-CH$_3$), 1.15 (s, 9H, tBu); $^{13}$C-NMR (100 MHz, CDCl$_3$) δ 7.24, 27.61, 29.21, 32.01, 41.47, 48.35, 55.14, 63.70, 67.43, 73.40, 73.77, 73.96, 74.78, 83.15, 90.31, 98.01, 109.55, 114.45, 125.81, 130.13, 154.19, 160.10, 170.15, 170.52, 174.69; HRMS (FAB) calcd for C$_{30}$H$_{34}$O$_{13}$N 616.2030, found 616.2056.

7-tert-Butylcarbamoyloxy-10-(4-methoxy-benzyloxy)-GC (45). To a solution of 43 (14.2 mg, 19.5 mmol) in THF (0.20 mL) was added t-BuNH$_2$ (6.2 mL, 59 mmol, 3 equiv). The mixture was stirred for 40 min and then quenched with aq. HCl (1 mL, 1M), extracted with EtOAc (3×) and dried with MgSO$_4$. The crude product was purified by flash chromatography (30-70% EtOAc/hexanes) to obtain 45 as a white solid (10.0 mg, 77%). $^1$H-NMR (400 MHz, CDCl$_3$) δ 7.41-7.35 (m, 2H$_{AR}$), 6.99-6.91 (m, 2H$_{AR}$), 6.01 (s, 1H, 12-H), 5.34 (d, J=9.3 Hz, 1H, benzyl), 5.26 (d, J=4.3 Hz, 1H, 6-H), 5.15 (dd, J=12.8, 4.2 Hz, 1H, 7-H), 4.94 (s, 1H, 10-H), 4.81 (s, 1H, —NH—), 4.69 (d, J=9.3 Hz, 1H, benzyl), 4.50 (d, J=7.9 Hz, 1H, 2-H), 4.20 (dd, J=7.9, 3.4 Hz, 1H, 1-H), 3.82 (s, 3H, —OMe), 3.03 (q, J=7.0 Hz, 1H, 14-H), 2.94 (s, 1H, 3-OH), 2.88 (d, J=3.4 Hz, 1H, 1-OH), 1.97 (d, J=12.8 Hz, 1H, 8-H), 1.35 (s, 9H, tBu), 1.29 (d, J=7.0 Hz, 3H, 16-CH$_3$), 1.15 (s, 9H, tBu); $^{13}$C-NMR (75 MHz, CDCl$_3$) δ 7.27, 28.79, 29.31, 32.08, 41.60, 48.60, 50.89, 55.30, 63.90, 67.61, 73.35, 73.62, 74.01, 75.02, 77.55, 83.42, 90.58, 98.34, 109.96, 114.76, 126.24, 130.63, 152.11, 160.56, 170.78, 171.18, 175.29; HRMS (FAB) calcd for C$_{33}$H$_{41}$O$_{13}$N 659.2578, found 659.2582.

7-(Morpholine-4-carbonyloxy)-10-(4-methoxy-benzyloxy)-GC (46). To a solution of 43 (11.4 mg, 15.7 mmol) in THF (0.20 mL) was added morpholine (6.8 mL, 78 mmol, 5 equiv). The mixture was stirred for 25 min and then quenched with aq. HCl (1 mL, 1M), extracted with EtOAc (3×) and dried with MgSO$_4$. The crude product was purified by flash chromatography (30-70% EtOAc/hexanes) to obtain 46 as a white solid (9.5 mg, 90%). $^1$H-NMR (300 MHz, CDCl$_3$) δ 7.36 (d, J=8.6 Hz, 2H$_{AR}$), 6.95 (d, J=8.6 Hz, 2H$_{AR}$), 6.02 (s, 1H, 12-H), 5.36 (d, J=9.3 Hz, 1H, benzyl), 5.30-5.19 (m, 2H, 6-H & 7-H), 4.95 (s, 1H, 10-H), 4.68 (d, J=9.3 Hz, 1H, benzyl), 4.48 (d, J=7.8 Hz, 1H, 2-H), 4.21 (d, J=7.8 Hz, 1H, 1-H), 3.82 (s, 3H, —OMe), 3.78-3.33 (m, 8H, morph.), 3.04 (q, J=7.0 Hz, 1H, 14-H), 2.85 (bs, 2H, 3-OH & 1-OH), 2.09-1.99 (m, 1H, 8-H), 1.30 (d, J=7.0 Hz, 3H, 16-CH$_3$), 1.16 (s, 9H, tBu); $^{13}$C-NMR (100 MHz, CDCl$_3$) δ 7.24, 29.23, 32.04, 41.45, 44.08 (morph.), 44.35 (morph.), 48.54, 55.14, 63.78, 66.29 (morph.), 66.36 (morph.), 67.38, 73.40, 73.76, 74.47, 74.76, 76.92, 83.15, 90.29, 98.04, 109.53, 114.45, 125.79, 130.13, 152.52, 160.11, 170.08, 170.48, 174.59; HRMS (FAB) calcd for C$_{33}$H$_{39}$O$_{14}$N 673.2371, found 673.2402.

7-(Piperidine-carbonyloxy)-10-(4-methoxy-benzyloxy)-GC (47). To a solution of 43 (14.2 mg, 19.5 mmol) in THF (0.20 mL) was added piperidine (5.8 mL, 59 mmol, 3 equiv). The mixture was stirred for 30 min and then quenched with aq. HCl (1 mL, 1M), extracted with EtOAc (3×) and dried with MgSO$_4$. The crude product was purified by flash chromatography (30-50% EtOAc/hexanes) to obtain 47 as a white solid (11.3 mg, 86%). $^1$H-NMR (400 MHz, CDCl$_3$) δ 7.36 (d, J=8.7 Hz, 2H$_{AR}$), 6.94 (d, J=8.7 Hz, 2H$_{AR}$), 6.01 (s, 1H, 12-H), 5.35 (d, J=9.3 Hz, 1H, benzyl), 5.29-5.20 (m, 2H, 6-H & 7-H), 4.95 (s, 1H, 10-H), 4.68 (d, J=9.3 Hz, 1H, benzyl), 4.48 (d, J=7.9 Hz, 1H, 2-H), 4.20 (dd, J=7.9, 3.4 Hz, 1H, 1-H), 3.81 (s, 3H, —OMe), 3.53-3.37 (m, 4H, piper.), 3.04 (q, J=7.0 Hz, 1H, 14-H), 2.95 (s, 1H, 3-OH), 2.86 (d, J=3.4 Hz, 1H, 1-OH), 2.03 (d, J=12.2 Hz, 1H, 8-H), 1.68-1.42 (m, 6H, piper.), 1.30 (d, J=7.0 Hz, 3H, 16-CH$_3$), 1.16 (s, 9H, tBu); $^{13}$C-NMR (100 MHz, CDCl$_3$) δ 7.51, 24.39 (piper.), 25.71 (piper.), 26.07 (piper.), 29.47, 32.27, 41.74, 45.25 (piper.), 48.80, 55.38, 64.03, 67.62, 73.60, 74.04, 74.44, 75.01, 77.41, 83.39, 90.59, 98.32, 109.85, 114.68, 126.09, 130.39, 152.74, 160.31, 170.47, 170.85, 174.96; HRMS (FAB) calcd for C$_{34}$H$_{40}$O$_{13}$N 670.2500, found 670.2526.

1-Methylcarbamoyloxy-10-(4-methoxy-benzyloxy)-GC (49). To a solution of 24 (11.1 mg, 19 mmol) in CH$_2$Cl$_2$ (120 mL) and iPr$_2$EtN (20.8 mL, 0.114 mmol, 6 equiv), was added solution of p-nitrophenyl chloroformate (12.0 mg, 57 mmol, 3 equiv) in CH$_2$Cl$_2$ (56 mL). The mixture was stirred for 15 min and MeNH$_2$ (2M in THF, 30 mL, 57 mmol, 3 equiv) and THF (50 mL) were added. The mixture was then stirred for additional 25 min and then quenched with aq. HCl (1 mL, 1M), extracted with EtOAc (3×) and dried with MgSO$_4$. The crude product was purified by flash chromatography (50-100% EtOAc/hexanes) to obtain 49 as a white solid (8.2 mg, 67%). $^1$H-NMR (400 MHz, CDCl$_3$, T=330K) δ 7.25-7.15 (m, 2H$_{AR}$), 6.90-6.80 (m, 2H$_{AR}$), 5.94 (s, 1H, 12-H), 5.53 (d, J=5.7 Hz, 1H, 1-H), 5.24 (d, J=11.1 Hz, 1H, benzyl), 5.18 (d, J=4.3 Hz, 1H, 6-H), 4.79 (s, 1H, 10-H), 4.69-4.54 (m, 2H, 2-H & benzyl), 4.39 (bs, 1H, —NH—), 4.32-4.21 (m, 1H, 7-H), 3.80 (s, 3H, —OMe), 3.19 (q, J=7.2 Hz, 1H, 14-H), 3.01 (s, 1H, 3-OH), 2.42 (bs, 3H, —CH$_3$), 2.19 (d, J=10.8 Hz, 1H, 7-OH), 1.68 (d, J=12.3 Hz, 1H, 8-H), 1.30 (d, J=7.2 Hz, 3H, 16-CH$_3$), 1.13 (s, 9H, tBu); $^{13}$C-NMR (75 MHz, CD$_3$OD, T=320K) δ 9.42, 27.31, 29.63, 33.17, 42.59, 51.35, 55.86, 66.20, 68.12, 73.68, 76.12, 77.03, 77.21, 81.36, 85.44, 94.34, 102.23, 110.68, 114.84, 114.94, 130.42, 156.56, 161.06, 172.52, 172.80, 177.90; HRMS (FAB) calcd for C$_{30}$H$_{34}$O$_{13}$N 616.2030, found 616.2028.

1-tert-Butylcarbamoyloxy-10-(4-methoxy-benzyloxy)-GC (50). To a solution of 24 (9.3 mg, 16.6 mmol) in CH$_2$Cl$_2$ (110 mL) and iPr$_2$EtN (17.4 mL, 99 mmol, 6 equiv), was added solution of p-nitrophenyl chloroformate (10.0 mg, 50 mmol, 3 equiv) in CH$_2$Cl$_2$ (40 mL). The mixture was stirred for 15 min and tBuNH$_2$ (17.4 mL, 166 mmol, 10 equiv) and THF (100 mL) were added. The mixture was then stirred for additional 12 h and then quenched with aq. HCl (1 mL, 1M), extracted with EtOAc (3×) and dried with MgSO$_4$. The crude product was purified by flash chromatography (40-100% EtOAc/hexanes) to obtain 50 as a white solid (6.6 mg, 60%). $^1$H-NMR (400 MHz, CDCl$_3$) δ 7.23 (d, J=8.6 Hz, 2H$_{AR}$), 6.86 (d, J=8.6 Hz, 2H$_{AR}$), 5.91 (s, 1H, 12-H), 5.55 (d, J=4.6 Hz, 1H, 1-H), 5.21 (d, J=4.3 Hz, 1H, 6-H), 5.15 (d, J=11.8 Hz, 1H, benzyl), 4.82 (bd, J=11.8 Hz, 1H, benzyl), 4.75 (s, 1H, 10-H), 4.67 (d, J=5.0 Hz, 1H, 2-H), 4.62 (bs, 1H, —NH—), 4.30-4.19 (m, 1H, 7-H), 3.80 (s, 3H, —OMe), 3.23 (bs, 1H, 3-OH), 3.20 (q, J=7.3 Hz, 1H, 14-H), 2.17 (d, J=11.8 Hz, 1H, 7-OH), 1.63 (d, J=12.3 Hz, 1H, 8-H), 1.32 (d, J=7.3 Hz, 3H, 16-CH$_3$), 1.19 (s, 9H, tBu), 1.01 (s, 9H, tBu); $^{13}$C-NMR (75 MHz, CDCl$_3$) δ 8.68, 28.72, 29.02, 32.20, 41.06, 50.51, 50.92, 55.31, 65.29, 66.83, 72.16, 73.96, 75.27, 80.41, 84.41, 92.26, 100.34, 108.79, 113.88, 127.77, 130.14, 151.70, 159.72, 170.25, 171.01, 174.94; HRMS (FAB) calcd for C$_{33}$H$_{40}$O$_{13}$N 658.2500, found 658.2516.

1-(Morpholine-4-carbonyloxy)-10-(4-methoxy-benzyloxy)-GC (51). To a solution of 24 (10.8 mg, 19.3 mmol) in CH$_2$Cl$_2$ (118 mL) and iPr$_2$EtN (20.3 mL, 116 mmol, 6 equiv), was added solution of p-nitrophenyl chloroformate (11.7 mg, 58 mmol, 3 equiv) in $CH_2Cl_2$ (55 mL). The mixture was stirred for 15 min and morpholine (13.5 mL, 154 mmol, 8 equiv) and THF (100 mL) were added. The mixture was then stirred for additional 35 min and then quenched with aq. HCl (1 mL, 1M), extracted with EtOAc (3×) and dried with $MgSO_4$. The crude product was purified by flash chromatography (50-100% EtOAc/hexanes) to obtain 51 as a white solid (9.8 mg, 75%). $^1$H-NMR (400 MHz, $CDCl_3$) δ 7.20 (d, J=8.5 Hz, $2H_{AR}$), 6.88 (d, J=8.5 Hz, $2H_{AR}$), 5.97 (s, 1H, 12-H), 5.57 (d, J=5.3 Hz, 1H, 1-H), 5.23 (d, J=11.0 Hz, 1H, benzyl), 5.11 (d, J=4.3 Hz, 1H, 6-H), 4.82 (s, 1H, 10-H), 4.71 (d, J=5.3 Hz, 1H, 2-H), 4.62 (d, J=11.0 Hz, 1H, benzyl), 4.32-4.21 (m, 1H, 7-H), 3.82 (s, 3H, —OMe), 3.57 (s, 1H, 3-OH), 3.54-3.33 (m, 5H, morph.), 3.31-3.18 (m, 1H, morph.), 3.21 (q, J=7.2 Hz, 1H, 14-H), 2.89-2.66 (m, 2H, morph.), 2.39 (d, J=11.7 Hz, 1H, 7-OH), 1.69 (d, J=12.3 Hz, 1H, 8-H), 1.32 (d, J=7.2 Hz, 3H, 16-$CH_3$), 1.15 (s, 9H, tBu); $^{13}$C-NMR (75 MHz, $CDCl_3$) δ 8.49, 29.14, 32.33, 41.16, 43.84 (morph.), 50.41, 55.41, 65.12, 65.94 (morph.), 66.21 (morph.), 66.68, 72.83, 74.97, 75.54, 76.28, 80.20, 84.25, 92.15, 100.08, 108.99, 113.97, 128.01, 129.64, 152.38, 159.75, 170.21, 170.66, 175.06; HRMS (FAB) calcd for $C_{33}H_{38}O_{14}N$ 672.2292, found 672.2307.

1-(Piperidine-carbonyloxy)-10-(4-methoxy-benzyloxy)-GC (52). To a solution of 24 (10.9 mg, 19.4 mmol) in $CH_2Cl_2$ (119 mL) and $iPr_2EtN$ (20.3 mL, 116 mmol, 6 equiv), was added solution of p-nitrophenyl chloroformate (11.7 mg, 58 mmol, 3 equiv) in $CH_2Cl_2$ (55 mL). The mixture was stirred for 15 min and piperidine (15.4 mL, 155 mmol, 8 equiv) and THF (100 ml) were added. The mixture was then stirred for additional 30 min and then quenched with aq. HCl (1 mL, 1M), extracted with EtOAc (3×) and dried with $MgSO_4$. The crude product was purified by flash chromatography (40-70% EtOAc/hexanes) to obtain 52 as a white solid (6.9 mg, 53%). $^1$H-NMR (400 MHz, $CDCl_3$) δ 7.20 (d, J=8.6 Hz, $2H_{AR}$), 6.87 (d, J=8.6 Hz, $2H_{AR}$), 5.95 (s, 1H, 12-H), 5.54 (d, J=5.0 Hz, 1H, 1-H), 5.22 (d, J=11.0 Hz, 1H, benzyl), 5.10 (d, J=4.4 Hz, 1H, 6-H), 4.80 (s, 1H, 10-H), 4.72 (d, J=5.0 Hz, 1H, 2-H), 4.64 (d, J=11.0 Hz, 1H, benzyl), 4.32-4.22 (m, 1H, 7-H), 3.81 (s, 3H, —OMe), 3.55 (s, 1H, 3-OH), 3.52-3.40 (m, 1H, piper.), 3.32-3.19 (m, 1H, piper.), 3.22 (q, J=7.3 Hz, 1H, 14-H), 2.77-2.56 (m, 2H, piper.), 2.25 (d, J=12.0 Hz, 1H, 7-OH), 1.68 (d, J=12.3 Hz, 1H, 8-H), 1.63-1.50 (m, 1H, piper.), 1.49-1.29 (m, 5H, piper.), 1.32 (d, J=7.3 Hz, 3H, 16-$CH_3$), 1.14 (s, 9H, tBu); $^{13}$C-NMR (75 MHz, $CDCl_3$) δ 8.68, 23.98 (piper.), 25.09 (piper.), 25.56 (piper.), 29.15, 32.31, 41.11, 44.62 (piper.), 44.84 (piper.), 50.53, 55.36, 65.25, 66.95, 72.68, 74.77, 75.56, 76.45, 80.38, 84.36, 92.18, 100.36, 108.86, 113.88, 128.07, 129.89, 152.37, 159.63, 170.20, 170.81, 174.88; HRMS (FAB) calcd for $C_{34}H_{40}O_{13}N$ 670.2500, found 670.2510.

7-Methylcarbamoyloxy-GC (53). To a solution of 44 (5.3 mg, 8.7 mmol) in acetonitrile (108 mL) and $CHCl_3$ (35 mL) was added aq. solution of $(NH_4)_2Ce(NO_3)_6$ (10.6 mL, 17.3 mmol, 2 equiv, 1.63M). The mixture was stirred for 1.5 h, aq. solution of $(NH_4)_2Ce(NO_3)_6$ (5.3 mL, 8.7 mmol, 1 equiv, 1.63M) was added and mixture was further stirred for 12 h. Volatiles were removed under reduced pressure and residue was purified by flash chromatography (40-99% EtOAc/1% AcOH/hexanes) to obtain 53 as a white powder (3.0 mg, 69%). $^1$H-NMR (300 MHz, 315K, $CD_3OD$) δ 6.11 (s, 1H, 12-H), 5.32 (d, J=4.3 Hz, 1H, 6-H), 5.18 (dd, J=12.8, 4.3 Hz, 1H, 7-H), 5.13 (s, 1H, 10-H), 4.54 (d, J=7.6 Hz, 1H, 2-H), 4.18 (d, J=7.6 Hz, 1H, 1-H), 3.00 (q, J=7.0 Hz, 1H, 14-H), 2.74 (s, 3H, $CH_3$), 2.00 (d, J=12.9 Hz, 1H, 8-H), 1.22 (d, J=7.0 Hz, 3H, 16-$CH_3$), 1.14 (s, 9H, tBu); HSQC correlation data in the Supporting Information; HRMS (FAB) calcd for $C_{22}H_{28}O_{12}N$ 498.1612, found 498.1633.

7-tert-Butylcarbamoyloxy-GC (54). To a solution of 45 (5.7 mg, 8.6 mmol) in acetonitrile (108 mL) and $CHCl_3$ (35 mL) was added aq. solution of $(NH_4)_2Ce(NO_3)_6$ (10.6 mL, 17.3 mmol, 2 equiv, 1.63M). The mixture was stirred for 1.5 h, aq. solution of $(NH_4)_2Ce(NO_3)_6$ (5.3 mL, 8.7 mmol, 1 equiv, 1.63M) was added and mixture was further stirred for 12 h. Volatiles were removed under reduced pressure and residue was purified by flash chromatography (40-70% EtOAc/1% AcOH/hexanes) to obtain 54 as a white powder (3.7 mg, 80%). $^1$H-NMR (400 MHz, $CDCl_3$) δ 6.01 (bs, 1H, OH), 5.98 (s, 1H, 12-H), 5.42 (m, 1H, 6-H), 5.16 (dd, J=12.8, 4.1 Hz, 1H, 7-H), 5:14 (s, 1H, 10-H), 4.96 (s, 1H, —NH—), 4.69 (d, J=7.9 Hz, 1H, 2-H), 4.32 (bd, J=7.9 Hz, 1H, 1-H), 4.23 (bs, 2H, OH), 3.14 (bq, J=7.1 Hz, 1H, 14-H), 1.98 (d, J=12.8 Hz, 1H, 8-H), 1.31 (s, 9H, tBu), 1.27 (d, J=7.1 Hz, 3H, 16-$CH_3$), 1.10 (s, 9H, tBu); HSQC correlation data in the Supporting Information; HRMS (FAB) calcd for $C_{25}H_{34}O_{12}N$ 540.2081, found 540.2098.

7-(Morpholine-4-carbonyloxy)-GC (55). To a solution of 46 (5.8 mg, 8.7 mmol) in acetonitrile (108 mL) and $CHCl_3$ (35 mL) was added aq. solution of $(NH_4)_2Ce(NO_3)_6$ (10.6 mL, 17.3 mmol, 2 equiv, 1.63M). The mixture was stirred for 1.5 h, aq. solution of $(NH_4)_2Ce(NO_3)_6$ (5.3 mL, 8.7 mmol, 1 equiv, 1.63M) was added and mixture was further stirred for 12 h. Volatiles were removed under reduced pressure and residue was purified by flash chromatography (50-99% EtOAc/1% AcOH/hexanes) to obtain 55 as a white powder (2.9 mg, 60%). $^1$H-NMR (400 MHz, $CD_3OD$) δ 6.14 (s, 1H, 12-H), 5.34 (d, J=4.4 Hz, 1H, 6-H), 5.24 (dd, J=12.8, 4.4 Hz, 1H, 7-H), 5.15 (s, 1H, 10-H), 4.54 (d, J=7.6 Hz, 1H, 2-H), 4.18 (d, J=7.6 Hz, 1H; 1-H), 3.73 -3.37 (m, 8H, morph.), 3.00 (q, J=7.1 Hz, 1H, 14-H), 2.06 (d, J=12.8 Hz, 1H, 8-H), 1.22 (d, J=7.1 Hz, 3H, 16-$CH_3$), 1.15 (s, 9H, tBu); HSQC correlation data in the Supporting Information; HRMS (FAB) calcd for $C_{25}H_{32}O_{13}N$ 554.1874, found 554.1874.

7-(Piperidine-carbonyloxy)-GC (56). To a solution of 47 (5.8 mg, 8.6 mmol) in acetonitrile (108 mL) and $CHCl_3$ (35 mL) was added aq. solution of $(NH_4)_2Ce(NO_3)_6$ (10.6 mL, 17.3 mmol, 2 equiv, 1.63M). The mixture was stirred for 1.5 h, aq. solution of $(NH_4)_2Ce(NO_3)_6$ (5.3 mL, 8.7 mmol, 1 equiv, 1.63M) was added and mixture was further stirred for 12 h. Volatiles were removed under reduced pressure and residue was purified by flash chromatography (40-70% EtOAc/1% AcOH/hexanes) to obtain 56 as a white powder (3.0 mg, 64%). $^1$H-NMR (400 MHz, $CDCl_3$) δ 6.21 (bs, 1H, OH), 5.98 (s, 1H, 12-H), 5.41 (m, 1H, 6-H), 5.25 (dd, J=12.8, 4.3 Hz, 1H, 7-H), 5.14 (s, 1H, 10-H), 4.68 (d, J=7.9 Hz, 1H, 2-H), 4.36 (bs, 1H, OH), 4.32 (bd, J=7.9 Hz, 1H, 1-H), 3.55-3.26 (m, 4H, piper.), 3.15 (m, 1H, 14-H), 2.04 (d, J=12.8 Hz, 1H, 8-H), 1.75-1.40 (m, 6H, piper.), 1.26 (d, J=7.0 Hz, 3H, 16-$CH_3$), 1.11 (s, 9H, tBu); HSQC HSQC correlation data in the Supporting Information; HRMS (FAB) calcd for $C_{26}H_{34}O_{12}N$ 552.2081, found 552.2067.

1-Methylcarbamoyloxy-GC (57). To a solution of 49 (3.5 mg, 5.6 mmol) in acetonitrile (70 mL) and $CHCl_3$ (23 mL) was added aq. solution of $(NH_4)_2Ce(NO_3)_6$ (6.9 mL, 11.2 mmol, 2 equiv, 1.63M). The mixture was stirred for 6.5 h, aq. solution of $(NH_4)_2Ce(NO_3)_6$ (6.9 mL, 11.2 mmol, 2 equiv, 1.63M) was added and the mixture was further stirred for 12 h. Volatiles were removed under reduced pressure and the residue was purified by flash chromatography (70-99% EtOAc/1% AcOH/hexanes) to obtain 57 as a white powder (2.4 mg, 86%). $^1$H-NMR (400 MHz, $CD_3OD$) δ 6.06 (s, 1H, 12-H), 5.46 (d, J=5.3 Hz, 1H, 1-H), 5.22 (d, J=4.1 Hz, 1H, 6-H), 5.07 (s, 1H, 10-H), 4.66 (d, J=5.5 Hz, 1H, 2-H), 4.31

(dd, J=12.6, 4.1 Hz, 1H, 7-H), 3.10 (q, J=7.2 Hz, 1H, 14-H), 2.83-2.68 (m, 3H, —CH$_3$), 1.78 (d, J=12.5 Hz, 1H, 8-H), 1.27 (d, J=7.2 Hz, 3H, 16-CH$_3$), 1.22 (s, 9H, tBu); HSQC correlation data in the Supporting Information; HRMS (FAB) calcd for C$_{22}$H$_{28}$O$_{12}$N 498.1612, found 498.1618.

1-tert-Butylcarbamoyloxy-GC (58). To a solution of 50 (3.7 mg, 5.6 mmol) in acetonitrile (70 mL) and CHCl$_3$ (23 mL) was added aq. solution of (NH$_4$)$_2$Ce(NO$_3$)$_6$ (6.9 mL, 11.2 mmol, 2 equiv, 1.63M). The mixture was stirred for 6 h, aq. solution of (NH$_4$)$_2$Ce(NO$_3$)$_6$ (6.9 mL, 11.2 mmol, 2 equiv, 1.63M) was added and the mixture was further stirred for 12 h. Volatiles were removed under reduced pressure and the residue was purified by flash chromatography (40-70% EtOAc/hexanes) to obtain 58 as a white powder (2.5 mg, 84%). $^1$H-NMR (400 MHz, CD$_3$OD) δ 6.05 (s, 1H, 12-H), 5.45 (d, J=5.1 Hz, 1H, 1-H), 5.28 (d, J=4.2 Hz, 1H, 6-H), 5.06 (s, 1H, 10-H), 4.64 (d, J=5.1 Hz, 1H, 2-H), 4.33 (dd, J=12.4, 4.2 Hz, 1H, 7-H), 3.10 (q, J=7.3 Hz, 1H, 14-H), 1.77 (d, J=12.4 Hz, 1H, 8-H), 1.34 (s, 9H, tBu), 1.27 (d, J=7.3 Hz, 3H, 16-CH$_3$), 1.22 (s, 9H, tBu); HSQC correlation data in the Supporting Information; HRMS (FAB) calcd for C$_{25}$H$_{34}$O$_{12}$N 540.2081, found 540.2075.

1-(Morpholine-4-carbonyloxy)-GC (59). To a solution of 51 (6.5 mg, 9.6 mmol) in acetonitrile (120 mL) and CHCl$_3$ (39 mL) was added aq. solution of (NH$_4$)$_2$Ce(NO$_3$)$_6$ (11.8 mL, 19.2 mmol, 2 equiv, 1.63M). The mixture was stirred for 6.5 h, aq. solution of (NH$_4$)$_2$Ce(NO$_3$)$_6$ (11.8 mL, 19.2 mmol, 2 equiv, 1.63M) was added and the mixture was further stirred for 12 h. Volatiles were removed under reduced pressure and the residue was purified by flash chromatography (70-99% EtOAc/1% AcOH/hexanes) to obtain 59 as a white powder (4.3 mg, 80%). $^1$H-NMR (400 MHz, CD$_3$OD) δ 6.10 (s, 1H, 12-H), 5.39 (d, J=6.6 Hz, 1H, 1-H), 5.22 (d, J=4.2 Hz, 1H, 6-H), 5.09 (s, 1H, 10-H), 4.74 (d, J=6.6 Hz, 1H, 2-H), 4.28 (dd, J=12.4, 4.2 Hz, 1H, 7-H), 3.76-3.62 (m, 4H, morph.), 3.58-3.38 (m, 4H, morph.), 3.12 (q, J=7.1 Hz, 1H, 14-H), 1.79 (d, J=12.4 Hz, 1H, 8-H), 1.28 (d, J=7.1 Hz, 3H, 16-CH$_3$), 1.22 (s, 9H, tBu); HSQC correlation data in the Supporting Information; HRMS (FAB) calcd for C$_{25}$H$_{32}$O$_{13}$N 554.1874, found 554.1874.

1-(Piperidine-carbonyloxy)-GC (60). To a solution of 52 (3.8 mg, 5.6 mmol) in acetonitrile (70 mL) and CHCl$_3$ (23 mL) was added aq. solution of (NH$_4$)$_2$Ce(NO$_3$)$_6$ (6.9 mL, 11.2 mmol, 2 equiv, 1.63M). The mixture was stirred for 6.5 h, aq. solution of (NH$_4$)$_2$Ce(NO$_3$)$_6$ (6.9 mL, 11.2 mmol, 2 equiv, 1.63M) was added and the mixture was further stirred for 12 h. Volatiles were removed under reduced pressure and the residue was purified by flash chromatography (50-100% EtOAc/hexanes) to obtain 60 as a white powder (2.5 mg, 79%). $^1$H-NMR (400 MHz, CD$_3$OD) δ 6.09 (s, 1H, 12-H), 5.40 (d, J=6.4 Hz, 1H, 1-H), 5.22 (d, J=4.2 Hz, 1H, 6-H), 5.08 (s, 1H, 10-H), 4.71 (d, J=6.4 Hz, 1H, 2-H), 4.32 (dd, J=12.4, 4.2 Hz, 1H, 7-H), 3.68-3.50 (m, 2H, piper.), 3.46-3.20 (m, 2H, piper.), 3.12 (q, J=7.2 Hz, 1H, 14-H), 1.79 (d, J=12.4 Hz, 1H, 8-H), 1.75-1.52 (m, 6H, piper.), 1.28 (d, J=7.2 Hz, 3H, 16-CH$_3$), 1.22 (s, 9H, tBu); HSQC correlation data in the Supporting Information; HRMS (FAB) calcd for C$_{26}$H$_{34}$O$_{12}$N 552.2081, found 552.2061.

10-benzyloxy-isoGC-1,6-carbonate (61): To a solution of 16 (9.6 mg, 18.2 mol) in CH$_2$Cl$_2$ (113 □L) and iPr$_2$EtN (19.1 L, 0.109 mmol, 6 equiv), was added solution of p-nitrophenyl chloroformate (11.0 mg, 54.6 □mol, 3 equiv) in CH$_2$Cl$_2$ (50 L). The mixture was stirred for 15 min and then quenched with aq. HCl (1 mL, 1M), extracted with EtOAc (3×) and dried with MgSO$_4$. The crude product was purified by flash chromatography (30-50% EtOAc/hexanes) to obtain 61 as a white solid (9.3 mg, 92% yield, 82% purity). $^1$H NMR (300 MHz, CDCl$_3$): δ=7.45-7.28 (m, 5H$_{AR}$), 5.82 (s, 1H), 5.63 (s, 1H), 5.49 (d, J=10.6 Hz, 1H), 5.05 (s, 1H), 4.88 (d, J=4.0 Hz, 1H), 4.79 (d, J=10.6 Hz, 1H), 4.76 (d, J=4.0 Hz, 1H), 4.73 (s, 1H), 3.26 (q, J=7.8 Hz, 1H), 2.96 (s, 1H), 2.28 (s, 1H), 1.35 (d, J=7.8 Hz, 3H), 1.11 (s, 9H, tBu). MS (FAB) calcd for C$_{28}$H$_{29}$O$_{12}$ 557.17, found 557.56.

Biological Testing

Functional glycine receptor assay. Pharmacological activities of the compounds were evaluated in a FLIPR® Membrane Potential Assay (Molecular Deives, Crawley, UK) using a HEK293 cell line stably expressing the human homomeric α1 GlyR.[53] Briefly, α1 GlyR-HEK293 cells were split into poly-D-lysine-coated 96-well black Opti-plates (Packard). 16-24 h later, the medium was aspirated, and 100 mL KREBS Buffer [140 mM NaCl/4.7 mM KCl/2.5 mM CaCl$_2$/1.2 mM MgCl$_2$/10 mM HEPES/11 mM D-Glucose, pH 7.4] supplemented with FLIPR® Membrane Potential Assay loading dye and various concentrations of the test compounds was added to the wells. The plate was incubated at 37° C. in a humidified 5% CO$_2$ incubator for 30 min and assayed in a NOVOstar™ (BMG Labtechnologies, Offenburg, Germany) measuring emission at 560 nm caused by a 530 nm excitation. Fluorescence measurements were performed immediately before and up to 1 min. after addition of glycine (final concentration 100 mM) to the wells. The experiments were performed in duplicate at least three times for each compound. Percentage inhibition was calculated as: (Response$_{glycine}$ −Response$_{test\ cmpd+glycine}$)/Response$_{glycine}$. Inhibition below 20% is characterized as no inhibition (NI).

Results

Synthesis

Ginkgolide C (GC, 3, FIG. 1) was chosen as the starting material as it carries the most hydroxyl groups of the ginkgolides, thus providing possibilities for a more diverse library. Secondly, GC (3), together with GB (2), is the most potent ginkgolide GlyR antagonists (Stromgaard, 2003).

Solid-phase synthesis. The use of solid-phase synthesis (SPS) for the preparation of ginkgolide derivatives appeared to be particularly attractive, as the lack of chromophores renders them difficult to handle in solution. Moreover, the presence of multiple hydroxyl groups provides several possibilities of solid-phase attachment. GC (3) has four different hydroxyl groups, three secondary and one tertiary, which exhibit different reactivities and can therefore be functionalized selectively. In general, 10-OH is the most reactive for alkylation and esterification (Corey, 1992). However, acid catalyzed esterification (Jaracz, 2002), as well as reaction of GC (3) with alkyl and aryl sulfonyl halides takes place at 7-OH (Cazaux, 1995; Vogensen, 2003) a selective silylation at 1-OH has also been described (Weingers, 1991).

Initially, attempts were made to use a silicon linker, which could be attached selectively to 1-OH of GC (3), followed by selective derivatizations of 10-OH, 7-OH, and if possible 3-OH. In a previous example of selective derivatization of 1-OH, the bulky tert-butyldiphenylsilyl was used as a protection group, which however prevented further derivatization at 10-OH (Weinges, 1991). Hence, it was envisaged that decreasing the bulk of the silicon linker could allow further derivatization of 10-OH. Three silicon linkers with variation in the steric bulk at silicon were synthesized according to known procedures (Chan, 1985; Randolph, 1995). Interestingly, isopropyl substituents on the silicon linker as in entry 1 (Table 1) reacted selectively at 1-OH, while decreasing the size of the substituents led to preferential reaction at 7-OH. These linkers, however, were unstable as evidenced by leaching from the resin, and no further studies were pursued.

TABLE 1

Attachment of GC to silyl resins; mode of attachment.

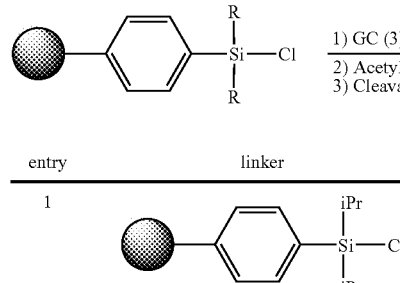

| entry | linker | loading[a] (mmol/g) | mode of attachment[b] |
|---|---|---|---|
| 1 | ⬢—⟨⟩—Si(iPr)₂—Cl | 0.85 | 1-OH |
| 2 | ⬢—⟨⟩—Si(Et)₂—Cl | 0.52 | 1-OH/7-OH (2:1) |
| 3 | ⬢—⟨⟩—Si(Me)₂—Cl | 0.35 | 7-OH |
| 4[c] | ⬢—⟨⟩—(-)₃—Si(Et)₂—Cl | 1.5 | — |

[a] Loading determined by attachment of Disperse Red, cleavage and spectrophotometric measurements.
[b] Mode of attachment determined by acetylation, cleavage and ¹H-NMR spectra of cleaved compounds. Leaching detected with linkers in entries 2-4.
[c] Prepared from commercial DES resin.

Alternatively, the use of a sulfonyl linkage was studied by anchoring GC (3) through 7-OH, followed by selective derivatization at 10-OH and/or 1-OH and nucleophilic cleavage to provide derivatives of GB (2), and GC (3) with an inverted C-7 configuration. Therefore, a pipsyl moiety was introduced at 7-OH of GC (3) to form 7-O-pipsyl-GC (6) (Scheme 1), which was then attached to a TentaGel-NH₂ resin using Pd-catalyzed carbonylation, similar to that described by Takahashi et al (Takahashi, 2001) to give 7 (Scheme 1).

Scheme 1

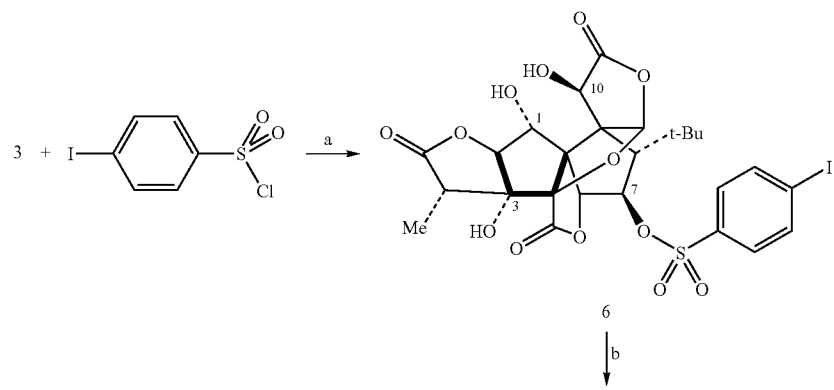

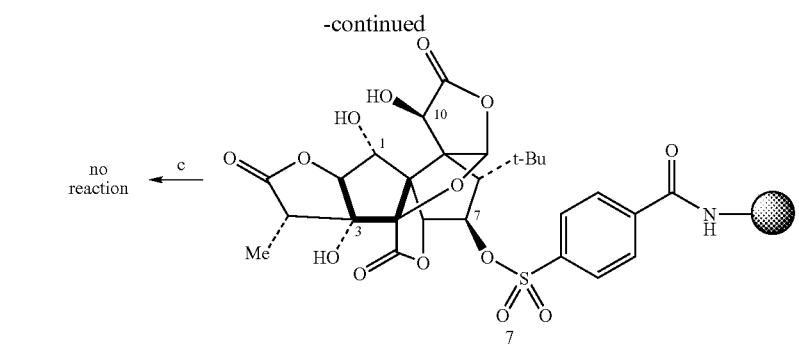

a pyridine, CH$_2$Cl$_2$;
b Tentagel-NH$_2$, CO, Et$_3$N, Pd(PPh$_3$)$_4$, DMF;
c TBAH or TBAF, THF Scheme 1. Attachment of ginkgolide C to solid-phase via sulfonyl linker.

However, treatment of 7 with nucleophiles such as tetrabutyl ammonium fluoride (TBAF) or tetrabutyl ammonium hydride (TBAH) did not release any ginkgolide derivatives. In addition, the solution-phase version of the same displacement of 7-O-pipsyl-GC (6) gave none of the desired products either, thus suggesting that the 7-O-sulfonyl group is not a sufficiently good leaving group as opposed to a trifoliate group (Vogensen, 2003). Attachment of GC through 1-OH or 3-OH using other methods did not lead to success probably due to steric hindrance. In addition, substituents at 3-OH readily undergo elimination leading to a thermodynamically favored a,b unsaturated lactone F (Weinges, 1987).

Instead of direct attachment of GC (3) to the solid-phase, attachment via a building block was considered. Ideally, such a building block should function as a multidetachable linker, so that depending on cleavage conditions, ginkgolide derivatives with or without the first building block could be generated. Since GC (3) can be selectively and efficiently benzylated at 10-OH with benzyl bromide under mild conditions in solution (Vogensen, 2003), a benzyl group could serve as the first building block, followed by derivatization of 7-OH, translactonization to form C-6 iso-GC derivatives, removal of 7-OH to reroute into GB derivatives, and if possible functionalize 1-OH and 3-OH, as well. Immobilization of benzyl bromide was investigated in various manners. Initially 4-(bromomethyl)-phenylacetic acid was anchored to the Wang resin and Rink amide resin to give 8 and 9, respectively (Scheme 2). The immobilized benzyl bromides were then reacted with GC (3) to give resins 10 and 11. Cleavage with TFA produced GC derivatives 12 and 13, respectively, which revealed that GC (3) was attached at 10-OH with a high selectivity. The purity of the cleaved products was >90% as determined by $^1$H-NMR. Benzyl bromide can also be immobilized to a silicon linker (Plunkett, 1995) representing a traceless linkage, which was also investigated. Resin 14 was synthesized in three steps from bromopolystyrene and 4-(allyldimethylsilyl)benzyl alcohol (Lee, 2001; Iglesias, 2001) followed by reaction with GC (3) to provide resin-bound 10-0-benzyl-GC 15 (Scheme 2). Cleavage with TFA provided 16 in 85% purity.

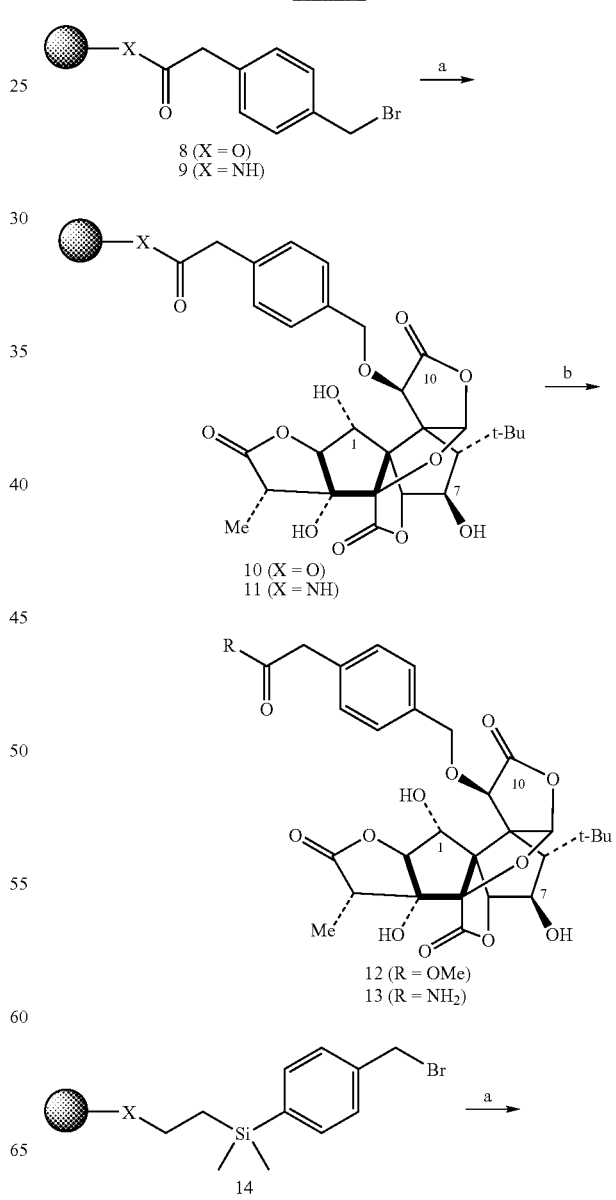

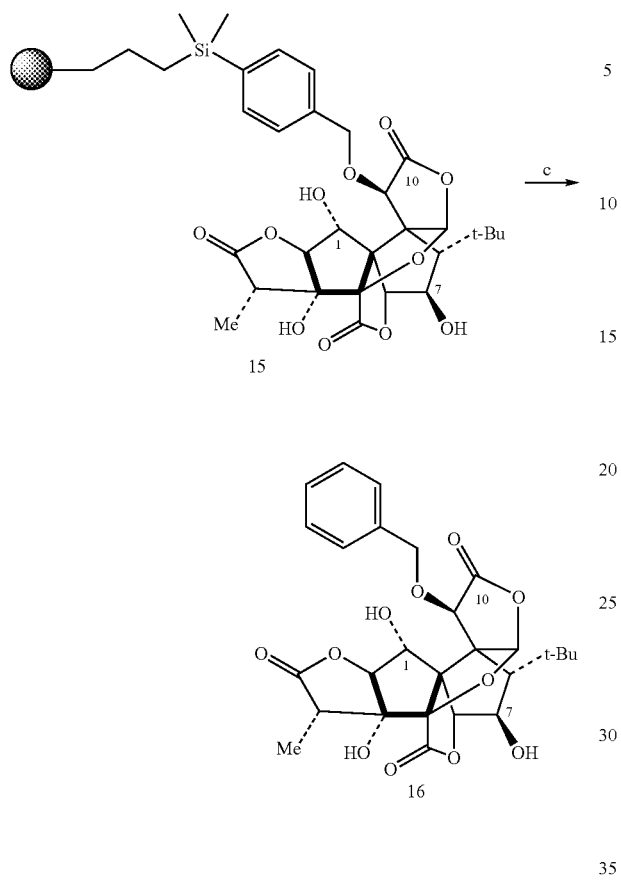

a 3, K$_2$CO$_3$, DMF;
b Wang resin: i. TFA/CH$_2$Cl$_2$, ii. CH$_2$N$_2$; Rink-amide resin: TFA/H$_2$O;
c TFA/CH$_2$Cl$_2$ Scheme 2. Attachment of ginkgolide C to a solid-phase via 10-O-benzyl using either Wang resin, Rink amide resin, or traceless silicon linker.

The benzylated Wang resin was selected for further investigation as it provided sufficiently pure products. Selective hydroxyl group functionalizations were studied and compared with similar reactions in solution. Treatment of resin-bound ginkgolide 10 with benzoic anhydride and Hünig's base resulted in a mixture of iso-GC benzoates and unreacted starting material (Scheme 3). On the other hand, solution-phase reaction of 10-O-benzyl-GC (16) under similar conditions produced iso-GC monobenzoate 17 as the major product.

Figure 2:
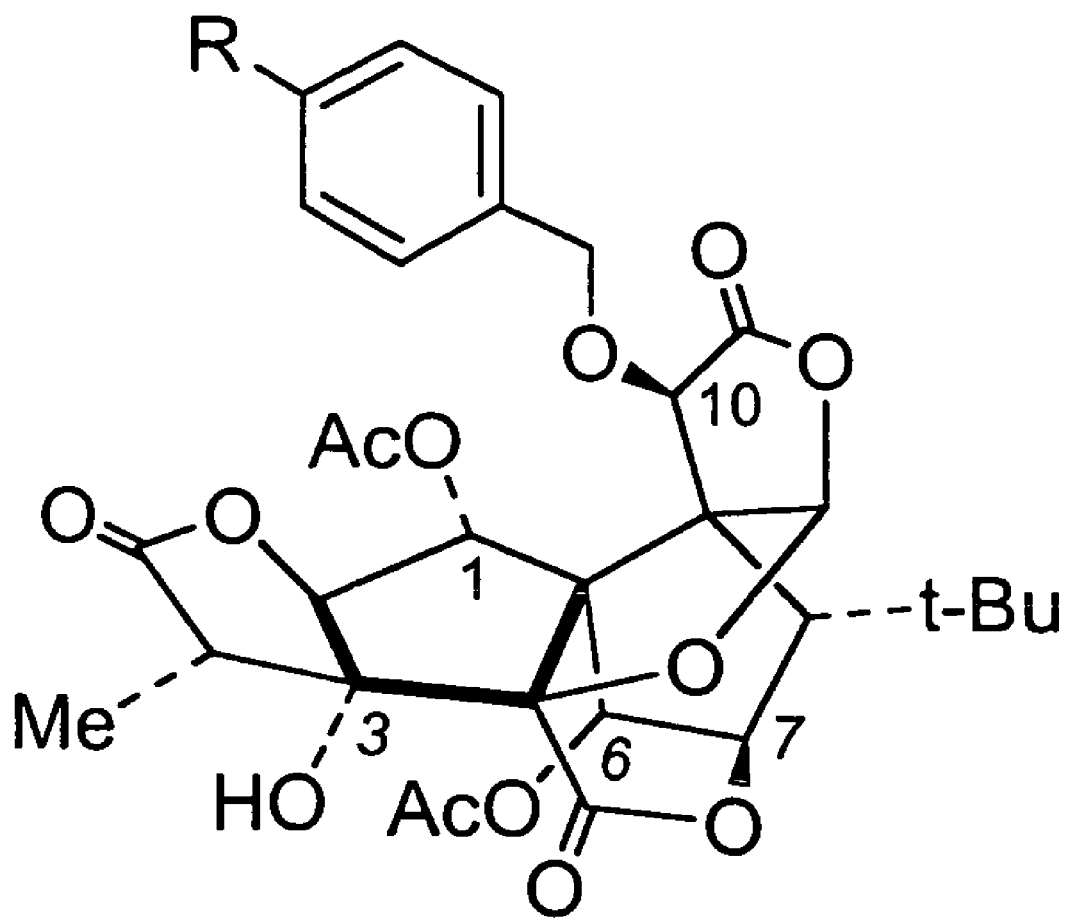
FIG. 2. 10-Alkyl-iso-GC-1,6-bisacetates.

Acetylation of resin 10 with Ac$_2$O in the presence of Hünig's base provided iso-GC-bisacetate 18 in a purity of only ca. 60%, while the same reaction in solution provided iso-GC-bisacetate 19 in 90% purity (FIG. 2). Similarly, several other reactions on solid-phase such as transformation of GC into GB (Cazaux, 1995; Weinges, 1991) either failed entirely, or proceeded with very low conversion and purity, as compared to the same reaction in solution. It became clear that a solid-phase strategy is not suited for the preparation of a ginkgolide derivative library.

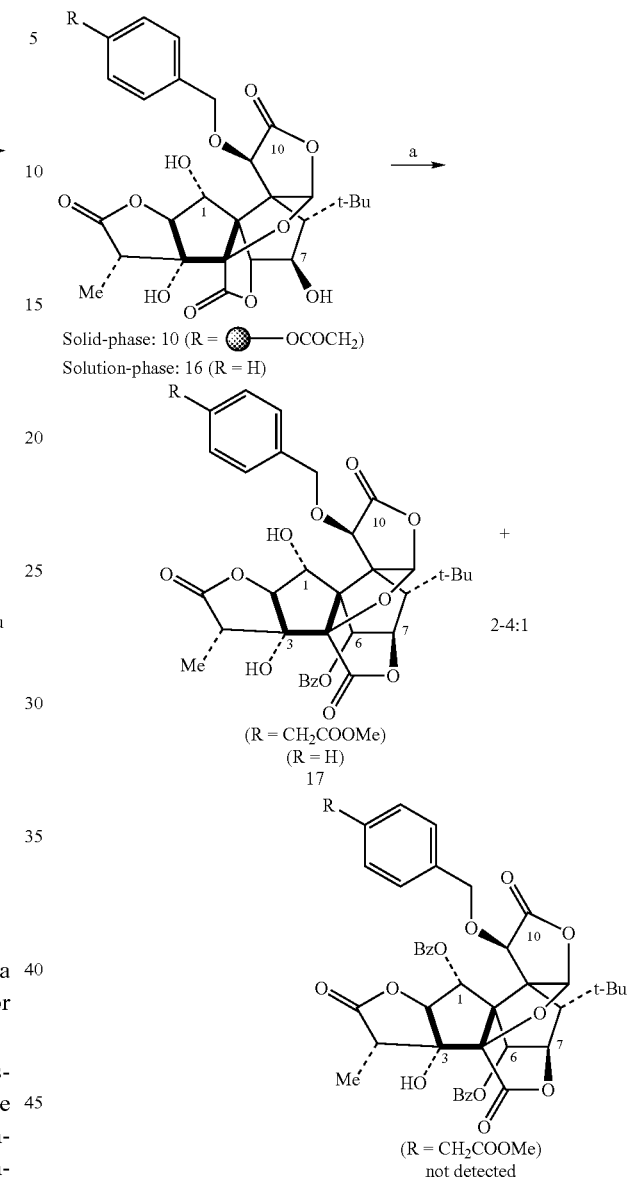

a Solid-phase: i. Bz$_2$O, iPr$_2$EtN, CH$_2$Cl$_2$, ii. TFA/CH$_2$Cl$_2$, iii. CH$_2$N$_2$,
Solution-phase: Bz$_2$O, iPr$_2$EtN, CH$_2$Cl$_2$.

Scheme 3. Comparison of ginkgolide C benzoylation using solid-phase or solution-phase chemistry.

Solution-Phase Synthesis. Because of the limitations in solid-phase strategy, further derivatizations were performed by solution-phase chemistry. 10-O-benzyl-GC (16) turned out to be a suitable precursor for a wide variety of transformations (Scheme 4). GC-7-benzoate (21) was prepared from 16 by reaction with benzoyl chloride and pyridine in CH$_2$Cl$_2$ in 79% yield. Iso-GC-6-benzoate 17 was efficiently formed (77% yield) by exchanging pyridine with Hünig's base. This remarkable difference in reaction pattern is associated with stabilization of a translactonized anion intermediate by hydrogen bonding with 3-OH as reported previously (Jaracz, 2002). Iso-GC-1,6-bisbenzoate 22 was also prepared in 64% yield by further increasing the amount of benzoylation reagent and prolonging the reaction time. Heating of benzoate 17 with Hünig's base in DMF to 100° C. for 1.5 h lead to a remarkable migration of benzoate from C-6 to C-1 with subsequent translactonization of the iso-GC skeleton back to the GC skeleton to form 23 (78% yield, Scheme 4). The driving force for this rearrangement is the greater thermodynamic stability of the original ginkgolide core. Namely, the bulky tert-butyl group is axial in iso-GC while it is pseudo-equatorial in GC and the 6-membered ring E in iso-GC adopts a boat conformation.

Introduction of carbamate moieties into the various hydroxyl groups of ginkgolides was next investigated since such derivatives would yield important information for SAR studies. Carbamates at C-7 were efficiently prepared from 16 in two steps (Scheme 5) by reaction with p-nitrophenylchloroformate and pyridine in $CH_2Cl_2$ to form 33 in 61% yield; carbonate 33 was further reacted with various aliphatic amines in THF to yield carbamates 34-37 (81-92% yield, Table 2).

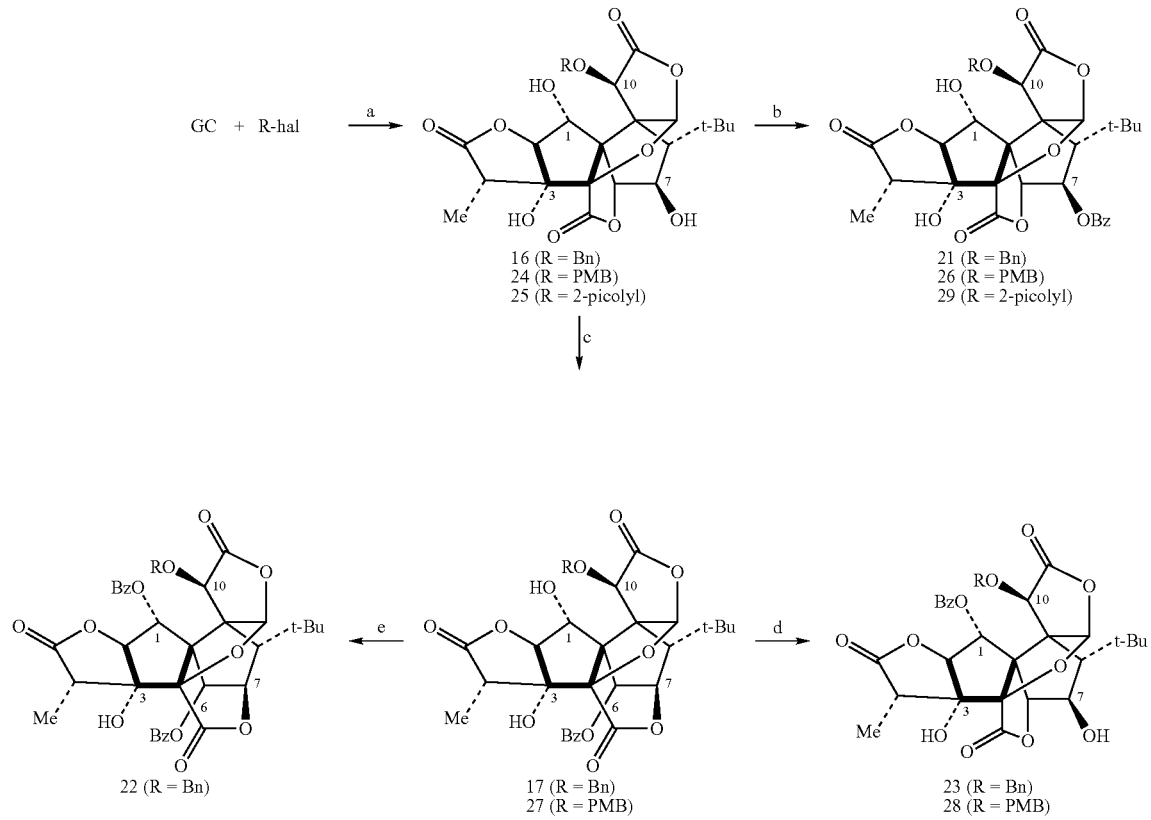

a $K_2CO_3$, DMF;
b BzCl (3 eq.), pyridine, $CH_2Cl_2$;
c $Bz_2O$ (3 eq.), $iPr_2EtN$, $CH_2Cl_2$;
d $iPr_2EtN$, DMF, 100° C.;
e $Bz_2O$ (6 eq.), $iPr_2EtN$, $CH_2Cl_2$ Scheme 4. Synthesis of ginkolide C benzoates. PMB =p-methoxybenzyl.

Figure 3:
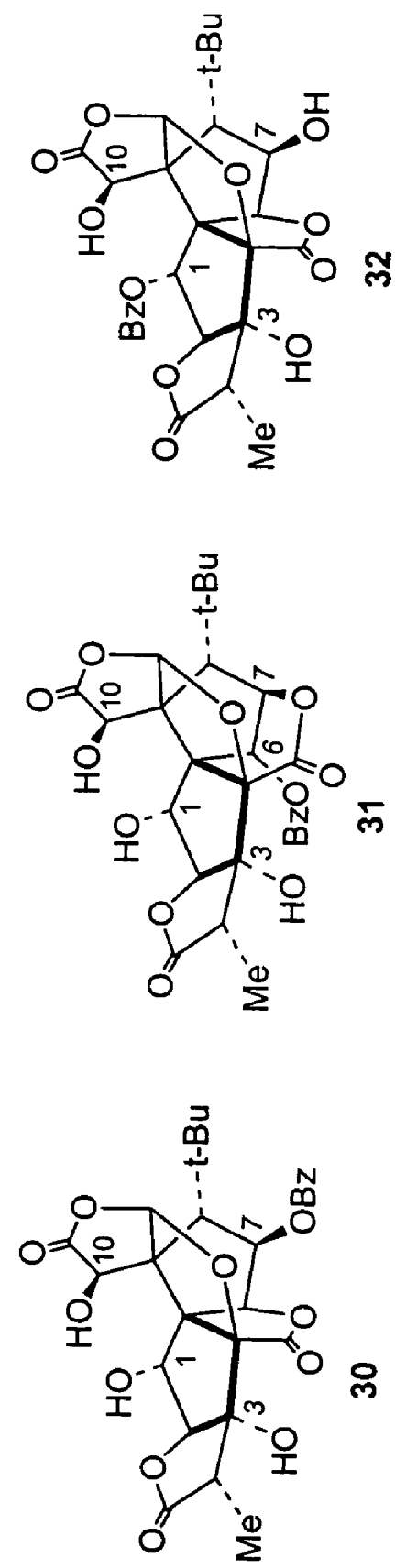
FIG. 3. Benzoates of Ginkgolide C.

According to previously established methods[23,43] 10-(4-methoxy-benzyloxy)-GC (24) and 10-(2-pyridinyl-methoxy)-GC (25) were prepared from GC in 94% and 97% yields, respectively (Scheme 4). Benzoate derivatives 26, 27, 28 and 29 were prepared from 24 and 25 using the same conditions as described above for 16 (Scheme 4). The ester derivatives prepared from 24 were consequently subjected to oxidative removal of the p-methoxybenzyl (PMB) group by cerium(IV) ammonium nitrate (CAN) to obtain derivatives 30, 31 and 32 (60-81% yield, FIG. 3). Milder oxidation reagents, such as dichlorodicyano quinone (DDQ) did not cleave the PMB group.

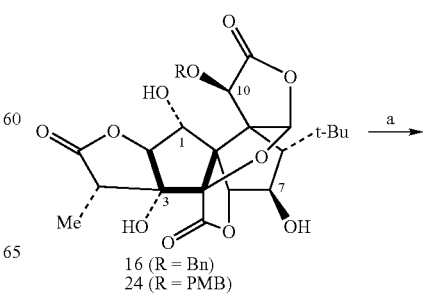

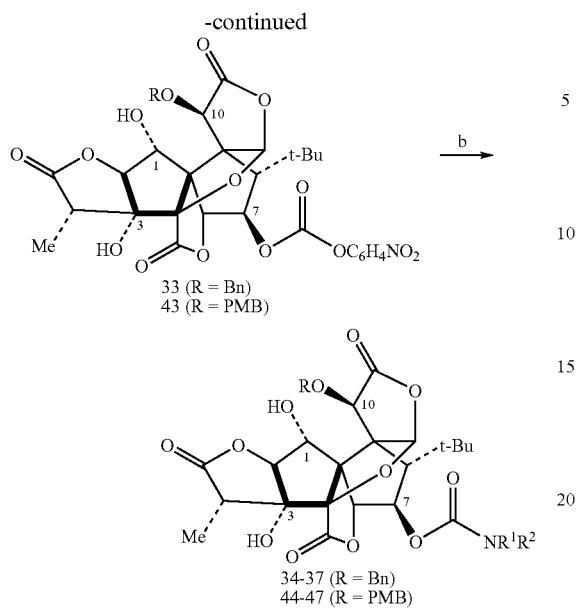
a ClCOOC$_6$H$_4$NO$_2$, pyridine, CH$_2$Cl$_2$;
b NHR$^1$R$^2$, THF
Scheme 5. Synthesis of C-7 carbamates from 10-alkyl substituted GC. PMB = p-methoxybenzyl.
Again, a remarkable difference was observed when Hünig's base was used instead of pyridine (Scheme 6).
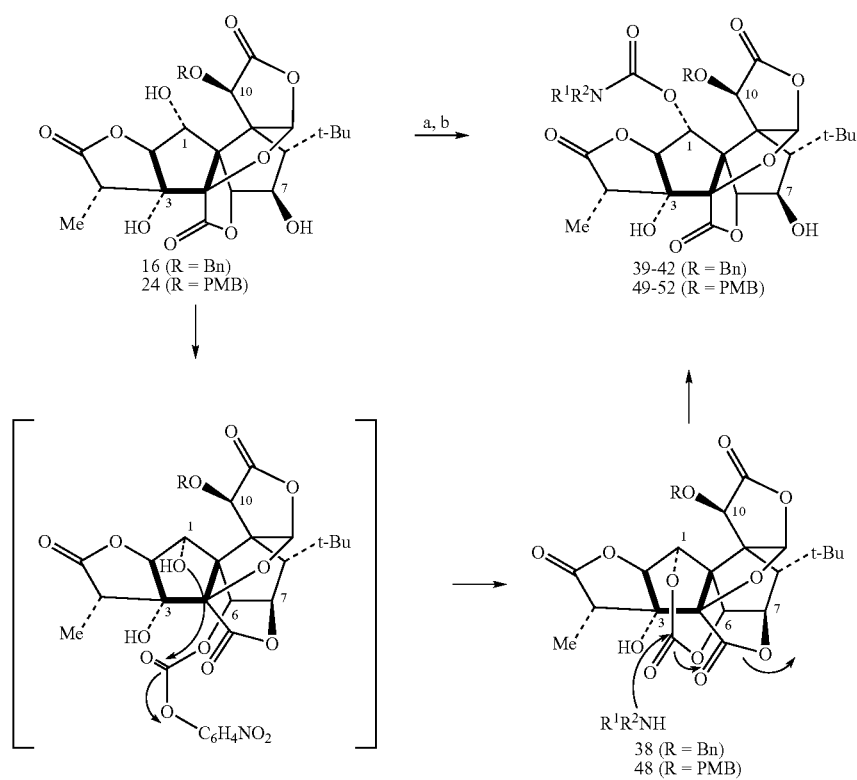
Scheme 6
a ClCOOC$_6$H$_4$NO$_2$, iPrEt$_2$N, CH$_2$Cl$_2$;
b NHR$^1$R$^2$, CH$_2$Cl$_2$/THF Scheme 6. Synthesis of C-1 carbamates from 10-alkyl substituted GC, Showing migratory mechanism. PMB=p-methoxybenzyl.

It is plausible that a highly reactive iso-GC 6-(p-nitrophenyl)carbonate is formed first, which reacts further with 1-OH as in the case of the migration of benzoate in 23. The product of this reaction, however, is cyclic carbonate 38 with a bridge between C-1 and C-6. This compound is unstable and hydrolyzes easily even on silica gel to form 16. Treatment of 38 with various aliphatic amines in THF provided facile opening of the carbonate bridge to form carbamates at C-1 with consequent translactonization of ring E into the native form, 39-42. Even bulky amines such as tert-butylamine reacted to completion in both cases forming 35 and 40, i.e., ginkgolides with two tert-butyl groups. All three reactions are performed in one pot to obtain the desired C-1 products in 50-78% yield from 16 after a single chromatography (Table 2). The corresponding sets of carbamates 44-47 (C-7) and 49-52 (C-1) were prepared from 24 (Schemes 5 and 6, Table 2), while removal of the PMB group afforded the nonaromatic ginkgolide carbamates 53-60 (Table 3).

Biological Activity

The ginkgolide derivatives were investigated for their abilities to antagonize glycine-induced responses from homomeric al GlyRs. In brief, homomeric al GlyR was stably expressed in HEK293 cells and a fluorescence-based membrane-potential kit was used to detect receptor activity. 53 The decrease in glycine response was measured by pre-incubation of the test compound prior to addition of 100 mM glycine. GC (3) was used as the reference compound. At a concentration of 10 mM GC (3) the response induced by glycine was inhibited by 97%. Due to the relatively low potency of all derivatives, they were investigated at a concentration of 100 mM for determination of the %-inhibition (Tables 2-5). However, none of the ginkgolide derivatives tested were more potent than the parent compound GC (3), and it follows that any modification of the hydroxyl groups leads to a significant decrease in biological activity. Thus, in the discussion below it should be noted that the relative differences between these derivatives are only minor since all compounds are only weak antagonists of the GlyR.

TABLE 2

Chemical yields and biological activities of C-7 and C-1 carbamates of 10-alkyl-GC.

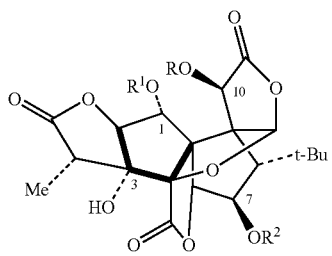

| compound | R | $R^1$ | $R^2$ | yield (%) | % inhibition[a] |
|---|---|---|---|---|---|
| 34 | Bn | H | CONHMe | 88[b] | NI |
| 35 | Bn | H | CONHtBu | 88[b] | 29 |
| 36 | Bn | H | $CONC_4H_8O$ | 92[b] | NI |
| 37 | Bn | H | $CONC_5H_{10}$ | 81[b] | NI |
| 39 | Bn | CONHMe | H | 64[c] | NI |

TABLE 2-continued

Chemical yields and biological activities of C-7 and C-1 carbamates of 10-alkyl-GC.

| compound | R | $R^1$ | $R^2$ | yield (%) | % inhibition[a] |
|---|---|---|---|---|---|
| 40 | Bn | CONHtBu | H | 59[c] | 42 |
| 41 | Bn | $CONC_4H_8O$ | H | 78[c] | NI |
| 42 | Bn | $CONC_5H_{10}$ | H | 50[c] | 31 |
| 44 | PMB | H | CONHMe | 74[d] | NI |
| 45 | PMB | H | CONHtBu | 77[d] | 39 |
| 46 | PMB | H | $CONC_4H_8O$ | 90[d] | NI |
| 47 | PMB | H | $CONC_5H_{10}$ | 86[d] | 29 |
| 49 | PMB | CONHMe | H | 67[e] | NI |
| 50 | PMB | CONHtBu | H | 60[e] | 33 |
| 51 | PMB | $CONC_4H_8O$ | H | 75[e] | NI |
| 52 | PMB | $CONC_5H_{10}$ | H | 53[e] | NI |

[a]Inhibition of 100 μM glycine-induced reponse by 100 μM of test compound; %-inhibition was calculated as: ($Response_{glycine}$ − $Response_{test\ cmpd+glycine}$)/$Response_{glycine}$. Values are means of three independent experiments preformed in duplicate.
[b]from 33.
[c]from 16.
[d]from 43.
[e]from 24. NI = no inhibition, i.e., inhibition below 20%. PMB = p-methoxybenzyl.

Ginkgolide derivatives with carbamates in position 1 or 7, and a benzyl or PMB group in the 10-position were either inactive at the concentrations tested, or only moderately active (Table 2). Interestingly, all derivatives with moderate activity contained a tert-butyl carbamate, and the presence of this group, rather than the position seems to be of importance for biological activity in this set of derivatives tested. For the corresponding carbamates without the benzyl or PMB group it appears as if both the position and the nature of the substituent are of importance (Table 3): Compounds 57 and 58 show a ca. 70% inhibition of the glycine responses, whereas other derivatives are either inactive or only moderately active. It is interesting to compare the activities of 57 with those of 39 and 49, the only difference being the benzyl substitution at 10-OH, thus indicating that the latter is detrimental for activity at GlyRs. Moreover, the activities of 57 and 58 compared to those of 53 and 54 show that substitution at 1-OH is preferred over 7-OH, while comparison with 59 and 60 indicates that there might be limitation to the size of the substituent that is tolerated.

TABLE 3

Chemical yields and biological activities of C-7 and C-1 carbamates of ginkgolide C.

| compound | $R^1$ | $R^2$ | yield (%) | % inhibition[b] |
|---|---|---|---|---|
| 53 | H | CONHMe | 69 | NI |
| 54 | H | CONHtBu | 80 | NI |
| 55 | H | CONC$_4$H$_8$O | 60 | 44 |
| 56 | H | CONC$_5$H$_{10}$ | 64 | 34 |
| 57 | CONHMe | H | 86 | 76 |
| 58 | CONHtBu | H | 84 | 71 |
| 59 | CONC$_4$H$_8$O | H | 80 | NI |
| 60 | CONC$_5$H$_{10}$ | H | 79 | 33 | a (NH$_4$)$_2$Ce(NO$_3$)$_6$, MeCN/H$_2$O/CHCl$_3$. PMB = p-methoxybenzyl
[a]Inhibition of 100 μM glycine-induced response by 100 μM of test compound; %-inhibition was calculated as: (Response$_{glycine}$ − Response$_{test\ cmpd+glycine}$)/Response$_{glycine}$. Values are means of three independent experiments performed in duplicate. NI = no inhibition, i.e., inhibition below 20%. PMB = p-methoxybenzyl.

The benzylated or benzoylated derivatives in Table 4 show a certain degree of variation in activities. The most potent derivatives are those with only one benzyl substituent in 10-OH, such as compounds 16, 24 and 25, and particularly 25 with a 2-picolyl substituent exhibits a 75% inhibition. Addition of benzoyl groups do not improve activity, while the presence of only benzoyl group, such as 30 and 32 leads to a complete loss in activity (Table 4).

TABLE 4

Biological activities of ginkgolide derivatives.

| compound | R | $R^1$ | $R^2$ | % inhibition[a] |
|---|---|---|---|---|
| 12 | MeO$_2$CCH$_2$C$_6$H$_4$CH$_2$ | H | H | NT |
| 13 | NH$_2$COCH$_2$C$_6$H$_4$CH$_2$ | H | H | NT |
| 16 | Bn | H | H | 59 |

TABLE 4-continued

Biological activities of ginkgolide derivatives.

| compound | R | $R^1$ | $R^2$ | % inhibition[a] |
|---|---|---|---|---|
| 21 | Bn | H | Bz | 45 |
| 23 | Bn | Bz | H | 60 |
| 24 | PMB | H | H | 52 |
| 25 | 2-picolyl | H | H | 75 |
| 26 | PMB | H | Bz | 35 |
| 28 | PMB | Bz | H | NI |
| 29 | 2-picolyl | H | Bz | 51 |
| 30 | H | H | Bz | NI |
| 32 | H | Bz | H | NI |

[a]Inhibition of 100 μM glycine-induced response by 100 μM of test compound; %-inhibition was calculated as: (Response$_{glycine}$ − Response$_{test\ cmpd+glycine}$)/Response$_{glycine}$. Values are means of three independent experiments performed in duplicate. NT = no tested. NI = no inhibition, i.e., inhibition below 20%. PMB = p-methoxybenzyl.

Finally a range of iso-ginkgolide derivatives were investigated, with some of them showing reasonable potencies (Table 5). Particularly compound 17, with a 90% inhibition in glycine responses is the most potent of the 43 derivatives, although still considerably less potent than GC (3), a 30 uM concentration of 17 giving only a 39% inhibition. However, rearrangement of the ginkgolide skeleton, as in the iso-ginkgolide derivatives, seems to be an acceptable modification for GlyR inhibition.

TABLE 5

Biological activities of iso-ginkgolide derivatives.

| compound | R | $R^1$ | $R^2$ | % inhibition[a] |
|---|---|---|---|---|
| 17 | Bn | H | Bz | 90 |
| 18 | MeO$_2$CCH$_2$C$_6$H$_4$CH$_2$ | Ac | Ac | NT |
| 19 | Bn | Ac | Ac | 21 |
| 20 | PMB | Ac | Ac | 36 |
| 22 | Bn | Bz | Bz | 42 |
| 27 | PMB | H | Bz | 49 |
| 31 | H | H | Bz | 63 |

[a]Inhibition of response induced by 100 μM glycine by 100 μM test compound; %-inhibition was calculated as: (Response$_{glycine}$ − Response$_{test\ cmpd+glycine}$)/Response$_{glycine}$. Values are means of three independent experiments performed in duplicate. NT = not tested. PMB = p-methoxybenzyl.

Discussion

We have shown that the solid-phase reactions of ginkgolides differ from those in solution; particularly, selectivity is greatly diminished. Although the preparation of linear peptides, oligosaccharides and nucleotides are performed routinely by the solid-phase method, the branched sugar analogs have to be prepared in solution using extensive protection/deprotection strategy (Plante, 2001; Tanaka, 2002; Ning, 2002). We have shown that ginkgolide C in solution can be selectively transformed into various derivatives via rearrangement and migration. Since hydroxyl groups that are unchanged in the product, e.g. 3-OH and 7-OH, participate during the reaction process their protection would presumably hamper the entire process. Thus the role of 7-OH in reactions described here is fundamental.

The synthesized ginkgolide derivatives were investigated as GlyR antagonists using a high-throughput assay, hence providing the first SAR study of ginkgolides and GlyR. In general, the ginkgolide derivatives prepared were less potent than the parent compound, GC (3) and in many cases the derivatives were totally devoid of activity. These results indicate that substitutions of the hydroxyl groups in ginkgolides are not beneficial for antagonistic activity at GlyR, and clearly other means of improving the activity of the parent compounds will be required in the future. In addition, these results show that the structure-activity relationships differ significantly from those observed with PAFR, as best exemplified by the iso-ginkgolide derivatives. When tested against PAFR, iso-GC acetates were devoid of activity;[41] however, in the present studies, although much less potent than the parent GC 3, the iso-ginkgolide derivative 17 was the most potent of the compounds tested.

Previous studies have indicated that ginkgolides might antagonize GlyRs by binding to an intra-ion channel site (Stromgaard, 2002; Stromgaard, 2003), thus acting as a plug in the ion channel of the GlyR. Moreover, it was suggested that the conformation of the ginkgolide was very important for antagonistic activity (Stromgaard, 2002). This study has shown that any modification of the hydroxyl groups leads to a significant loss in activity, which could be attributed to a change in the overall structure of the ginkgolides or by a reduction in the hydrogen bonding capacity of the hydroxyl groups. Further studies are needed to elucidate the binding of ginkgolides to the GlyRs.

REFERENCES

Abel, U.; Koch, C.; Speitling, M.; Hansske, F. G. Current Opinion in Chemical Biology 2002, 6, 453-458.

Ahlemeyer, B.; Krieglstein, J. ACS Symposium Series 1998, 691, 210-220.

Arya, P.; Baek, M.-G. Current Opinion in Chemical Biology 2001, 5, 292-301.

Beers, M.; Berkow, R. The Merck Manual 1999, 7$^{th}$ Editon, 1395-1396.

Betz H., H. R. J., Schloss P. Pharmacology of GABA and Glycine Neurotransmission. [In: Handb. Exp. Pharmacol., 2001; 150]; Springer-Verlag, 2001.

Braquet, P.; Spinnewyn, B.; Braquet, M.; Bourgain, R. H.; Taylor, J. E.; Etienne, A.; Drieu, K. Blood vessels 1985, 16, 558-572.

Braquet, P.; Drieu, K.; Etienne, A. Actual. Chim. Ther. 1986, 13, 237-254.

Braquet, P. Drugs of the Future 1987, 12, 643-699.

Braquet, P.; Esanu, A.; Buisine, E.; Hosford, D.; Broquet, C.; Koltai, M. Medicinal Research Reviews 1991, 11, 295-355.

Cazaux, J. B.; Dafniet, M.; Rebollo, J.; Teng, B. P. In UK Patent: France, 1995.

Chan, T. H.; Huang, W. Q. J. Chem. Soc., Chem. Commun. 1985, 909-911.

Chattipakorn, S. C.; McMahon, L. L. Journal of Neurophysiology 2002, 87, 1515-1525.

Corey, E. J.; Gavai, A. V. Tetrahedron Lett. 1989, 30, 6959-6962.

Corey, E. J.; Rao, K. S. Tetrahedron Lett. 1991, 32, 4623-4626.

Corey, E. J.; Rao, K. S.; Ghosh, A. K. Tetrahedron Lett. 1992, 33, 6955-6958.

DeFeudis, F. V. Ginkgo Biloba Extract (EGb 761): from Chemistry to the Clinic, 1998.

DeFeudis, F. V.; Drieu, K. Curr. Drug Targets 2000, 1, 25-58.

Drieu, K. Presse Med. 1986, 15, 1455-1457.

Ganesan, A. Drug Discovery Today 2002, 7, 47-55.

Goethe, J. W.; West-Ostlicher Divan: Tuebingen, 1819.

Hu, L.; Chen, Z.; Xie, Y.; Jiang, H.; Zhen, H. Bioorg. Med. Chem. 2000, 8, 1515-1521.

Hu, L.; Chen, Z.; Xie, Y.; Jiang, Y.; Zhen, H. J. Asian Nat. Prod. Res. 2000, 2, 103-110.

Hu, L.; Chen, Z.; Xie, Y. J. Asian Nat. Prod. Res. 2001, 3, 219-227.

Iglesias, B.; Alvarez, R.; de Lera, A. R. Tetrahedron 2001, 57, 3125-3130.

Jaracz, S.; Stromgaard, K.; Nakanishi, K. Journal of Organic Chemistry 2002, 67, 4623-4626.

Kondratskaya, E. L.; Krishtal, O. A. Neurophysiology (Translation of Neirofiziologiya) 2002, 34, 155-157.

Krchnak, V.; Holladay, M. W. Chemical Reviews (Washington, D.C.) 2002, 102, 61-91.

Kuisle, O.; Lolo, M.; Quinoa, E.; Riguera, R. Tetrahedron 1999, 55, 14807-14812.

Lee, Y.; Silverman, R. B. Tetrahedron 2001, 57, 5339-5352.

Marcaurelle, L. A.; Seeberger, P. H. Current Opinion in Chemical Biology 2002, 6, 289-296.

Maruyama, M.; Terahara, A.; Nakadaira, Y.; Woods, M. C.; Nakanishi, K. Tetrahedron Lett. 1967, 309-313.

Maruyama, M.; Terahara, A.; Itagaki, Y.; Nakanishi, K. Tetrahedron Lett. 1967, 299-302.

Maruyama, M.; Terahara, A.; Itagaki, Y.; Nakanishi, K. Tetrahedron Lett. 1967, 303-308.

McKenna, D. J.; Jones, K.; Hughes, K. Alternative Therapies 2001, 7, 70-90.

Nakanishi, K. Pure Appl. Chem. 1967, 14, 89-113.

Ning, J.; Yi, Y. T.; Kong, F. Z. Tetrahedron Letters 2002, 43, 5545-5549.

Okabe, K.; Yamada, K.; Yamamura, S.; Takada, S. J. Chem. Soc. C 1967, 2201-2206.

Park, H. K.; Lee, S. K.; Park, P. U.; Kwak, W. J. In PCT Int. Appl.; (Sunkyong Industries Co., Ltd., S. Korea). Wo, 1993, p 24 pp.

Park, P.-U.; Pyo, S.; Lee, S.-K.; Sung, J. H.; Kwak, W. J.; Park, H.-K.; Cho, Y.-B.; Ryu, G.-H.; Kim, T. S. In PCT Int. Appl.; (Sunkyong Industries Co., Ltd., S. Korea). Wo, 1995, p 96 pp.

Plunkett, M. J.; Ellman, J. A. Journal of Organic Chemistry 1995, 60, 6006-6007.

Peskind, E. R. Journal of Clinical Psychiatry 1998, 59(9), 22-27.

Plante, O. J.; Palmacci, E. R.; Seeberger, P. H. Science (Washington, D.C., United States) 2001, 291, 1523-1527.

Randolph, J. T.; McClure, K. F.; Danishefsky, S. J. J. Am. Chem. Soc. 1995, 117, 5712-5719.

Rapin, J. R.; Zaibi, M.; Drieu, K. Drug Develop. Res. 1998, 45, 23-29.

Schreiber, S. L. Science (Washington, D.C.) 2000, 287, 1964-1969.

Simonson, W. American Journal of Health-System Pharmacy 1998, 55, S11-S16.

Stromgaard, K.; Saito, D. R.; Shindou, H.; Ishii, S.; Shimizu, T.; Nakanishi, K. Journal of Medicinal Chemistry 2002, 45, 4038-4046.

Stromgaard, K.; Ivic, L.; Sands, T. T. J.; Fishkin, N.; Naanishi, K.; Kriegstein, A. R. Journal of Biological Chemistry, submitted 2003.

Stromgaard, K.; Nakanishi, K. Angew. Chem. Int. Ed. Engl. 2003, in press.

Takahashi, T.; Inoue, H.; Yamamura, Y.; Doi, T. Angewandte Chemie, International Edition 2001, 40, 3230-3233.

Tanaka, H.; Adachi, M.; Tsukamoto, H.; Ikeda, T.; Yamada, H.; Takahashi, T. Org. Lett. 2002, 4, 4213-4216.

Vogensen, S. B.; Stromgaard, K.; Shindou, H.; Jaracz, S.; Suchiro, M.; Ishii, S.; Shimizu, T.; Nakanishi, K. Journal of Medicinal Chemistry 2003, 46, 601-608.

Weinges, K.; Schick, H. Liebigs Ann. Chem. 1991, 81-83.

Weinges, K.; Hepp, M.; Jaggy, H. Liebigs Ann. Chem. 1987, 521-526.

What is claimed is:

1. A compound having the structure:

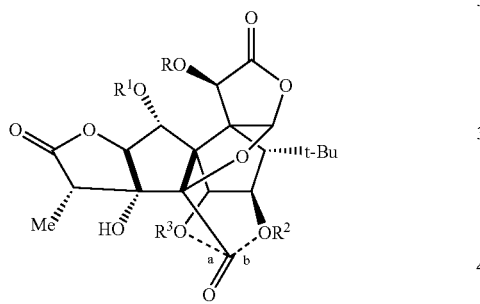

wherein R is H or -A-Ar,
where A is an alkyl group; and
Ar is an aryl group, which may contain heteroatoms and may be unsubstituted or substituted by one to five substituents each selected from the group consisting of alkoxy, —$CH_2CO_2R^4$, and —$CH_2CONR^5R^6$;
where $R^4$ is an alkyl group; and
$R^5$ and $R^6$ are each, independently, hydrogen or a branched or unbranched alkyl group;
wherein $R^1$ is H, —$CONC_5H_{10}$, —$CONC_4H_8O$ or —$COR^7$,
where $R^7$ is alkyl, aryl or —$NR^{5'}R^{6'}$;
where $R^{5'}$ and $R^{6'}$ are each, independently, hydrogen, methyl, or t-butyl;
wherein $R^2$ is present or absent, and when present is benzoyl, —$CO_2C_6H_4NO_2$, —CONHMe, —CONHtBu, —$CONC_5H_{10}$, —$CONC_4H_8O$, —$CONR^5R^6$ or —CO-phenyl which phenyl is substituted,
where $R^5$ and $R^6$ are each, independently, hydrogen, methyl, t-butyl,
or —CO—Z—$R^8$ where $R^8$ is alkyl, or aryl; and Z is oxygen;
or $R^2$ is H and $R^1$ is H, and R is p-methoxybenzyl, or picolyl, or $R^2$ is H and $R^1$ is —C(O)NHt-Bu, or —C(O)NHMe, and R is H,
wherein $R^3$ is present or absent, and when present is —$COR^9$;
where $R^9$ is alkyl or aryl;
wherein only one of $R^2$ or $R^3$ is present in the compound;
wherein only two of R, $R^1$, $R^2$ and $R^3$ are H; and
wherein each of a and b designates a single covalent bond which is present or absent,
where bond a is present when $R^3$ is absent and bond b is present when $R^2$ is absent;
or an optically pure enantiomer or a pharmaceutically acceptable salt of the compound.

2. The compound of claim 1, having the structure

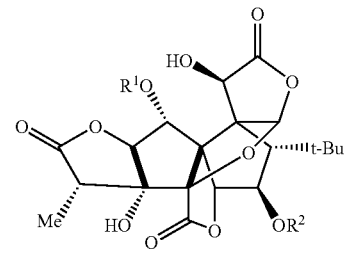

wherein R, $R^1$, and $R^2$ are as defined in claim 1.

3. The compound of claim 1, having the structure

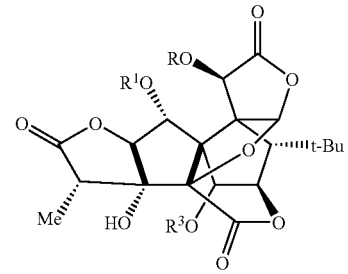

wherein R, $R^1$, and $R^3$ are as defined in claim 1.

4. The compound of claim 2, wherein R is H or -A-Ar-;
where A is —$CH_2$—,
Ar is a phenyl group or a picolyl group, either of which may be substituted or unsubstituted by a substituent selected from the group consisting of methoxy, —$CH_2CO_2Me$, and —$CH_2CONH_2$.

5. The compound of claim 4, wherein R is H, para-methoxybenzyl or picolyl.

6. The compound of claim 2, wherein $R^1$ is H or —$COR^7$;
where $R^7$ is methyl, phenyl or -$NR^5R^6$;
where $R^5$ and $R^6$ are each, independently, hydrogen, methyl, or t-butyl, or wherein $R^5$ and $R^6$ together with the nitrogen to which they are attached form a morpholine or piperidine.

7. The compound of claim 6, wherein $R^1$ is H, benzoyl, —COMe, —CONHMe, —CONHtBu, —$CONC_5H_{10}$, or —$CONC_4H_8O$.

8. The compound of claim 2, wherein $R^2$ is H, —$CONR^5R^6$ or —CO-phenyl where the phenyl is unsubstituted or substituted by one to five substituents which are each, independently, halogen or —$NO_2$.

9. The compound of claim 1, wherein R² is H, benzoyl, —CO₂C₆H₄NO₂, —CONHMe, —CONHtBu, CONC₅H₁₀, or CONC₄H₈O.

10. The compound of claim 3, wherein R is H or -A-Ar-; where A is —CH₂—,
    Ar is a phenyl group or a picolyl group, either of which may be substituted or unsubstituted by a substituent selected from the group consisting of methoxy, —CH₂CO₂Me, and —CH₂CONH₂.

11. The compound of claim 10, wherein R is H, p-methoxybenzyl or picolyl.

12. The compound of claim 3, wherein R¹ is H or —COR⁷, where R⁷ is methyl, phenyl or —NR⁵R⁶;
    where R⁵ and R⁶ are each, independently, hydrogen, methyl, or t-butyl, or wherein R⁵ and R⁶ together with the nitrogen to which they are attached together form a morpholine or piperidine.

13. The compound of claim 12, wherein R¹ is H, phenyl, —COMe, —CONHMe, —CONHtBu, —CONC₅H₁₀ or CONC₄H₈O.

14. The compound of claim 3, wherein R³ is benzoyl, —COMe or —CO₂C₆H₄NO₂.

15. The compound of claim 1, having the formula

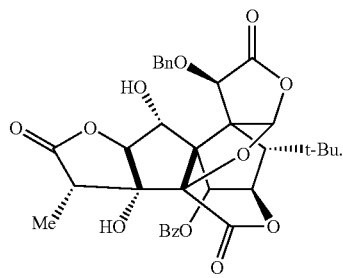

16. The compound of claim 1, having the structure

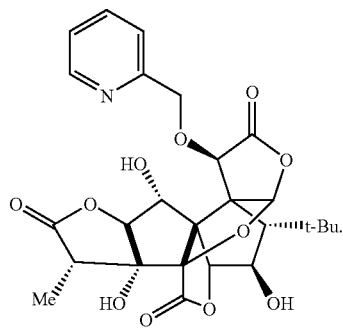

17. The compound of claim 1, having the structure

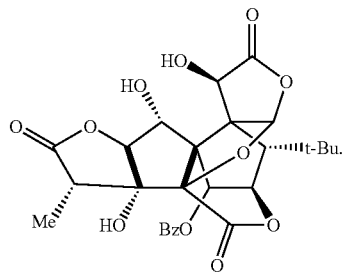

18. The compound of claim 1, having the structure

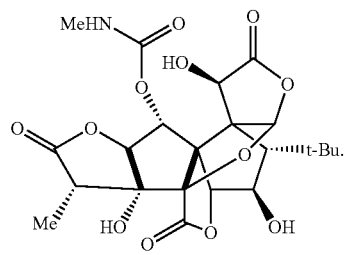

19. The compound of claim 1, having the structure

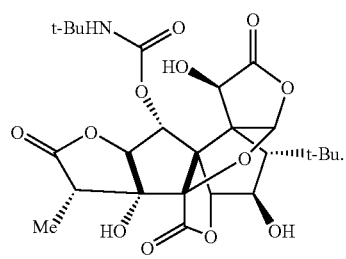

20. The compound of claim 1, having the structure

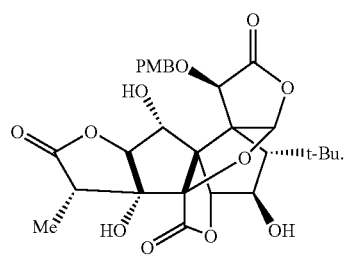

21. A composition comprising an amount of the compound of claim 15, 16, 17, 18 or 19 and a pharmaceutical carrier.

22. A process of preparing the compound of claim 1, comprising the step of reacting a compound having the structure

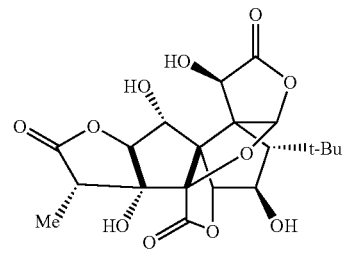

with an electrophile to form the compound.

23. A process of preparing the compound of claim 2, comprising the steps of:
    i) reacting a compound having the structure

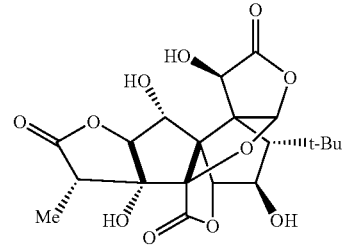

with either 4-methoxybenzyl chloride or benzyl chloride, and a base to form a compound having the structure

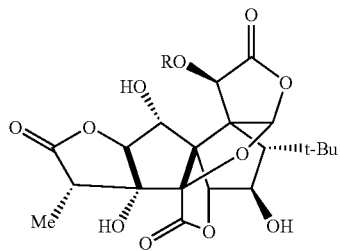

wherein R is benzyl or p-methoxybenzyl; and ii) reacting the product of step i) with an electrophilic reagents to form the compound of claim 2.

24. A process of preparing the compound of claim 3, comprising the steps of:

i) reacting a compound having the structure

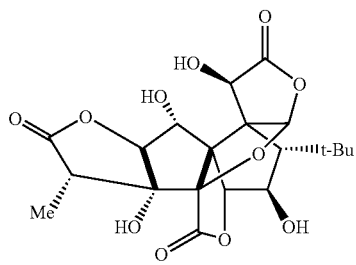

with 4-methoxybenzyl chloride or benzyl chloride, and a base to form a compound having the structure

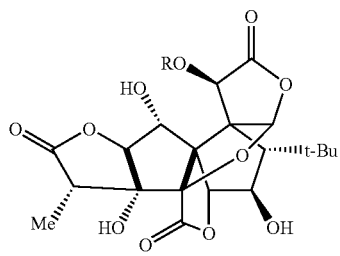

wherein R is benzyl or p-methoxybenzyl; and ii) reacting the product of step i) with electrophilic reagents to form the compound of claim 3.

25. A process of preparing the compound of claim 15, comprising the steps of:

i) reacting a compound having the structure

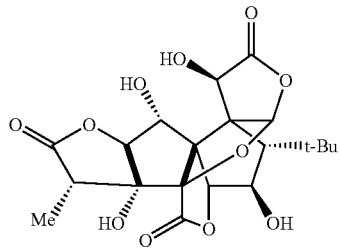

in dimethylformamide with a resin and a base to form a compound having the structure:

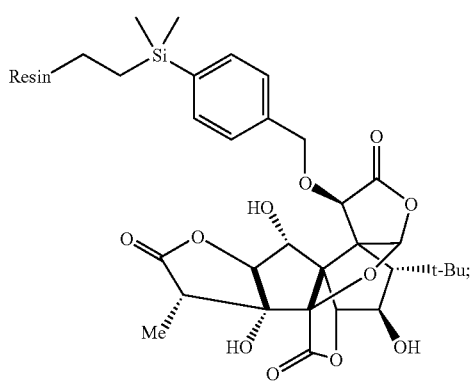

ii) cleaving the product of step i) from the resin by mixing the product of step i) with trifluoracetic acid in a polar solvent to form a compound having the structure

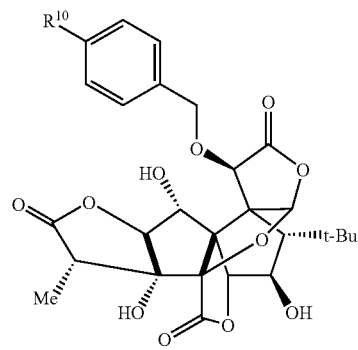

wherein $R^{10}$ is —H; and iii) dissolving the product of step ii) and an amine base in a solvent and reacting with benzoic anhydride, thereby forming the compound of claim 15.

26. A process of preparing the compound of claim 16, comprising the step of reacting a compound having the structure

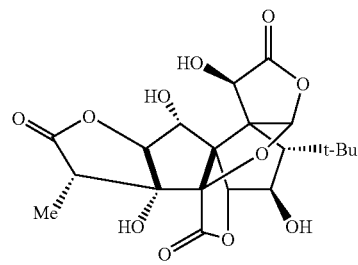

with 2-picolyl chloride in a polar solvent with a base, thereby forming the compound of claim 16.

27. A process of preparing the compound of claim 17, comprising the steps of:

i) reacting a compound having the structure

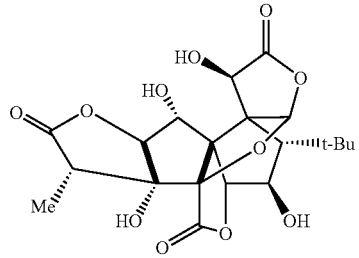

with 4-methoxybenzyl chloride in a polar solvent with a base, providing a compound having the structure

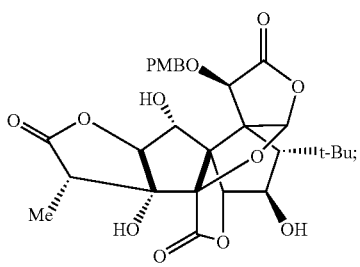

and ii) dissolving the product of step i) and a amine base in a polar solvent and reacting with benzoic anhydride, iii) and contacting the product of step ii) with cerium (IV) ammonium nitrate, thereby forming the compound of claim 17.

28. A process of preparing the compound of claim 18, comprising the steps of:

i) reacting a compound having the structure

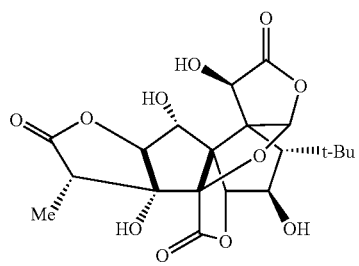

with 4-methoxybenzyl chloride in a polar solvent with a base, providing a compound having the structure

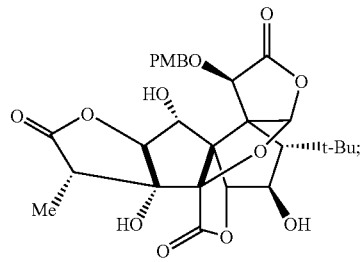

and ii) dissolving the product of step i) and iPr₂EtN base in a solvent and reacting with p-nitrophenyl chloroformate and then with MeNH₂, forming a compound having the structure

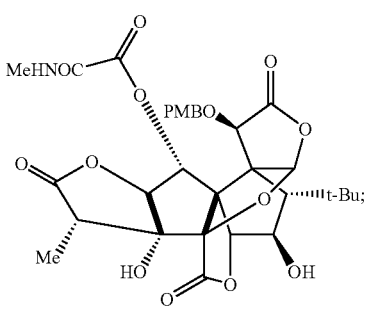

and iii) dissolving the product of step ii) in a solvent and reacting with (NH₄)₂Ce(NO₃)₆, thereby forming the compound of claim 18.

29. A process of preparing the compound of claim 19, comprising the steps of:

i) reacting a compound having the structure

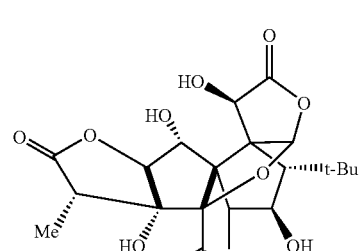

with 4-methoxybenzyl chloride in an a polar solvent with a base, providing a compound having the structure

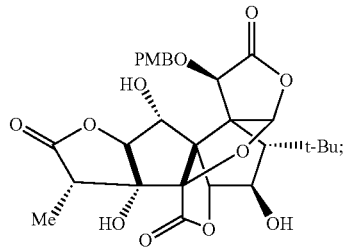

and
ii) dissolving the product of step i) and iPr$_2$EtN base in a solvent and reacting with p-nitrophenyl chloroformate and then with tBuNH$_2$, thereby forming the product

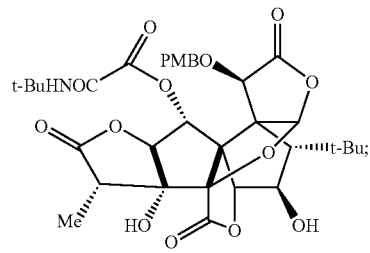

and
iii) dissolving the product of step ii) in a solvent and reacting with (NH$_4$)$_2$Ce(NO$_3$)$_6$, thereby forming the compound of claim 19.

* * * * *